US011293924B2

(12) United States Patent
Kagamu

(10) Patent No.: US 11,293,924 B2
(45) Date of Patent: Apr. 5, 2022

(54) IMMUNOLOGICAL BIOMARKER FOR PREDICTING CLINICAL EFFECT OF CANCER

(71) Applicant: Saitama Medical University, Saitama (JP)

(72) Inventor: Hiroshi Kagamu, Saitama (JP)

(73) Assignee: Saitama Medical University, Saitama (JP)

( * ) Notice: Subject to any disclaimer, the term of this patent is extended or adjusted under 35 U.S.C. 154(b) by 15 days.

(21) Appl. No.: 16/484,071

(22) PCT Filed: Feb. 6, 2018

(86) PCT No.: PCT/JP2018/004090
§ 371 (c)(1),
(2) Date: Aug. 6, 2019

(87) PCT Pub. No.: WO2018/147291
PCT Pub. Date: Aug. 16, 2018

(65) Prior Publication Data
US 2020/0025768 A1    Jan. 23, 2020

(30) Foreign Application Priority Data

Feb. 7, 2017 (JP) ............................. JP2017-020685
Jun. 2, 2017 (JP) ............................. JP2017-110069

(51) Int. Cl.
*G01N 33/574* (2006.01)
*C07K 16/18* (2006.01)
*C07K 16/28* (2006.01)

(52) U.S. Cl.
CPC ....... *G01N 33/57492* (2013.01); *C07K 16/18* (2013.01); *C07K 16/2812* (2013.01); *G01N 2333/70514* (2013.01); *G01N 2333/70564* (2013.01); *G01N 2333/7155* (2013.01)

(58) Field of Classification Search
None
See application file for complete search history.

(56) References Cited

U.S. PATENT DOCUMENTS

| 6,040,177 A | 3/2000 | Riddell et al. |
| 2010/0278873 A1 | 11/2010 | Avigan et al. |
| 2020/0393469 A1 | 12/2020 | Ito et al. |

FOREIGN PATENT DOCUMENTS

| JP | 2015-533796 A | 11/2015 |
| JP | 2017-538664 A | 12/2017 |
| WO | 2014/039983 A1 | 3/2014 |
| WO | 2014/140856 A2 | 9/2014 |
| WO | 2016/049641 A1 | 3/2016 |
| WO | 2017/140826 A1 | 8/2017 |
| WO | 2018/145023 A1 | 8/2018 |
| WO | 2018/147291 A1 | 8/2018 |
| WO | 2018/212237 A1 | 11/2018 |

OTHER PUBLICATIONS

Jenkins et al., BJC, vol. 118: 9-16 Petrausch, 2009, Curr Mol. Med. vol. 9: 671-682.*
Kamada eta l. 2019, PNAS, vol. 116: 9999-10008.*
Ruysscher et al., 2016, Annals of Oncol. 493-496.*
Sopper et al, 2017, vol. 35: 175-184.*
Liu et al., "Potent in vivo anti-tumor activity of isolated CD62L$^{low}$ lymph node cells sensitized in vivo with tumor lysate-pulsed DC-based vaccines," *Cytotherapy* 7(4):353-362, 2005.
Moreno et al., "Response to programmed cell death-1 blockade in a murine melanoma syngeneic model requires costimulation, CD4, and CD8 T cells," *Cancer Immunol Res.* 4(10):845-857, 2016.
Rosenblatt et al., "CT-011, Anti-PD-1 Antibody, Enhances Ex-Vivo T Cell Responses to Autologous Dendritic/Myeloma Fusion Vaccine Developed for the Treatment of Multiple Myeloma," *Blood* 114(22), 2009, 4 pages.
Tian et al., "A novel cancer vaccine with the ability to simultaneously produce anti-PD-1 antibody and GM-CSF in cancer cells and enhance TH1-biased antitumor immunity," *Signal Transduction and Targeted Therapy 1*, 16025, 2016, 15 pages.
Vavrova et al., "Generation of T cell effectors using tumor cell-loaded dendritic cells for adoptive T cell therapy," *Med Oncol* 33:136, 2016, 12 pages.
Zimmermann et al., "Tumors Hamper the Immunogenic Competence of CD4$^+$ T Cell-Directed Dendritic Cell Vaccination," *J Immunol* 179:2899-2909, 2007.
Cook et al., "Dexamethasone co-medication in cancer patients undergoing chemotherapy causes substantial immunomodulatory effects with implications for chemo-immunotherapy strategies," *OncoImmanology* 5:3,e-1066062, DOI: 10.1080/2162402X.2015.1066062, 2015, 12 pages.
Koyama et al., "Reciprocal CD4$^+$ T-Cell Balance of Effector CD62L$^{low}$ CD4$^+$ and CD62L$^{high}$ CD25$^+$ CD4$^+$ Regulatory T Cells in Small Cell Lung Cancer Reflects Disease Stage," *Clin Cancer Res* 14(21):6770-6779, 2008.

(Continued)

*Primary Examiner* — Amy E Juedes
(74) *Attorney, Agent, or Firm* — Seed IP Law Group LLP

(57) ABSTRACT

The present invention relates to the prediction of responsiveness to cancer immunotherapy of a subject based on the T-cell composition of the subject, and a therapeutic method using cancer immunotherapy based on the prediction. The present invention also provides a method for improving or maintaining responsiveness to cancer immunotherapy of a subject. Responsiveness to cancer immunotherapy is predict by determining a relative value of a CD4$^+$ T-cell subpopulation, dendritic cell subpopulation, and/or CD8$^+$ T-cell subpopulation correlated with a dendritic cell stimulation in an anti-tumor immune response in a sample derived from a subject. A composition for treating or preventing cancer comprising cells such as CD62L$^{low}$CD4$^+$ T-cells is also provided.

9 Claims, 35 Drawing Sheets

(56) References Cited

OTHER PUBLICATIONS

Baixeras et al., "Characterization of the Lymphocyte Activation Gene 3-Encoded Protein. A New Ligand for Human Leukocyte Antigen Class II Antigens," *J. Exp. Med.* 176:327-337, 1992.

Brahmer et al., "Nivolumab versus Docetaxel in Advanced Squamous-Cell Non-Small-Cell Lung Cancer," *N Engl J Med* 373:123-135, 2015.

Maccalli et al., "Immunological markers and clinical outcome of advanced melanoma patients receiving ipilimumab plus fotemustine in the NIBIT-M1 study," *OncoImmunology* 5(2):e1071007, 2016 (11 pages).

Martens et al., "Baseline Peripheral Blood Biomarkers Associated with Clinical Outcome of Advanced Melanoma Patients Treated with Ipilimumab," *Clin Cancer Res* 22(12):2908-2918, 2016 (12 pages).

O'Mahony et al., "A Pilot Study of CTLA-4 Blockade after Cancer Vaccine Failure in Patients with Advanced Malignancy," *Clin Cancer Res* 13(3):958-964, 2007 (8 pages).

Shien et al., "Predictive biomarkers of response to PD-1/PD-L1 immune checkpoint inhibitors in non-small cell lung cancer," *Lung Cancer* 99:79-87, 2016 (19 pages).

Wang et al., "PD-L1 expression in human cancers and its association with clinical outcomes," *OncoTargets and Therapy* 9:5023-5039, 2016.

Manjarrez-Orduño et al., "Circulating T Cell Subpopulations Correlate With Immune Responses at the Tumor Site and Clinical Response to PD1 Inhibition in Non-Small Cell Lung Cancer," *Frontiers in Immunology* 9(1613), 2018.

Yoshimoto et al., "Special issue, New development of immunotherapy, Combination therapy including immunotherapy, Combination of immunotherapy and radiation therapy," *Journal of Molecular Targeted Therapy for Cancer* 15(2): 164-168, Jul. 2017.

\* cited by examiner

| Cutoff | Sensitivity% | 95% CI | Specificity% | 95% CI | Likelihood ratio |
|---|---|---|---|---|---|
| <10.9 | 7.143 | 0.1807% to 33.87% | 100 | 88.43% to 100% | |
| <12.3 | 14.29 | 1.779% to 42.81% | 100 | 88.43% to 100% | |
| <13.3 | 21.43 | 4.658% to 50.8% | 100 | 88.43% to 100% | |
| <13.8 | 28.57 | 8.389% to 58.1% | 100 | 88.43% to 100% | |
| <14.45 | 35.71 | 12.76% to 64.86% | 100 | 88.43% to 100% | |
| <15.75 | 35.71 | 12.76% to 64.86% | 96.67 | 82.78% to 99.92% | 10.71 |
| <16.6 | 42.86 | 17.66% to 71.14% | 96.67 | 82.78% to 99.92% | 12.86 |
| <16.85 | 50 | 23.04% to 76.96% | 96.67 | 82.78% to 99.92% | 15 |
| <17.1 | 57.14 | 28.86% to 82.34% | 96.67 | 82.78% to 99.92% | 17.14 |
| <17.3 | 64.29 | 35.14% to 87.24% | 96.67 | 82.78% to 99.92% | 19.29 |
| <17.5 | 71.43 | 41.9% to 91.61% | 96.67 | 82.78% to 99.92% | 21.43 |
| <17.85 | 78.57 | 49.2% to 95.34% | 96.67 | 82.78% to 99.92% | 23.57 |
| <18.2 | 85.71 | 57.19% to 98.22% | 96.67 | 82.78% to 99.92% | 25.71 |
| <19.4 | 92.86 | 66.13% to 99.82% | 96.67 | 82.78% to 99.92% | 27.86 |
| <21.15 | 92.86 | 66.13% to 99.82% | 93.33 | 77.93% to 99.18% | 13.93 |
| <22.15 | 92.86 | 66.13% to 99.82% | 90 | 73.47% to 97.89% | 9.286 |
| <22.55 | 100 | 76.84% to 100% | 90 | 73.47% to 97.89% | 10 |
| <23.1 | 100 | 76.84% to 100% | 86.67 | 69.28% to 96.24% | 7.5 |
| <24.1 | 100 | 76.84% to 100% | 83.33 | 65.28% to 94.36% | 6 |
| <24.8 | 100 | 76.84% to 100% | 76.67 | 57.72% to 90.07% | 4.286 |
| <25.05 | 100 | 76.84% to 100% | 73.33 | 54.11% to 87.72% | 3.75 |
| <25.45 | 100 | 76.84% to 100% | 70 | 50.6% to 85.27% | 3.333 |
| <25.95 | 100 | 76.84% to 100% | 63.33 | 43.86% to 80.07% | 2.727 |
| <27 | 100 | 76.84% to 100% | 60 | 40.6% to 77.34% | 2.5 |
| <28.75 | 100 | 76.84% to 100% | 56.67 | 37.43% to 74.54% | 2.308 |
| <29.9 | 100 | 76.84% to 100% | 53.33 | 34.33% to 71.66% | 2.143 |
| <30.6 | 100 | 76.84% to 100% | 50 | 31.3% to 68.7% | 2 |
| <31.25 | 100 | 76.84% to 100% | 46.67 | 28.34% to 65.67% | 1.875 |
| <35.85 | 100 | 76.84% to 100% | 43.33 | 25.46% to 62.57% | 1.765 |
| <40.75 | 100 | 76.84% to 100% | 40 | 22.66% to 59.4% | 1.667 |
| <41.85 | 100 | 76.84% to 100% | 36.67 | 19.93% to 56.14% | 1.579 |
| <43.05 | 100 | 76.84% to 100% | 33.33 | 17.29% to 52.81% | 1.5 |
| <44.1 | 100 | 76.84% to 100% | 30 | 14.73% to 49.4% | 1.429 |
| <44.75 | 100 | 76.84% to 100% | 26.67 | 12.28% to 45.89% | 1.364 |
| <45.05 | 100 | 76.84% to 100% | 23.33 | 9.934% to 42.28% | 1.304 |
| <46.85 | 100 | 76.84% to 100% | 20 | 7.714% to 38.57% | 1.25 |
| <48.8 | 100 | 76.84% to 100% | 16.67 | 5.642% to 34.72% | 1.2 |
| <49.95 | 100 | 76.84% to 100% | 13.33 | 3.755% to 30.72% | 1.154 |
| <51 | 100 | 76.84% to 100% | 10 | 2.112% to 26.53% | 1.111 |
| <51.35 | 100 | 76.84% to 100% | 6.667 | 0.8178% to 22.07% | 1.071 |
| <52.25 | 100 | 76.84% to 100% | 3.333 | 0.08436% to 17.22% | 1.034 |

Fig.8

| Cutoff | Sensitivity% | 95% CI | Specificity% | 95% CI | Likelihood ratio |
|---|---|---|---|---|---|
| <2.17 | 7.143 | 0.1807% to 33.87% | 100 | 88.43% to 100% | |
| <2.635 | 14.29 | 1.779% to 42.81% | 100 | 88.43% to 100% | |
| <3.225 | 21.43 | 4.658% to 50.8% | 100 | 88.43% to 100% | |
| <3.77 | 28.57 | 8.389% to 58.1% | 100 | 88.43% to 100% | |
| <4.285 | 35.71 | 12.76% to 64.86% | 100 | 88.43% to 100% | |
| <5.01 | 42.86 | 17.66% to 71.14% | 100 | 88.43% to 100% | |
| <5.64 | 50 | 23.04% to 76.96% | 100 | 88.43% to 100% | |
| <6.31 | 57.14 | 28.86% to 82.34% | 100 | 88.43% to 100% | |
| <6.83 | 64.29 | 35.14% to 87.24% | 100 | 88.43% to 100% | |
| <7.35 | 71.43 | 41.9% to 91.61% | 100 | 88.43% to 100% | |
| <7.685 | 71.43 | 41.9% to 91.61% | 96.67 | 82.78% to 99.92% | 21.43 |
| <7.755 | 71.43 | 41.9% to 91.61% | 93.33 | 77.93% to 99.18% | 10.71 |
| <7.83 | 78.57 | 49.2% to 95.34% | 93.33 | 77.93% to 99.18% | 11.79 |
| <7.975 | 78.57 | 49.2% to 95.34% | 90 | 73.47% to 97.89% | 7.857 |
| <8.305 | 78.57 | 49.2% to 95.34% | 86.67 | 69.28% to 96.24% | 5.893 |
| <8.575 | 85.71 | 57.19% to 98.22% | 86.67 | 69.28% to 96.24% | 6.429 |
| <8.615 | 85.71 | 57.19% to 98.22% | 83.33 | 65.28% to 94.36% | 5.143 |
| <8.685 | 92.86 | 66.13% to 99.82% | 83.33 | 65.28% to 94.36% | 5.571 |
| <9.305 | 100 | 76.84% to 100% | 80 | 61.43% to 92.29% | 5 |
| <9.895 | 100 | 76.84% to 100% | 76.67 | 57.72% to 90.07% | 4.286 |
| <10.19 | 100 | 76.84% to 100% | 73.33 | 54.11% to 87.72% | 3.75 |
| <10.99 | 100 | 76.84% to 100% | 70 | 50.6% to 85.27% | 3.333 |
| <11.71 | 100 | 76.84% to 100% | 66.67 | 47.19% to 82.71% | 3 |
| <12.07 | 100 | 76.84% to 100% | 63.33 | 43.86% to 80.07% | 2.727 |
| <12.32 | 100 | 76.84% to 100% | 60 | 40.6% to 77.34% | 2.5 |
| <12.42 | 100 | 76.84% to 100% | 56.67 | 37.43% to 74.54% | 2.308 |
| <12.75 | 100 | 76.84% to 100% | 53.33 | 34.33% to 71.66% | 2.143 |
| <13.41 | 100 | 76.84% to 100% | 50 | 31.3% to 68.7% | 2 |
| <14.03 | 100 | 76.84% to 100% | 46.67 | 28.34% to 65.67% | 1.875 |
| <14.37 | 100 | 76.84% to 100% | 43.33 | 25.46% to 62.57% | 1.765 |
| <15.09 | 100 | 76.84% to 100% | 40 | 22.66% to 59.4% | 1.667 |
| <15.9 | 100 | 76.84% to 100% | 36.67 | 19.93% to 56.14% | 1.579 |
| <16.12 | 100 | 76.84% to 100% | 33.33 | 17.29% to 52.81% | 1.5 |
| <16.76 | 100 | 76.84% to 100% | 30 | 14.73% to 49.4% | 1.429 |
| <18.66 | 100 | 76.84% to 100% | 26.67 | 12.28% to 45.89% | 1.364 |
| <20.8 | 100 | 76.84% to 100% | 23.33 | 9.934% to 42.28% | 1.304 |
| <22.23 | 100 | 76.84% to 100% | 20 | 7.714% to 38.57% | 1.25 |
| <23.99 | 100 | 76.84% to 100% | 16.67 | 5.642% to 34.72% | 1.2 |
| <27.69 | 100 | 76.84% to 100% | 13.33 | 3.755% to 30.72% | 1.154 |
| <30.26 | 100 | 76.84% to 100% | 10 | 2.112% to 26.53% | 1.111 |
| <30.63 | 100 | 76.84% to 100% | 6.667 | 0.8178% to 22.07% | 1.071 |
| <41.01 | 100 | 76.84% to 100% | 3.333 | 0.08436% to 17.22% | 1.034 |

$X = [CD62L^{low} \text{ on } CD4^+]$
$Y = [CD25^+ Foxp3^+ \text{ on } CD4^+]$

Fig.10

| Cutoff | Sensitivity% | 95% CI | Specificity% | 95% CI | Likelihood ratio |
|---|---|---|---|---|---|
| < 25.14 | 7.143 | 0.1807% to 33.87% | 100 | 88.43% to 100% | |
| < 28.83 | 14.29 | 1.779% to 42.81% | 100 | 88.43% to 100% | |
| < 46.75 | 21.43 | 4.658% to 50.8% | 100 | 88.43% to 100% | |
| < 62.63 | 28.57 | 8.389% to 58.1% | 100 | 88.43% to 100% | |
| < 70.65 | 35.71 | 12.76% to 64.86% | 100 | 88.43% to 100% | |
| < 85.12 | 42.86 | 17.66% to 71.14% | 100 | 88.43% to 100% | |
| < 99.87 | 50 | 23.04% to 76.96% | 100 | 88.43% to 100% | |
| < 107.6 | 57.14 | 28.86% to 82.34% | 100 | 88.43% to 100% | |
| < 110.6 | 64.29 | 35.14% to 87.24% | 100 | 88.43% to 100% | |
| < 118.2 | 71.43 | 41.9% to 91.61% | 100 | 88.43% to 100% | |
| < 134.9 | 78.57 | 49.2% to 95.34% | 100 | 88.43% to 100% | |
| < 151.6 | 85.71 | 57.19% to 98.22% | 100 | 88.43% to 100% | |
| < 157.4 | 92.86 | 66.13% to 99.82% | 100 | 88.43% to 100% | |
| < 174.3 | 100 | 76.84% to 100% | 100 | 88.43% to 100% | |
| < 194.2 | 100 | 76.84% to 100% | 96.67 | 82.78% to 99.92% | 30 |
| < 202.3 | 100 | 76.84% to 100% | 93.33 | 77.93% to 99.18% | 15 |
| < 208.3 | 100 | 76.84% to 100% | 90 | 73.47% to 97.89% | 10 |
| < 210.9 | 100 | 76.84% to 100% | 86.67 | 69.28% to 96.24% | 7.5 |
| < 218.7 | 100 | 76.84% to 100% | 83.33 | 65.28% to 94.36% | 6 |
| < 229.9 | 100 | 76.84% to 100% | 80 | 61.43% to 92.29% | 5 |
| < 247.8 | 100 | 76.84% to 100% | 76.67 | 57.72% to 90.07% | 4.286 |
| < 264.6 | 100 | 76.84% to 100% | 73.33 | 54.11% to 87.72% | 3.75 |
| < 282.4 | 100 | 76.84% to 100% | 70 | 50.6% to 85.27% | 3.333 |
| < 297.6 | 100 | 76.84% to 100% | 66.67 | 47.19% to 82.71% | 3 |
| < 306.4 | 100 | 76.84% to 100% | 63.33 | 43.86% to 80.07% | 2.727 |
| < 317.4 | 100 | 76.84% to 100% | 60 | 40.6% to 77.34% | 2.5 |
| < 330.7 | 100 | 76.84% to 100% | 56.67 | 37.43% to 74.54% | 2.308 |
| < 356 | 100 | 76.84% to 100% | 53.33 | 34.33% to 71.66% | 2.143 |
| < 406.8 | 100 | 76.84% to 100% | 50 | 31.3% to 68.7% | 2 |
| < 460.5 | 100 | 76.84% to 100% | 46.67 | 28.34% to 65.67% | 1.875 |
| < 495.9 | 100 | 76.84% to 100% | 43.33 | 25.46% to 62.57% | 1.765 |
| < 514.8 | 100 | 76.84% to 100% | 40 | 22.66% to 59.4% | 1.667 |
| < 619.6 | 100 | 76.84% to 100% | 36.67 | 19.93% to 56.14% | 1.579 |
| < 726.1 | 100 | 76.84% to 100% | 33.33 | 17.29% to 52.81% | 1.5 |
| < 770.4 | 100 | 76.84% to 100% | 30 | 14.73% to 49.4% | 1.429 |
| < 827.7 | 100 | 76.84% to 100% | 26.67 | 12.28% to 45.89% | 1.364 |
| < 894.5 | 100 | 76.84% to 100% | 23.33 | 9.934% to 42.28% | 1.304 |
| < 949.7 | 100 | 76.84% to 100% | 20 | 7.714% to 38.57% | 1.25 |
| < 985 | 100 | 76.84% to 100% | 16.67 | 5.642% to 34.72% | 1.2 |
| < 1067 | 100 | 76.84% to 100% | 13.33 | 3.755% to 30.72% | 1.154 |
| < 1351 | 100 | 76.84% to 100% | 10 | 2.112% to 26.53% | 1.111 |
| < 1591 | 100 | 76.84% to 100% | 6.667 | 0.8178% to 22.07% | 1.071 |
| < 2050 | 100 | 76.84% to 100% | 3.333 | 0.08436% to 17.22% | 1.034 |

Fig.12

| Cutoff | Sensitivity% | 95% CI | Specificity% | 95% CI | Likelihood ratio |
|---|---|---|---|---|---|
| <0.975 | 5.263 | 0.1332% to 26.03% | 100 | 71.51% to 100% | |
| <1.015 | 10.53 | 1.301% to 33.14% | 100 | 71.51% to 100% | |
| <1.065 | 15.79 | 3.383% to 39.58% | 100 | 71.51% to 100% | |
| <1.3 | 21.05 | 6.052% to 45.57% | 100 | 71.51% to 100% | |
| <1.54 | 26.32 | 9.147% to 51.2% | 100 | 71.51% to 100% | |
| <1.61 | 31.58 | 12.58% to 56.55% | 100 | 71.51% to 100% | |
| <1.7 | 36.84 | 16.29% to 61.64% | 100 | 71.51% to 100% | |
| <1.76 | 42.11 | 20.25% to 66.5% | 100 | 71.51% to 100% | |
| <1.895 | 47.37 | 24.45% to 71.14% | 100 | 71.51% to 100% | |
| <2.05 | 52.63 | 28.86% to 75.55% | 100 | 71.51% to 100% | |
| <2.125 | 52.63 | 28.86% to 75.55% | 90.91 | 58.72% to 99.77% | 5.789 |
| <2.205 | 52.63 | 28.86% to 75.55% | 81.82 | 48.22% to 97.72% | 2.895 |
| <2.26 | 57.89 | 33.5% to 79.75% | 81.82 | 48.22% to 97.72% | 3.184 |
| <2.33 | 57.89 | 33.5% to 79.75% | 72.73 | 39.03% to 93.98% | 2.123 |
| <2.385 | 57.89 | 33.5% to 79.75% | 63.64 | 30.79% to 89.07% | 1.592 |
| <2.47 | 63.16 | 38.36% to 83.71% | 63.64 | 30.79% to 89.07% | 1.737 |
| <2.67 | 68.42 | 43.45% to 87.42% | 63.64 | 30.79% to 89.07% | 1.882 |
| <2.795 | 68.42 | 43.45% to 87.42% | 54.55 | 23.38% to 83.25% | 1.505 |
| <2.83 | 73.68 | 48.8% to 90.85% | 45.45 | 16.75% to 76.62% | 1.351 |
| <2.96 | 78.95 | 54.43% to 93.95% | 45.45 | 16.75% to 76.62% | 1.447 |
| <3.12 | 84.21 | 60.42% to 96.62% | 45.45 | 16.75% to 76.62% | 1.544 |
| <3.21 | 94.74 | 73.97% to 99.87% | 45.45 | 16.75% to 76.62% | 1.737 |
| <3.26 | 94.74 | 73.97% to 99.87% | 36.36 | 10.93% to 69.21% | 1.489 |
| <3.3 | 94.74 | 73.97% to 99.87% | 27.27 | 6.022% to 60.97% | 1.303 |
| <3.35 | 100 | 82.35% to 100% | 27.27 | 6.022% to 60.97% | 1.375 |
| <3.63 | 100 | 82.35% to 100% | 18.18 | 2.283% to 51.78% | 1.222 |
| <4.365 | 100 | 82.35% to 100% | 9.091 | 0.2299% to 41.28% | 1.1 |

[Fig. 13]

Fig. 14
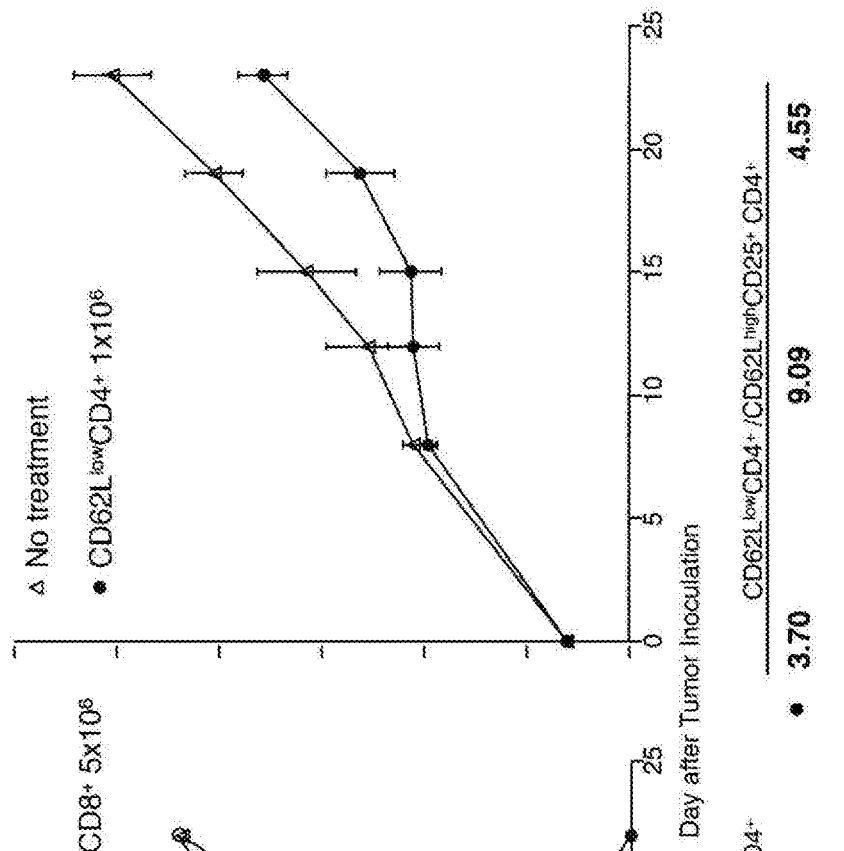
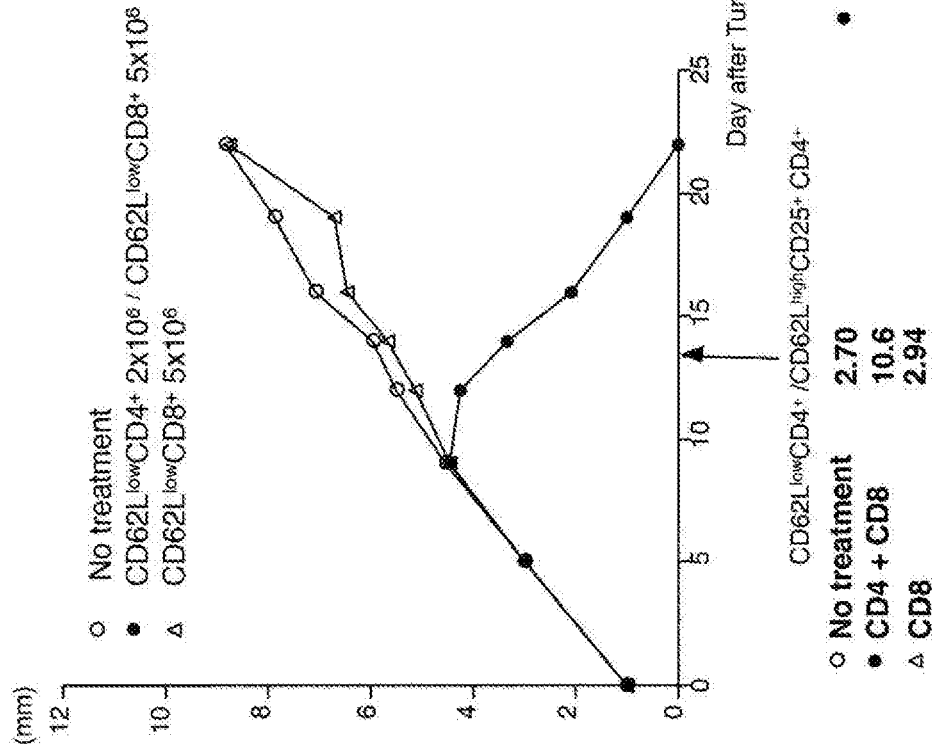

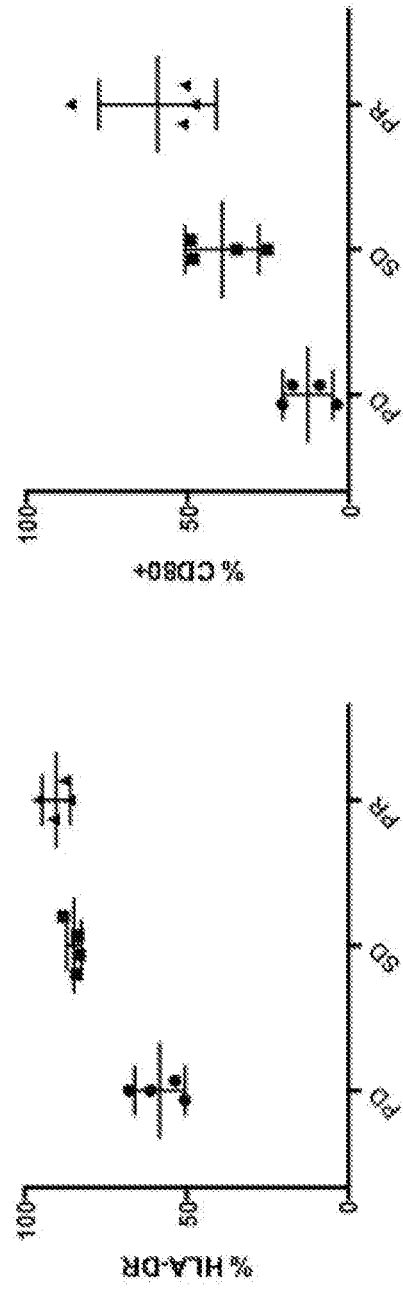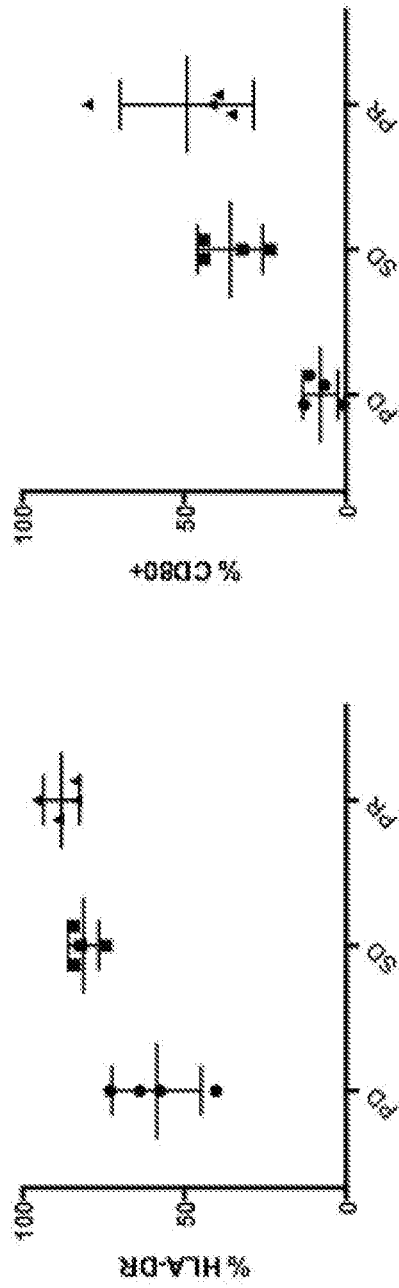
Fig. 16

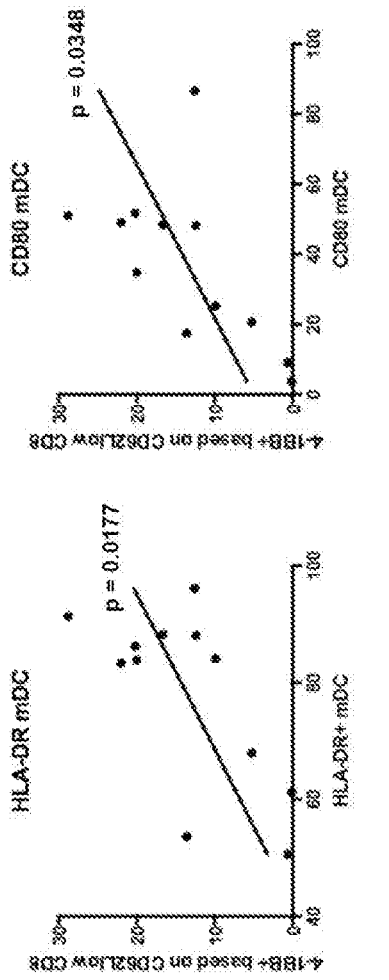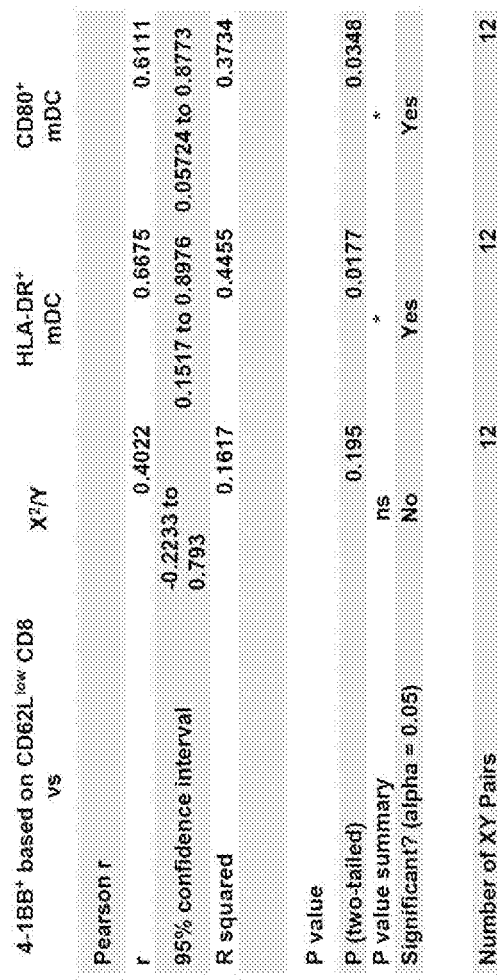
Fig.18

Fig. 23

| Generic name | Product name | Manufacturer | catalog number | isotype | Clone |
|---|---|---|---|---|---|
| CD4 | FITC Mouse Anti-Human CD4 | BD | 555346 | Mouse IgG1, κ | RPA-T4(RUO) |
| CD8 | FITC Mouse Anti-Human CD8 | BD | 555366 | Mouse IgG1, κ | RPA-T8(RUO) |
| CD11b | FITC Mouse Anti-Human CD11b/MAC-1 | BD | 562793 | Mouse IgG1, κ | ICRF44 |
| CD62L | FITC Mouse Anti-Human CD62L | BD | 555544 | Mouse IgG1, κ | DREG-56(RUO) |
| CD25 | PE Mouse Anti-Human CD25 | BD | 555432 | Mouse IgG1, κ | M-A251(RUO) |
| CD183(CXCR3) | PE Mouse Anti-Human CD183 | eBioscience | 12-9185-42 | Mouse (BALB/c) IgG1, κ | 1C6/CXCR3(RUO) |
| CD185(CXCR5) | Anti-Human CD185(CXCR5) PE | BD | 551120 | Mouse C57BL/6 IgG1, κ | MU5UBEE |
| CD194(CCR4) | PE Mouse Anti-Human CD194 | BD | 559862 | Mouse IgG2b, κ | 1G1(RUO) |
| CD196(CCR6) | PE Mouse Anti-Human CD196(CCR6) | BD | 552176 | Rat IgG2a, κ | 11A9(RUO) |
| CD197(CCR7) | PE Rat Anti-Human CD197(CCR7) | Miltenyi Biotec | 130-099-361 | recombinant human IgG1 | 3D12 |
| CD197(CCR7)* | CD197(CCR7)-PE | BD | 565616 | Mouse IgG1, κ | REA108 |
| LAG-3 | PE Mouse Anti-Human LAG-3(CD223) | BD | 557924 | Mouse IgG1, κ | T47-530(RUO) |
| CD274(PD-L1) | PE Mouse Anti-Human CD274 | BD | 557946 | Mouse (BALB/c) IgG1, κ | MIH1(RUO) |
| CD279(PD-1) | PE Mouse Anti-Human CD279 | eBioscience | 12-4776-42 | Rat IgG2a, κ | MIH4(RUO) |
| FoxP3 | Anti-Human Foxp3 PE | eBioscience | 555812 | Mouse IgG1, κ | PCH101 |
| HLA-DR | PE Mouse Anti-Human HLA-DR | eBioscience | 15-0116-42 | Mouse IgG1, κ | G46-6 |
| CD11c | Anti-Human CD11c PE-Cyanine5 | BD | 335789 | Mouse IgG heavy chains and κ light chains | 3.9 |
| CD25 | CD25 PE-Cy7 | eBioscience | 12-0209-42 | Mouse IgG1, κ | 2A3(RUO)(GMP) |
| CD80 | Anti-Human CD80 PE | BECKMAN COULTER | PN B43299 | Mouse IgG1, κ | 2D10.4 |
| CD141 | CD141 FITC | BD | 559663 | Mouse IgG2a, κ | M80 |
| CD123 | FITC Mouse Anti-Human CD123 | BD | 555958 | Mouse (BALB/c) IgG1, κ | 7G3(RUO) |
| CD137 | PE Mouse Anti-Human CD137 | eBioscience | 12-0949-42 | Mouse IgG1, κ | 4B4-1 |
| ICOS | PE Mouse Anti-Human ICOS (CD278) | | | | ISA-3 |

Fig.24 single-marker signature

- Logit (PR ratio as of week 8) = $a + \hat{b} \times$ (biomarker)

| Univariate analysis | estimated value ($\hat{b}$) | P value | AUC |
|---|---|---|---|
| log CD62L^low CD4+ T | 1.919 | 0.10 | 0.67 |
| CD62L^low CD4+ T | 0.047 | 0.16 | |
| log CD25+Foxp3+CD4+ T | 2.952 | 0.03 | 0.75 |
| CD25+Foxp3+CD4+ T | 1.264 | 0.02 | |
| log ICOS+CD62L^low based on CD4+ T | 0.582 | 0.06 | 0.76 |
| ICOS+CD62L^low based on CD4+ T | 5.535 | 0.01 | |
| log ICOS+ based on CD62L^low CD4+ T | 0.308 | 0.20 | 0.76 |
| ICOS+ based on CD62L^low CD4+ T | 1.909 | 0.01 | |

*Cases of ICOS+ based on CD62LlowCD4+T=0% are analyzed as ln(0.001%).
*Calculated by ICOS+CD62L^low based on CD4+T=(ICOS+ based on CD62LlowCD4+T)×(CD62L^lowCD4+T).
* AUC, area under the curve.
N=32

Fig.25

Multiple-marker signature, 2 BMs cont.

- Logit (PR ratio as of week 8) $= a + \hat{b} \times (BM1) + \hat{c} \times (BM2)$

| Model 4 | Estimated coefficient | P-value | AUC |
|---|---|---|---|
| Intercept (a) | -1.488 | | |
| logCD25+Foxp3+CD4+ T | 2.639 | 0.04 | 0.84 |
| logICOS+CD62L$^{low}$ based on CD4+ T | 0.512 | 0.15 | |

(CD25+Foxp3+CD4+T)$^5$ × (ICOS+CD62L$^{low}$ based on CD4+ T)

Fig. 27

Estimation results of logistic regression
(updated; development set N=40cases)

Prediction formula estimated by logistic regression model

Logit (Ratio of SD or greater as of 8w)
$= -23.00 + 8.776 \times \log \text{CD62L}^{low}\text{CD4+ T cell fraction}$
$\quad - 3.545 \times \log \text{CD25+Foxp3+CD4+ T cell fraction}$
$\doteq -23.00 + 3.5 \times \log (X^{2.475}/Y)$

| Predictive factor | Estimated value | p value |
|---|---|---|
| Intercept | -22.999 | — |
| logCD62L$^{low}$CD4+ T (X) | 8.776 | 0.004 |
| logCD25+Foxp3+CD4+ T (Y) | -3.545 | 0.068 |

※ Since they are completely separated, penalized maximum likelihood estimation value was found using Firth's method.

Fig. 34 a.

| CD62L$^{low}$ > CD62L$^{high}$ | CD62L$^{low}$ << CD62L$^{high}$ |
|---|---|
| AURAKA | BACH2 |
| CCL17 | CCL28 |
| CD101 | CCR7 |
| CD24 | CD27 |
| FOXP1 | CD28 |
| GZMA | CD62L |
| GZMB | CSNK1D |
| IL18RAP | FOXP1 |
| IL21 | FOXP3 |
| IL5RA | FGFR |
| ND2 | IL16 |
| SMAD5 | IL27RA |
| SMAD7 | IL6R |
| VEGFA | LEF1 |
|  | MAL |
|  | TCF7 | b.

| | GR > NR | GR > IR | GR+IR > NR |
|---|---|---|---|
| CXCR3 | | | + |
| CCL19 | + | + | |
| CCL3 | + | + | + |
| CCL7 | + | + | |
| XCL1 | + | + | + |
| CD80 | + | + | + |
| CLEC2A | + | + | + |
| CTAGE1 | + | + | |
| EPS8 | + | + | + |
| ERBB3 | + | + | |
| FGF5 | + | + | |
| FKBP14 | + | | + |
| FOXA1 | + | + | |
| FOXB1 | + | + | |
| IFNA10 | + | + | |
| IFNA17 | + | + | + |
| IFNA4 | + | + | + |
| IL23B | + | + | |
| IL13RA2 | + | + | + |
| IL7 | + | + | |
| IL11 | + | + | |
| IL34 | + | + | |
| PDCD1LG2 | + | + | + |
| TGFBR3 | + | + | + |
| TIAM2 | + | + | + |
| CD180 | + | + | + |
| HLA-DPA1 | + | | + |
| HLA-DQA1 | + | | + |
| HLA-DRA | + | | + |
| TGFBR1 | + | | + |
| CD59 | + | | + |
| FKBP7 | | | + |
| HDAC9 | | + | + |
| IFNA8 | | | + |
| NRCAM | | | + |
| CD4 | | | + |
| MYD88 | | | + |
| NFAT5 | | | + |
| ICAM | | + | + | a. Immunity-related genes that showed differential expression between CD62L$^{low}$ CD4+ T cells and CD62L$^{high}$ CD4+ T cells, commonly in good, intermediate, and non-responder patients. b. Fifty three genes related to immunity that showed differential expressions related to the response to Nivolumab in CD62L$^{low}$ CD4+ T cells: good responders (GR), intermediate responders (IR), and non-responders (NR).

[Fig. 35]
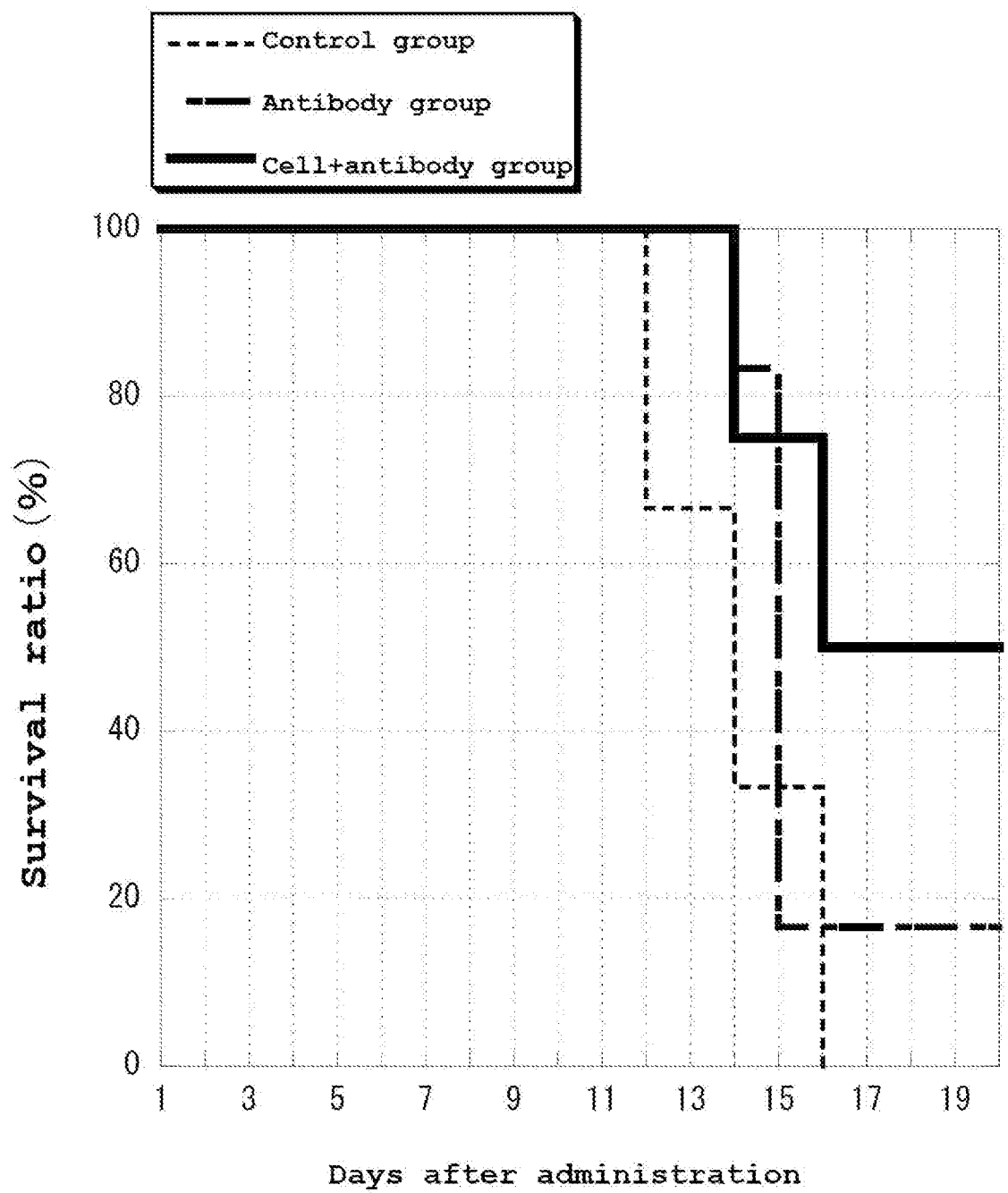

IMMUNOLOGICAL BIOMARKER FOR PREDICTING CLINICAL EFFECT OF CANCER

TECHNICAL FIELD

The present invention relates to the field of cancer immunotherapy. More specifically, the present invention relates to the prediction of responsiveness to cancer immunotherapy of a subject based on the T-cell composition of the subject, and a therapeutic method using cancer immunotherapy based on the prediction. In another aspect, the present invention provides a method of improving or maintaining responsiveness to cancer immunotherapy of a subject.

BACKGROUND ART

Cancer immunotherapy has drawn attention in recent years as having fewer side effects and exhibiting a greater effect compared to conventional anticancer therapies targeting the metabolism of cancer cells or the like (alkylating agents, platinum formulations, antimetabolites, topoisomerase inhibitors, microtubule polymerization inhibitors, microtubule depolymerization inhibitors, and the like). Among cancer immunotherapies, anti-PD-1 immune checkpoint inhibition has drawn particularly significant interest.

An anti-PD-1 antibody nivolumab is superior to docetaxel, which was conventionally the standard therapy as a secondary therapy of non-small cell lung cancer, by a large margin in all survival periods, thus becoming the standard therapy with a recommendation level of A in the Lung Cancer Society Guidelines (Brahmer J, et al. N Engl J Med 2015; 373: 123-135). Pembrolizumab, which is also an anti-PD-1 antibody, is superior to cytotoxic anticancer agents, which were conventionally the standard therapy in primary therapy, in all survival periods (note: in patients with expression of PD-L1 on tumor cells at 50% or greater). It has been decided that this will be the standard therapy for non-small cell lung cancer in the future.

The effect of anti-PD-1 antibodies is not limited to lung cancer. The effect is about to be proven in renal cancer, head and neck cancer, gastrointestinal cancer, gynecological cancer, malignant lymphoma, and breast cancer. Renal cancer is covered under insurance in Japan. Next year, head and neck cancer, gastrointestinal cancer, and malignant lymphoma are expected to be covered.

While anti-PD-1 antibodies appear to have achieved significant clinical success, anti-PD-1 antibodies in fact have significant problems. "Ineffective group", whose condition worsens within three months in almost all anti-PD-1 antibody clinical trials, is found from data for progression free survival (PFS). Meanwhile, in groups for which anti-PD-1 antibodies were effective for 1 year or longer, exacerbation in conditions was hardly observed thereafter, thus revealing that a state close to being healed is attained. This suggests the presence of three different subgroups, i.e., "ineffective group", "highly effective group" and "intermediate group" in terms of clinical effects, but a biomarker for the prediction thereof is not known. Administration of anti-PD-1 antibodies, which are expected to be the standard therapy in almost all cancer and tumor, to ineffective groups accounting for about 40%, which would be not only a medical problem, but also a problem for medical economics.

CITATION LIST

Non Patent Literature

[NPL 1] Brahmer J, et al. N Engl J Med 2015; 373: 123-135

SUMMARY OF INVENTION

Solution to Problem

The present invention provides a method of using the composition of $CD4^+$ T-cells of a subject as an indicator for predicting a response to cancer immunotherapy of the subject. The present invention also provides a method of using the composition of dendritic cells and/or $CD8^+$ T-cells of a subject as an indicator for predicting a response of the subject to immunotherapy. The present invention is partially based on the inventors discovering that the responsiveness to cancer immunotherapy is associated with the composition of T-cells and/or dendritic cells in a subject, and the responsiveness can be used as a biomarker. The biomarker of the present invention has a much higher level of sensitivity and specificity than conventionally studied biomarkers.

The inventors have discovered that the three groups of therapeutic effects to cancer immunotherapy (e.g., anti-PD-1 therapy or anti-PD-L1 therapy), i.e., progressive disease (PD), stable disease (SD), and response (complete response (CR)+partial response (PR)), each exhibits different immunological conditions. Some of the embodiments of the present invention provide a method of predicting a response to cancer immunotherapy as either progressive disease (PD), stable disease (SD), or response (complete response (CR)+ partial response (PR)) when cancer immunotherapy is applied to a subject. In the present invention, it should be noted that a population of subjects which includes complete response group (CR) with a partial response group (PR), or a population of subjects which includes a complete response group (CR) without a partial response group (PR), can be identified to be the same as a partial response group (PR).

One embodiment of the present invention is a method of using a relative amount of a $CD4^+$ T-cell subpopulation correlated with a dendritic cell stimulation in an anti-tumor immune response as an indicator for predicting a response to cancer immunotherapy of a subject. Examples of $CD4^+$ T-cell subpopulations correlated with a dendritic cell stimulation in an anti-tumor immune response include, but are not limited to, $CD4^+$ T-cell subpopulations with decreased expression of a homing molecule to a secondary lymphoid organ, $CD4^+$ T-cell subpopulations primed by an effector T-cell, $CD4^+$ T-cell subpopulations and regulatory T-cell subpopulations primed by antigen recognition.

The relative amount of a $CD4^+$ T-cell subpopulation is selected from the group consisting of:

a ratio of a $CD62L^{low}CD4^+$ T-cell subpopulation in $CD4^+$ T-cells;

a ratio of a $CCR7^-CD4^+$ T-cell subpopulation in $CD4^+$ T-cells;

a ratio of a $CD45RA^-CD4^+$ T-cell subpopulation in $CD4^+$ T-cells;

a ratio of a $CD45RO^+CD4^+$ T-cell subpopulation in $CD4^+$ T-cells;

a ratio of a $LAG-3^+CD62L^{low}CD4^+$ T-cell subpopulation in $CD62L^{low}CD4^+$ T-cells;

a ratio of an $ICOS^+CD62L^{low}CD4^+$ T-cell subpopulation in $CD62L^{low}CD4^+$ T-cells;

a ratio of a CD62L$^{high}$CD25$^+$CD4$^+$ T-cell subpopulation in CD4$^+$ T-cells;

a ratio of a CCR4$^+$CD25$^+$CD4$^+$ T-cell subpopulation in CD4$^+$ T-cells;

a ratio of a CD127$^+$CD25$^+$CD4$^+$ T-cell subpopulation in CD4$^+$ T-cells; and a ratio of a Foxp3$^+$CD25$^+$CD4$^+$ T-cell subpopulation in CD4$^+$ T-cells;

but is not limited thereto. The present invention provides, for example, a method of using a ratio of CD62L$^{low}$ T-cells in CD4$^+$ T-cells of a subject as an indicator for predicting a response to cancer immunotherapy of a subject. In one embodiment, the method comprises determining the ratio of CD62L$^{low}$ T-cells in CD4$^+$ T-cells in a sample derived from a subject. The ratio being higher than a threshold value (ineffective group threshold value) can indicate that the subject is not a part of an ineffective group with respect to the cancer immunotherapy.

Another embodiment of the present invention is a method of using a relative amount of a dendritic cell subpopulation correlated with a dendritic cell stimulation in an anti-tumor immune response as an indicator for predicting a response to cancer immunotherapy of a subject. Examples of dendritic cell subpopulations correlated with a dendritic cell stimulation in an anti-tumor immune response include, but are not limited to, dendritic cell subpopulations that increase due to an increase in a cell sub-population with decreased expression of a homing molecule in a CD4$^+$ T-cell population and dendritic cell subpopulations that increase due to an increase in a CD4$^+$ T-cell subpopulation primed by an effector T-cell in a CD4$^+$ T-cell population. Examples of dendritic cell subpopulations include, but are not limited to, HLA-DR$^+$ dendritic cell subpopulations, CD80$^+$ dendritic cell subpopulations, CD86$^+$ dendritic cell subpopulations, and PD-L1$^+$ dendritic cell subpopulations. Examples of dendritic cells include, but are not limited to, myeloid dendritic cells (mDC, CD141$^+$CD11c$^+$ dendritic cells) and plasmacytoid dendritic cells (pDC, CD123$^+$CD11c$^+$ dendritic cells).

Another embodiment of the present invention is a method of using a relative amount of a CD8$^+$ T-cell subpopulation correlated with a dendritic cell stimulation in an anti-tumor immune response as an indicator for predicting a response to cancer immunotherapy of a subject. Examples of CD8$^+$ T-cell subpopulation correlated with a dendritic cell stimulation in an anti-tumor immune response include, but are not limited to, CD8$^+$ T-cell subpopulations that increase due to an increase in a cell sub-population with decreased expression of a homing molecule in a CD4$^+$ T-cell population, CD8$^+$ T-cell subpopulations that increase due to an increase in a CD4$^+$ T-cell subpopulation primed by an effector T-cell in a CD4$^+$ T-cell population, CD8$^+$ T-cell subpopulations that increase due to an increase in a CD4$^+$ T-cell sub-population primed by antigen recognition in a CD4$^+$ T-cell population, CD8$^+$ T-cell subpopulations that increase due to an increase in a HLA-DR+ dendritic cell subpopulation in a dendritic cell population, CD8$^+$ T-cell subpopulations that increase due to an increase in a CD80$^+$ T-cell subpopulation in a dendritic cell population, and CD8$^+$ T-cell subpopulations that increase due to an increase in a PD-L1$^+$ dendritic cell subpopulation in a dendritic cell population. Furthermore, examples of CD8$^+$ T-cell subpopulations correlated with a dendritic cell stimulation in an anti-tumor immune response include, but are not limited to, CD62L$^{low}$CD8$^+$ T-cell subpopulation, CD137$^+$CD8$^+$ T-cell sub-population, and CD28$^+$CD62L$^{low}$CD8$^+$ T-cell subpopulation.

One embodiment of the present invention is a method of using an amount selected from:

an amount of a CD4$^+$ T-cell subpopulation correlated with a dendritic cell stimulation in an anti-tumor immune response;

an amount of a dendritic cell subpopulation correlated with a dendritic cell stimulation by a CD4$^+$ T-cell in an anti-tumor immune response;

an amount of a CD8$^+$ T-cell subpopulation correlated with a dendritic cell stimulation in an anti-tumor immune response;

an amount of regulatory T-cells or a CD4$^+$ T-cell subpopulation correlated with regulatory T-cells; and an amount of an ICOS$^+$ CD62L$^{low}$CD4$^+$ T-cell subpopulation;

in a subject as a variable (indicator) of a formula for predicting a response to cancer immunotherapy of the subject. In one embodiment, variables (X, Y) of the present invention are each selected from the group consisting of:

an amount of a CD62L$^{low}$CD4$^+$ T-cell subpopulation;

an amount of a CCR7$^-$CD4$^+$ T-cell subpopulation;

an amount of a LAG-3$^+$CD62L$^{low}$CD4$^+$ T-cell subpopulation;

an amount of an ICOS$^+$CD62L$^{low}$CD4$^+$ T-cell subpopulation;

an amount of a CD45RA$^-$CD4$^+$ T-cell subpopulation;

an amount of a CD45RO$^+$CD4$^+$ T-cell subpopulation;

an amount of a CCR4$^+$CD25$^+$CD4$^+$ T-cell subpopulation;

an amount of a CD62L$^{high}$CD25$^+$CD4$^+$ T-cell subpopulation;

an amount of a CD127$^+$CD25$^+$CD4$^+$ T-cell subpopulation; an amount of a CD45RA$^-$Foxp3$^+$CD4$^+$ T-cell subpopulation;

an amount of a Foxp3$^+$CD25$^+$CD4$^+$ T-cell subpopulation;

an amount of an HLA-DR$^+$ dendritic cell subpopulation;

an amount of a CD80$^+$ dendritic cell subpopulation;

an amount of a CD86$^+$ dendritic cell subpopulation;

an amount of a PD-L1$^+$ dendritic cell subpopulation;

an amount of a CD62L$^{low}$CD8$^+$ T-cell subpopulation;

an amount of a CD137$^+$CD8$^+$ T-cell subpopulation; and an amount of a CD28$^+$CD62L$^{low}$CD8$^+$ T-cell subpopulation.

In the present invention, (X) can be, for example, a value selected from the group consisting of:

an amount of a CD4$^+$ T-cell subpopulation correlated with a dendritic cell stimulation in an anti-tumor immune response;

an amount of a dendritic cell subpopulation correlated with a dendritic cell stimulation by a CD4$^+$ T-cell in an anti-tumor immune response; and an amount of a CD8$^+$ T-cell subpopulation correlated with a dendritic cell stimulation in an anti-tumor immune response. The method of the present invention can also calculate variables (X, Y), with a value selected from the group consisting of:

an amount of a CD62L$^{low}$CD4$^+$ T-cell subpopulation;

an amount of a CCR7$^-$CD4$^+$ T-cell subpopulation;

an amount of an LAG-3$^+$CD62L$^{low}$CD4$^+$ T-cell subpopulation;

an amount of an ICOS$^+$CD62L$^{low}$CD4$^+$ T-cell subpopulation;

an amount of a CD45RA$^{-CD}$4$^+$ T-cell subpopulation;

an amount of a CD45RO$^+$CD4$^+$ T-cell subpopulation;

an amount of an HLA-DR$^+$ dendritic cell subpopulation;

an amount of a CD80$^+$ dendritic cell subpopulation;

an amount of a CD86$^+$ dendritic cell subpopulation;

an amount of a PD-L1$^+$ dendritic cell subpopulation;

an amount of a CD62L$^{low}$CD8$^+$ T-cell subpopulation;
an amount of a CD137$^+$CD8$^+$ T-cell subpopulation; and
an amount of a CD28$^+$CD62L$^{low}$CD8$^+$ T-cell subpopulation; as (X).

For example, the method of the present invention can calculate variables (X, Y), with the amount of a regulatory T-cell subpopulation or the amount of a CD4$^+$ T-cell subpopulation correlated with a regulatory T-cell as (Y). The method of the present invention can also calculate variables (X, Y), a value selected from the group consisting of:
an amount of a CCR4$^+$CD25$^+$CD4$^+$ T-cell subpopulation;
an amount of a CD62L$^{high}$CD25$^+$CD4$^+$ T-cell subpopulation;
an amount of a CD127$^+$CD25$^+$CD4$^+$ T-cell subpopulation;
an amount of a CD45RA$^{31}$ Foxp3$^+$CD4$^+$ T-cell subpopulation; and
an amount of a CD4$^+$Foxp3$^+$CD25$^+$ T-cell subpopulation; as (Y).

The method of the present invention can use, for example, a comparison of a relative value of X to Y with a threshold value (ineffective group threshold value) comprising measuring the amount of CD4$^+$CD62L$^{low}$T-cells (X) and measuring the amount of CD4$^+$Foxp3$^+$CD25$^+$ T-cells (Y) as indicators for predicting that the subject is not a part of an ineffective group with respect to the cancer immunotherapy. The amount of a regulatory T-cell subpopulation or the amount or ratio of a CD4$^+$ T-cell subpopulation correlated with a regulatory T-cell can be used as (Y). In particular, examination of the ratio of CD62L$^{low}$CD4$^+$ T-cells/regulatory T-cells as a biomarker have not been reported up to this point, but the inventors have discovered that this ratio is very useful as a biomarker for predicting responsiveness to cancer immunotherapy.

The method of the present invention can use, for example, a comparison of a relative value of X to Y with a threshold value (ineffective group threshold value) comprising measuring the amount of CD80$^+$ dendritic cells (X) and measuring the amount of a CD28$^+$CD62L$^{low}$CD8$^+$ T-cell (Y) as an indicator for predicting that the subject is not a part of an ineffective group with respect to the cancer immunotherapy.

Since the inventors have discovered that multiple indicators independently exhibit correlation with responsiveness, multiple indicators can be combined for use as an indicator for responsiveness. When two or more indicators are combined as an indicator for responsiveness, an indicator represented by a formula using any number of variables can be used. Examples of an indicator of responsiveness include, but are not limited to the following when multiple indicators ($X_1$, $X_2$, $X_3$, ... $X_n$) are used:

$$F = a_1 X_1^{b1} + a_2 X_2^{b2} + a_3 X_3^{b3} \ldots + a_n X_n^{bn}$$

$$F = X_1^{c1} * X_2^{c2} * X_3^{c3} \ldots * X_n^{cn}$$

wherein each of a, b, and c is any real number. Responsiveness can be predicted from the difference derived from comparing a value calculated by such a formula (indicator) with a threshold value. Multivariate analysis (e.g., estimation by logistic regression) using discriminant analysis on the novel indicator discovered by the inventors can determine each coefficient for use as an indicator of responsiveness to cancer immunotherapy of a subject.

Typically, responsiveness can be predicted by formula F(X, Y) using two indicators (X, Y) disclosed herein as variables. In a specific embodiment, the formula is a relative value of X to Y.

Any function (F(X, Y)) of X and Y can be used as the relative value of X to Y. In particular, when X is considered to positively correlated with responsiveness and Y is negatively correlated with responsiveness, any function (F(X, Y)) of X and Y, which monotonically increases with respect to X and monotonically decreases with respect to Y, can be used, but is not limited thereto. A formula indicating responsiveness with two or more variables representing responsiveness can be found by regression by calculating the contribution of each variable to responsiveness.

Examples of formula F(X, Y) indicating responsiveness include, but are not limited to, the following:

$$F = aX^r + bY^s$$

$$F = X^r * Y^s$$

wherein a, b, r, and s are any real number.

For simplicity of the formula, an integer can be used as r and s. In some embodiments, examples of relative values of X to Y include, but are not limited to, $X^n/Y^m$ (n and m are any real number such as any integer) such as X/Y and $X^2/Y$. When factors X and Y each indicates responsiveness to therapy from different mechanisms, such a combination of indicators can make prediction of responsiveness more accurate. The investigation by the inventors demonstrated that responsiveness to cancer immunotherapy of a subject can be predicted more accurately using a formula with r and s in the range of −5 to 5.

Another aspect of the present invention provides a method of further predicting a subject who is a part of a response group (complete response (CR)+partial response (PR)) from among subjects who have been shown to be not a part of an ineffective group by using the composition of a CD4$^+$ T-cells of the subjects as an indicator of responsiveness to cancer immunotherapy.

One embodiment of the present invention is a method of using a ratio of a Foxp3$^+$CD25$^+$ T-cells in CD4$^+$ T-cells, ICOS$^+$CD62L$^{low}$CD4$^+$ T cells in CD62L$^{low}$CD4$^+$ T-cells, LAG-3$^+$CD62L$^{low}$CD4$^+$ T-cell subpopulation in CD62L$^{low}$CD4$^+$ T-cells, or PD-1$^+$CD62L$^{low}$CD4$^+$ T-cell subpopulation in CD62L$^{low}$CD4$^+$ T-cells in a subject, who is shown not to be a part of an ineffective group, as an indicator of a response to cancer immunotherapy of the subject. The ratio of Foxp3$^+$CD25$^+$ T-cells in CD4$^+$ T-cells, the ratio of an ICOS$^+$CD62L$^{low}$CD4$^+$ T-cell subpopulation in CD62L$^{low}$CD4$^+$ T-cells, the ratio of LAG-3$^+$CD62L$^{low}$CD4$^+$ T-cell subpopulation in CD62L$^{low}$CD4$^+$ T-cells, or the ratio of PD-1$^+$CD62L$^{low}$CD4$^+$ T-cell subpopulation in CD62L$^{low}$CD4$^+$ T-cells higher than an ineffective group threshold value can indicate that the subject is not a part of a response group. To determine whether a subject is a part of a response group, it is necessary to determine that the subject is not a part of an ineffective group. Such a determination of whether a subject is a part of an ineffective group can be achieved by a method disclosed herein.

Another embodiment of the present invention provides a method of identifying a response group (PR) and a stable group (SD) in a population of subjects determined not to be a part of an ineffective group using the aforementioned (X, Y). In a method of identifying a response group (PR) and stable group (SD), variables (Z, W) can be calculated, with an amount of an ICOS$^+$CD62L$^{low}$CD4$^+$ T-cell subpopulation as (Z) and a value selected from the group consisting of:
an amount of CD4$^+$CD25$^+$ T-cell subpopulation;
an amount of CD4$^+$Foxp3$^+$ T-cell subpopulation;
an amount of CD4$^+$Foxp3$^+$CD25$^+$ T-cell subpopulation;

an amount of CD62L$^{high}$CD25$^+$CD4$^+$ T-cell subpopulation;

an amount of CD45RA$^-$Foxp3$^+$CD4$^+$ T-cell subpopulation;

an amount of CCR4$^+$CD25$^+$CD4$^+$ T-cell subpopulation; and an amount of CD127$^+$CD25$^+$CD4$^+$ T-cell subpopulation;

as (W) to predict whether a subject is a part of the response group (PR) or stable group (SD). Typically, a method of identifying a response group (PR) and a stable group (SD) can determine the response group (PR) and the stable group (SD) using the amount of an ICOS$^+$CD62L$^{low}$CD4$^+$ T-cell subpopulation as (Z), the amount of a CD4$^+$Foxp3$^+$CD25$^+$ T-cell subpopulation as (W), and the value of W$^5$*Z as an indicator.

A threshold value can be determined by considering sensitivity and specificity. Sensitivity and specificity can be sensitivity and specificity for the detection of an ineffective group, detection of a response group, or detection of a stable group. In one embodiment, a threshold value at which sensitivity and specificity are both 100% can be set for the biomarker of the present invention. For this reason, an ineffective case can be selected very accurately, so that this is technically superior in a significant manner. When two or more indicators disclosed as a biomarker of the present invention are used, threshold values can be determined for each indicator and used and distinguished as a first threshold value, second threshold value, third threshold value, and fourth threshold value as needed.

A threshold value can be determined so that sensitivity for the detection of an ineffective group, detection of a response group, or detection of a stable group exceeds about 90%. In another embodiment, a threshold value can be determined so that the sensitivity for the detection of an ineffective group, detection of a response group, or detection of a stable group is about 100%. In still another embodiment, a threshold value can be determined so that specificity for the detection of an ineffective group, detection of a response group, or detection of a stable group exceeds about 90%. In still another embodiment, a threshold value can be determined so that specificity for the detection of an ineffective group, detection of a response group, or detection of a stable group is about 100%.

In one embodiment, the composition of T-cells of a subject is a composition of T-cells in a sample obtained from the subject. Preferably, a sample is a peripheral blood sample. The biomarker provided in the present invention can be measured using a peripheral blood sample, so that the biomarker has significant superiority in clinical applications, e.g., non-invasive, low-cost, and implementable over time.

In one embodiment, cancer immunotherapy comprises administration of an immune checkpoint inhibitor. In particular, the biomarker of the present invention can accurately predict a response to such cancer immunotherapy of a subject.

In one embodiment, an immune checkpoint inhibitor comprises a PD-1 inhibitor or a PD-L1 inhibitor. Examples of PD-1 inhibitors include, but are not limited to, anti-PD-1 antibodies that inhibit an interaction between PD-1 and PD-L1 (e.g., binding) such as anti-PD-1 antibodies nivolumab and pembrolizumab. Examples of PD-L1 inhibitors include, but are not limited to, anti-PD-L1 antibodies that inhibit an interaction between PD-1 and PD-L1 (e.g., binding) such as anti-PD-L1 antibodies durvalumab, atezolizumab, and avelumab.

Still another aspect of the present invention provides a method of predicting a response to cancer immunotherapy of a subject using the composition of T-cells of the subject to treat the subject with cancer. Alternatively, a method of treating cancer in a subject with a specific composition of T-cells or a composition therefor is provided. Cancer immunotherapy, especially immune checkpoint inhibition therapy is known to have a wide difference in responsiveness for each subject. Administration of cancer immunotherapy by selecting a subject using the biomarker of the present invention can significantly increase the probability of achieving a therapeutic effect such as tumor regression.

One embodiment of the present invention provides a method of treating a subject with cancer, comprising:

(1) determining a relative amount selected from the group consisting of:

a relative amount of a CD4$^+$ T-cell subpopulation correlated with a dendritic cell stimulation in an anti-tumor immune response;

a relative amount of a dendritic cell subpopulation correlated with a dendritic cell stimulation by a CD4$^+$ T-cell in an anti-tumor immune response; and a relative amount of a CD8$^+$ T-cell subpopulation correlated with a dendritic cell stimulation in an anti-tumor immune response, in CD4$^+$ T-cells in a sample derived from the subject; and (2) determining that the subject is not a part of an ineffective group with respect to a response to cancer immunotherapy if the relative amount is higher than a threshold value (ineffective group threshold value), and applying the cancer immunotherapy to the subject if the subject is determined to be not a part of an ineffective group.

Another embodiment of the present invention provides a method of treating a subject with cancer, comprising applying a cancer immunotherapy to a subject if the subject is determined to be not a part of an ineffective group by determining a relative amount selected from the group consisting of:

a relative amount of a CD4$^+$ T-cell subpopulation correlated with a dendritic cell stimulation in an anti-tumor immune response;

a relative amount of a dendritic cell subpopulation correlated with a dendritic cell stimulation by a CD4$^+$ T-cell in an anti-tumor immune response; and a relative amount of a CD8$^+$ T-cell subpopulation correlated with a dendritic cell stimulation in an anti-tumor immune response, in CD4$^+$ T-cells in a sample derived from the subject, and determining the relative amount to be higher than a threshold value (ineffective group threshold value).

In this method, the relative amount is selected from the group consisting of:

a ratio of a CD62L$^{low}$CD4$^+$ T-cell subpopulation in CD4$^+$ T-cells;

a ratio of a CCR7$^-$CD4$^+$ T-cell subpopulation in CD4$^+$ T-cells;

a ratio of a CD45RA$^-$CD4$^+$ T-cell subpopulation in CD4$^+$ T-cells;

a ratio of a CD45RO$^+$CD4$^+$ T-cell subpopulation in CD4$^+$ T-cells;

a ratio of an LAG-3$^+$CD62L$^{low}$CD4$^+$ T-cell subpopulation in CD62L$^{low}$CD4$^+$ T-cells;

a ratio of an ICOS$^+$CD62L$^{low}$CD4$^+$ T-cell subpopulation in CD62L$^{low}$CD4$^+$ T-cells;

a ratio of a CCR4$^+$CD25$^+$CD4$^+$ T-cell subpopulation in CD4$^+$ T-cells;

a ratio of a CD62L$^{high}$CD25$^+$CD4$^+$ T-cell subpopulation in CD4$^+$ T-cells;

a ratio of a CD127$^+$CD25$^+$CD4$^+$ T-cell subpopulation in CD4$^+$ T-cells;

a ratio of a CD45RA$^-$Foxp3$^+$CD4$^+$ T-cell subpopulation in CD4$^+$ T-cells, a ratio of a Foxp3$^+$CD25$^+$CD4$^+$ T-cell subpopulation in CD4$^+$ T-cells;

a ratio of an HLA-DR$^+$ dendritic cell subpopulation in dendritic cells;

a ratio of a CD80$^+$ dendritic cell subpopulation in dendritic cells;

a ratio of a CD86$^+$ dendritic cell subpopulation in dendritic cells;

a ratio of a PD-L1$^+$ dendritic cell subpopulation in dendritic cells;

a ratio of a CD62L$^{low}$CD8$^+$ T-cell subpopulation in CD8$^+$ T-cells;

a ratio of a CD137$^+$CD8$^+$ T-cell subpopulation in CD8$^+$ T-cells; and a ratio of a CD28$^+$CD62L$^{low}$CD8$^+$ T-cell subpopulation in CD62L$^{low}$CD8$^+$ T-cells.

Preferably, the relative amount is selected from the group consisting of:

a ratio of a CD62L$^{low}$CD4$^+$ T-cell subpopulation in CD4$^+$ T-cells;

a ratio of a CCR7 CD4$^+$ T-cell subpopulation in CD4$^+$ T-cells, a ratio of a CD45RA$^-$CD4$^+$ T-cell subpopulation in CD4$^+$ T-cells, a ratio of a CD45RO$^+$CD4$^+$ T-cell subpopulation in CD4$^+$ T-cells, a ratio of an LAG-3$^+$CD62L$^{low}$CD4$^+$ T-cell subpopulation in CD62L$^{low}$CD4$^+$ T-cells, a ratio of an ICOS$^+$CD62L$^{low}$CD4$^+$ T-cell subpopulation in CD62L$^{low}$CD4$^+$ T-cells, a ratio of an HLA-DR$^+$ dendritic cell subpopulation in dendritic cells, a ratio of a CD80$^+$ dendritic cell subpopulation in dendritic cells, a ratio of a CD86$^+$ dendritic cell subpopulation in dendritic cells, a ratio of a PD-L1$^+$ dendritic cell subpopulation in dendritic cells, a ratio of a CD62L$^{low}$CD8$^+$ T-cell subpopulation in CD8$^+$ T-cells, a ratio of a CD137$^+$CD8$^+$ T-cell subpopulation in CD8$^+$ T-cells, and a ratio of a CD28$^+$CD62L$^{low}$CD8$^+$ T-cell subpopulation in CD62L$^{low}$CD8$^+$ T-cells.

Another embodiment of the present invention provides a method of treating a subject with cancer, comprising: determining a ratio of Foxp3$^+$CD25$^+$ T-cells in CD4$^+$ T-cells in a sample derived from the subject; determining that the subject is not a part of an ineffective group with respect to a response to cancer immunotherapy if the ratio of Foxp3$^+$CD25$^+$ T-cells in CD4$^+$ T-cells is lower than a threshold value (ineffective group threshold value); and applying the cancer immunotherapy to the subject if the subject is determined to be not a part of an ineffective group. Another embodiment of the present invention provides a method of treating a subject with cancer, comprising applying the cancer immunotherapy to the subject who is determined not a part of an ineffective group with respect to a response to cancer immunotherapy by: determining a ratio of Foxp3$^+$CD25$^+$ T-cells in CD4$^+$ T-cells in a sample derived from the subject; and determining that the subject is not a part of an ineffective group with respect to a response to cancer immunotherapy if the ratio of Foxp3$^+$CD25$^+$ T-cells in CD4$^+$ T-cells is lower than a threshold value (ineffective group threshold value).

Another embodiment of the present invention provides a method of treating a subject with cancer, comprising:

(1) determining amounts (X, Y) selected from the group consisting of:

a relative amount of a CD4$^+$ T-cell subpopulation correlated with a dendritic cell stimulation in an anti-tumor immune response;

a relative of a dendritic cell subpopulation correlated with a dendritic cell stimulation by a CD4$^+$ T-cell in an anti-tumor immune response;

a relative of a CD8$^+$ T-cell subpopulation correlated with a dendritic cell stimulation in an anti-tumor immune response;

an amount of regulatory T-cells or a CD4$^+$ T-cell subpopulation correlated with regulatory T-cells; and an amount of an ICOS$^+$CD62L$^{low}$CD4$^+$ T-cell subpopulation;

(2) using a comparison of a relative value of X to Y with an ineffective group threshold value to determine whether the subject is a part of an ineffective group with respect to a response to cancer immunotherapy; and (3) applying the cancer immunotherapy to the subject if the subject is determined to be not a part of an ineffective group.

Another embodiment of the present invention provides a method of treating a subject with cancer, comprising applying the cancer immunotherapy to the subject who is determined not a part of an ineffective group with respect to a response to cancer immunotherapy by:

(1) determining amounts (X, Y) selected from the group consisting of:

a relative amount of a CD4$^+$ T-cell subpopulation correlated with a dendritic cell stimulation in an anti-tumor immune response;

a relative of a dendritic cell subpopulation correlated with a dendritic cell stimulation by a CD4$^+$ T-cell in an anti-tumor immune response;

a relative of a CD8$^+$ T-cell subpopulation correlated with a dendritic cell stimulation in an anti-tumor immune response;

an amount of regulatory T-cells or a CD4$^+$ T-cell subpopulation correlated with regulatory T-cells; and an amount of an ICOS$^+$CD62L$^{low}$CD4$^+$ T-cell subpopulation; and (2) using a comparison of a relative value of X to Y with an ineffective group threshold value to determine whether the subject is a part of an ineffective group with respect to a response to cancer immunotherapy.

For example, the aforementioned amounts (X) and (Y) are selected from the group consisting of:

an amount of a CD62L$^{low}$CD4$^+$ T-cell subpopulation;

an amount of a CCR7$^-$CD4$^+$ T-cell subpopulation;

an amount of an LAG-3$^+$CD62L$^{low}$CD4$^+$ T-cell subpopulation;

an amount of a CD45RA$^-$CD4$^+$ T-cell subpopulation;

an amount of a CD45RO$^+$CD4$^+$ T-cell subpopulation;

an amount of an HLA-DR$^+$ dendritic cell subpopulation;

an amount of a CD80$^+$ dendritic cell subpopulation;

an amount of a CD86$^+$ dendritic cell subpopulation;

an amount of a PD-L1$^+$ dendritic cell subpopulation;

an amount of a CD137$^+$CD8$^+$ T-cell subpopulation;

an amount of a CD62L$^{low}$CD8$^+$ T-cell subpopulation;

an amount of a CD28$^+$CD62L$^{low}$CD8$^+$ T-cell subpopulation;

an amount of a Foxp3$^+$CD25$^+$CD4$^+$ T-cell subpopulation;

an amount of a CD62L$^{high}$CD25$^+$CD4$^+$ T-cell subpopulation;
an amount of a CD45RA$^-$Foxp3$^+$CD4$^+$ T-cell subpopulation;
an amount of a CCR4$^+$CD25$^+$CD4$^+$ T-cell subpopulation; and
an amount of a CD127$^+$CD25$^+$CD4$^+$ T-cell subpopulation.

For example, the method of the present invention can use a value selected from the group consisting of:
an amount of a CD4$^+$ T-cell subpopulation correlated with a dendritic cell stimulation in an anti-tumor immune response;
an amount of a dendritic cell subpopulation correlated with a dendritic cell stimulation by a CD4$^+$ T-cell in an anti-tumor immune response; and
an amount of a CD8$^+$ T-cell subpopulation correlated with a dendritic cell stimulation in an anti-tumor immune response; as (X). The method of the present invention can also calculate variables (X, Y), with a value selected from the group consisting of:
an amount of a CD62L$^{low}$ CD4$^+$ T-cell subpopulation;
an amount of a CCR7$^-$CD4$^+$ T-cell subpopulation;
an amount of an LAG-3$^+$CD62L$^{low}$CD4$^+$ T-cell subpopulation;
an amount of an ICOS$^+$CD62L$^{low}$CD4$^+$ T-cell subpopulation;
an amount of a CD45RA$^-$CD4$^+$ T-cell subpopulation;
an amount of a CD45RO$^+$CD4$^+$ T-cell subpopulation;
an amount of an HLA-DR$^+$ dendritic cell subpopulation;
an amount of a CD80$^+$ dendritic cell subpopulation;
an amount of a CD86$^+$ dendritic cell subpopulation;
an amount of a PD-L1$^+$ dendritic cell subpopulation;
an amount of a CD62L$^{low}$CD8$^+$ T-cell subpopulation;
an amount of a CD137$^+$CD8$^+$ T-cell subpopulation; and
an amount of a CD28$^+$CD62L$^{low}$CD8$^+$ T-cell subpopulation; as (X).

For example, the method of the present invention can calculate variables (X, Y), with an amount of regulatory T-cells or a CD4$^+$ T-cell subpopulation correlated with regulatory T-cells as (Y). The method of the present invention can also calculate variables (X, Y), with a value selected from the group consisting of:
an amount of a CCR4$^+$CD25$^+$CD4$^+$ T-cell subpopulation;
an amount of a CD62L$^{high}$CD25$^+$CD4$^+$ T-cell subpopulation;
an amount of a CD127$^+$CD25$^+$CD4$^+$ T-cell subpopulation;
an amount of a CD45RA$^-$Foxp3$^+$CD4$^+$ T-cell subpopulation; and
an amount of a CD4$^+$Foxp3$^+$CD25$^+$ T-cell subpopulation; as (Y).

Another embodiment of the present invention provides a method of treating a subject with cancer, comprising: determining amounts (X, Y) selected from the group consisting of:
an amount of a CD4$^+$ T-cell subpopulation correlated with a dendritic cell stimulation in an anti-tumor immune response;
an amount of a dendritic cell subpopulation correlated with a dendritic cell stimulation by a CD4$^+$ T-cell in an anti-tumor immune response;
an amount of a CD8$^+$ T-cell subpopulation correlated with a dendritic cell stimulation in an anti-tumor immune response;
an amount of regulatory T-cells or a CD4$^+$ T-cell subpopulation correlated with regulatory T-cells; and an amount of an ICOS$^+$CD62L$^{low}$CD4$^+$ T-cell subpopulation;
using a comparison of a relative value of X to Y with a threshold value (ineffective group threshold value) to determine whether the subject is a part of an ineffective group with respect to a response to cancer immunotherapy; determining that the subject is a part of an effective group with respect to a response to cancer immunotherapy if it is determined that the subject is not a part of an ineffective group, and a ratio of Foxp3$^+$CD25$^+$ T-cells, a ratio of an ICOS$^+$CD62L$^{low}$CD4$^+$ T-cell subpopulation, a ratio of LAG-3$^+$CD62L$^{low}$CD4$^+$ T-cell subpopulation, or a ratio of PD-1$^+$ CD62L$^{low}$CD4$^+$ T-cell subpopulation is higher than a threshold value (effective group threshold value); and applying the cancer immunotherapy to the subject if the subject is determined to be a part of an effective group. Another embodiment of the present invention provides a method of treating a subject with cancer, comprising applying the cancer immunotherapy to the subject who is determined not a part of an ineffective group with respect to a response to cancer immunotherapy by:
determining amounts (X, Y) selected from the group consisting of:
an amount of a CD4$^+$ T-cell subpopulation correlated with a dendritic cell stimulation in an anti-tumor immune response;
an amount of a dendritic cell subpopulation correlated with a dendritic cell stimulation by a CD4$^+$ T-cell in an anti-tumor immune response;
an amount of a CD8$^+$ T-cell subpopulation correlated with a dendritic cell stimulation in an anti-tumor immune response;
an amount of regulatory T-cells or a CD4$^+$ T-cell subpopulation correlated with regulatory T-cells; and an amount of an ICOS$^+$CD62L$^{low}$CD4$^+$ T-cell subpopulation;
using a comparison of a relative value of X to Y with a threshold value (ineffective group threshold value) to determine whether the subject is a part of an ineffective group with respect to a response to cancer immunotherapy; determining that the subject is a part of an effective group with respect to a response to cancer immunotherapy if it is determined that the subject is not a part of an ineffective group, and a ratio of Foxp3$^+$CD25$^+$ T-cells, a ratio of an ICOS$^+$CD62L$^{low}$CD4$^+$ T-cell subpopulation, a ratio of LAG-3$^+$CD62L$^{low}$CD4$^+$ T-cell subpopulation, or a ratio of PD-1$^+$ CD62L$^{low}$CD4$^+$ T-cell subpopulation is higher than a threshold value (effective group threshold value).

For example, method of the present invention can use the value selected from the group consisting of:
an amount of a CD4$^+$ T-cell subpopulation correlated with a dendritic cell stimulation in an anti-tumor immune response;
an amount of a dendritic cell subpopulation correlated with a dendritic cell stimulation by a CD4$^+$ T-cell in an anti-tumor immune response; and
an amount of a CD8$^+$ T-cell subpopulation correlated with a dendritic cell stimulation in an anti-tumor immune response; as (X). The method of the present invention also can calculate variables (X, Y), with a value selected from the group consisting of:
an amount of a CD62L$^{low}$CD4$^+$ T-cell subpopulation;
an amount of a CCR7$^-$CD4$^+$ T-cell subpopulation;
an amount of an LAG-3$^+$CD62L$^{low}$CD4$^+$ T-cell subpopulation;
an amount of an ICOS$^+$CD62L$^{low}$CD4$^+$ T-cell subpopulation;

an amount of a CD45RA⁻CD4⁺ T-cell subpopulation;
an amount of a CD45RO⁺CD4⁺ T-cell subpopulation;
an amount of an HLA-DR⁺ dendritic cell subpopulation;
an amount of a CD80⁺ dendritic cell subpopulation;
an amount of a CD86⁺ dendritic cell subpopulation;
an amount of a PD-L1⁺ dendritic cell subpopulation;
an amount of a CD62L$^{low}$CD8⁺ T-cell subpopulation; and
an amount of a CD137⁺CD8⁺ T-cell subpopulation;
an amount of a CD28⁺CD62L$^{low}$CD8⁺ T-cell subpopulation; as (X).

For example, the method of the present invention can calculate variables (X, Y), with an amount of a regulatory T-cell subpopulation or a CD4⁺ T-cell subpopulation correlated with regulatory T-cells as (Y). The method of the present invention can also calculate variables (X, Y), with a value selected from the group consisting of:

an amount of a CCR4⁺CD25⁺CD4⁺ T-cell subpopulation;
an amount of a CD62L$^{high}$CD25⁺CD4⁺ T-cell subpopulation;
an amount of a CD127⁺CD25⁺CD4⁺ T-cell subpopulation;
an amount of a CD45RA⁻Foxp3⁺CD4⁺ T-cell subpopulation; and
an amount of a CD4⁺Foxp3⁺CD25⁺ T-cell subpopulation; as (Y).

Another aspect of the present invention provides a method of identifying a response group (PR) and a stable group (SD) in a population of subjects determined to be not a part of an ineffective group using the aforementioned (X, Y). A method of identifying a response group (PR) and a stable group (SD) can calculate variables (Z, W), with an amount of an ICOS⁺CD62L$^{low}$CD4⁺ T-cell subpopulation as (Z) and a value selected from the group consisting of:

an amount of a CD4⁺CD25⁺ T-cell subpopulation;
an amount of a CD4⁺Foxp3+ T-cell subpopulation;
an amount of a CD4⁺Foxp3⁺CD25⁺ T-cell subpopulation;
an amount of a CD62L$^{high}$CD25⁺CD4⁺ T-cell subpopulation;
an amount of a CD45RA⁻Foxp3⁺CD4⁺ T-cell subpopulation;
an amount of a CCR4⁺CD25⁺CD4⁺ T-cell subpopulation; and
an amount of a CD127⁺CD25⁺CD4⁺ T-cell subpopulation; as (W) to predict whether a subject is a part of the response group (PR) or the stable group (SD).

Still another aspect of the present invention provides a kit for predicting a response to cancer immunotherapy of a subject comprising an agent for detecting one or more cell surface markers selected from CD4, CD25, CD62L, Foxp3, and the like, such as a combination of markers selected from the group consisting of:

*a combination of CD4 and CD62L;
*a combination of CD4, CD45RA, and CCR7;
*a combination of CD4, CD45RO, and CCR7;
*a combination of CD4, CD62L, and LAG-3;
*a combination of CD4, CD62L, and ICOS;
*a combination of CD4, CD62L, and CD25;
*a combination of CD4, CD127, and CD25;
*a combination of CD4, CD45RA, and Foxp3;
*a combination of CD4, CD45RO, and Foxp3;
*a combination of CD4, CD25, and Foxp3;
*a combination of CD11c, CD141, and HLA-DR;
*a combination of CD11c, CD141, and CD80;
*a combination of CD11c, CD123, and HLA-DR;
*a combination of CD11c, CD123, and CD80;
*a combination of CD8 and CD62L;
*a combination of CD8 and CD137; and
*a combination of CD28, CD62L and CD8. Preferably, the kit comprises an agent for detecting each of CD4 and CD62L. A combination of such detection agents can be used in determining the composition of T-cells of a subject. Such a kit can be used in measuring the ratio of a specific T-cell subpopulation as a novel biomarker disclosed herein in a subject.

One embodiment of the present invention is a kit comprising an agent for detecting a cell surface marker for predicting a response to cancer immunotherapy of a subject. The inventors discovered that these cell surface markers expressed by a T-cell of a subject are related to responsiveness to cancer immunotherapy of a subject. It is understood that a kit comprising an agent for detecting such cell surface markers are useful in predicting responsiveness to cancer immunotherapy in view of the above. A kit preferably comprises an agent for detecting CD4 and CD62L. A kit more preferably comprises an agent for detecting CD4, CD25, CD62L, and Foxp3. In one embodiment, a detection agent is an antibody. Preferably, an antibody facilitates the detection of a suitably labeled marker.

Another aspect of the present invention is a composition for treating cancer in a subject, comprising an immune checkpoint inhibitor.

One embodiment of the present invention is a composition for treating cancer in a subject, comprising an immune checkpoint inhibitor, characterized in that the subject has a relative amount selected from the group consisting of:

a relative amount of a CD4⁺ T-cell subpopulation correlated with a dendritic cell stimulation in an anti-tumor immune response;

a relative amount of a dendritic cell subpopulation correlated with a dendritic cell stimulation by a CD4⁺ T-cell in an anti-tumor immune response; and a relative amount of a CD8⁺ T-cell subpopulation correlated with a dendritic cell stimulation in an anti-tumor immune response;

wherein the relative amount is equal to or greater than a threshold value (ineffective group threshold value).

For example, the relative amount is typically selected from the group consisting of:

a ratio of a CD62L$^{low}$CD4⁺ T-cell subpopulation in CD4⁺ T-cells;
a ratio of a CCR7⁻CD4⁺ T-cell subpopulation in CD4⁺ T-cells;
a ratio of a LAG-3⁺CD62L$^{low}$CD4⁺ T-cell subpopulation in CD62L$^{low}$CD4⁺ T-cells;
a ratio of an ICOS⁺CD62L$^{low}$CD4⁺ T-cell subpopulation in CD62L$^{low}$CD4⁺ T-cells;
a ratio of a CD62L$^{high}$CD25⁺CD4⁺ T-cell subpopulation in CD4⁺ T-cells;
a ratio of a CD127⁺CD25⁺CD4⁺ T-cell subpopulation in CD4⁺ T-cells;
a ratio of a CD45RA⁻Foxp3⁺CD4⁺ T-cell subpopulation in CD4⁺ T-cells;
a ratio of a Foxp3⁺CD25⁺CD4⁺ T-cell subpopulation in CD4⁺ T-cells;
a ratio of an HLA-DR⁺ dendritic cell subpopulation in dendritic cells;
a ratio of a CD80⁺ dendritic cell subpopulation in dendritic cells;
a ratio of a CD86⁺ dendritic cell subpopulation in dendritic cells;
a ratio of a PD-L1⁺ dendritic cell subpopulation in dendritic cells;

a ratio of a CD62L$^{low}$CD8$^+$ T-cell subpopulation in CD8$^+$ T-cells; and a ratio of a CD137$^+$CD8$^+$ T-cell subpopulation in CD8$^+$ T-cells; and a ratio of a CD28$^+$CD62L$^{low}$CD8$^+$ T-cell subpopulation in CD62L$^{low}$CD8$^+$ T-cells.

Still another embodiment of the present invention is a composition for treating cancer in a subject, comprising an immune checkpoint inhibitor, characterized in that the subject is a subject selected by comparison of a threshold value (ineffective group threshold value) and a relative value of X to Y with amounts (X, Y) selected from the group consisting of:

an amount of a CD4$^+$ T-cell subpopulation correlated with a dendritic cell stimulation in an anti-tumor immune response;

an amount of a dendritic cell subpopulation correlated with a dendritic cell stimulation in an anti-tumor immune response; and an amount of a CD8$^+$ T-cell subpopulation correlated with a dendritic cell stimulation in an anti-tumor immune response;

an amount of regulatory T-cells or a CD4$^+$ T-cell subpopulation correlated with regulatory T-cells; and an ICOS$^+$CD62L$^{low}$CD4$^+$ T-cell subpopulation;

in a sample derived from the subject. The amounts (X, Y) are typically selected from the group consisting of:

an amount of a CD62L$^{low}$CD4$^+$ T-cell subpopulation;
an amount of a CCR7$^-$CD4$^+$ T-cell subpopulation;
an amount of a LAG-3$^+$CD62L$^{low}$CD4$^+$ T-cell subpopulation;
an amount of an ICOS$^+$CD62L$^{low}$CD4$^+$ T-cell subpopulation;
an amount of a CCR4$^+$CD25$^+$CD4$^+$ T-cell subpopulation;
an amount of a CD45RA$^-$CD4$^+$ T-cell subpopulation;
an amount of a CD45RO$^+$CD4$^+$ T-cell subpopulation;
an amount of a CD62L$^{high}$CD25$^+$CD4$^+$ T-cell subpopulation;
an amount of a CD127$^+$CD25$^+$CD4$^+$ T-cell subpopulation;
an amount of a CD45RA$^-$Foxp3$^+$CD4$^+$ T-cell subpopulation;
an amount of a Foxp3$^+$CD25$^+$CD4$^+$ T-cell subpopulation;
an amount of an HLA-DR$^+$ dendritic cell subpopulation;
an amount of a CD80$^+$ dendritic cell subpopulation;
an amount of a CD86$^+$ dendritic cell subpopulation;
an amount of a PD-L1$^+$ dendritic cell subpopulation;
an amount of a CD62L$^{low}$CD8$^+$ T-cell subpopulation;
an amount of a CD137$^+$CD8$^+$ T-cell subpopulation; and
an amount of a CD28$^+$CD62L$^{low}$CD8$^+$ T-cell subpopulation.

For example, the method of the present invention can use a value selected from the group consisting of:

an amount of a CD4$^+$ T-cell subpopulation correlated with a dendritic cell stimulation in an anti-tumor immune response;

an amount of a dendritic cell subpopulation correlated with a dendritic cell stimulation by a CD4$^+$ T-cell in an anti-tumor immune response; and an amount of a CD8$^+$ T-cell subpopulation correlated with a dendritic cell stimulation in an anti-tumor immune response; as (X). The method of the present invention can also calculate variables (X, Y), with a value selected from the group consisting of:

an amount of a CD62L$^{low}$CD4$^+$ T-cell subpopulation;
an amount of a CCR7$^-$CD4$^+$ T-cell subpopulation;
an amount of a LAG-3$^+$CD62L$^{low}$CD4$^+$ T-cell subpopulation;
an amount of an ICOS$^+$CD62L$^{low}$CD4$^+$ T-cell subpopulation;
an amount of a CD45RA$^-$CD4$^+$ T-cell subpopulation;
an amount of a CD45RO$^+$CD4$^+$ T-cell subpopulation;
an amount of an HLA-DR$^+$ dendritic cell subpopulation;
an amount of a CD80$^+$ dendritic cell subpopulation;
an amount of a CD86$^+$ dendritic cell subpopulation;
an amount of a PD-L1$^+$ dendritic cell subpopulation;
an amount of a CD62L$^{low}$CD8$^+$ T-cell subpopulation;
an amount of a CD137$^+$CD8$^+$ T-cell subpopulation; and
an amount of a CD28$^+$CD62L$^{low}$CD8$^+$ T-cell subpopulation; as (X).

For example, method of the present invention can calculate variables (X, Y), with the amount of regulatory T-cells or a CD4$^+$ T-cell subpopulation correlated with regulatory T-cells as (Y). The method of the present invention can also calculate variables (X, Y), with a value selected from the group consisting of:

an amount of a CCR4$^+$CD25$^+$CD4$^+$ T-cell subpopulation;
an amount of a CD62L$^{high}$CD25$^+$CD4$^+$ T-cell subpopulation;
an amount of a CD127$^+$CD25$^+$CD4$^+$ T-cell subpopulation;
an amount of a CD45RA$^-$Foxp3$^+$CD4$^+$ T-cell subpopulation; and an amount of a CD4$^+$Foxp3$^+$CD25$^+$ T-cell subpopulation; as (Y).

For example, the method of the present invention can use a comparison of a relative value of X to Y with a threshold value (ineffective group threshold value), comprising measuring the amount of CD4$^+$CD62L$^{low}$ T-cells (X) and measuring the amount of CD4$^+$Foxp3$^+$CD25$^+$ T-cells (Y) as an indicator for predicting that the subject is not a part of an ineffective group with respect to the cancer immunotherapy. The amount or ratio of regulatory T-cells or a CD4$^+$ T-cell subpopulation correlated with regulatory T-cells can be used as (Y).

Still another embodiment of the present invention is a composition for treating cancer in a subject, comprising an immune checkpoint inhibitor, characterized in that the subject is a subject selected by comparison of a threshold value (ineffective group threshold value) with a relative value of amounts (X, Y) selected from the group consisting of:

an amount of a CD4$^+$ T-cell subpopulation correlated with a dendritic cell stimulation in an anti-tumor immune response;

an amount of a dendritic cell subpopulation correlated with a dendritic cell stimulation by a CD4$^+$ T-cell in an anti-tumor immune response;

an amount of a CD8$^+$ T-cell subpopulation correlated with a dendritic cell stimulation in an anti-tumor immune response;

an amount of regulatory T-cells or a CD4$^+$ T-cell subpopulation correlated with regulatory T-cells; and an amount of an ICOS$^+$CD62L$^{low}$CD4$^+$ T-cell subpopulation, in a sample derived from the subject, and having a ratio of a Foxp3$^+$CD25$^+$ T-cell subpopulation in CD4$^+$ T-cells or a ratio of an ICOS$^+$CD62L$^{low}$CD4$^+$ T-cell subpopulation in CD62L$^{low}$CD4$^+$ T-cells equal to or greater than a threshold value (effective group threshold value). The amounts (X) and (Y) are typically selected from the group consisting of:

an amount of a CD62L$^{low}$CD4$^+$ T-cell subpopulation;
an amount of a CCR7$^-$CD4$^+$ T-cell subpopulation;
an amount of a LAG-3$^+$CD62L$^{low}$CD4$^+$ T-cell subpopulation;

an amount of an ICOS$^+$CD62L$^{low}$CD4$^+$ T-cell subpopulation;
an amount of a CCR4$^+$CD25$^+$CD4$^+$ T-cell subpopulation;
an amount of a CD45RA$^-$CD4$^+$ T-cell subpopulation;
an amount of a CD45RO$^+$CD4$^+$ T-cell subpopulation;
an amount of a CD62L$^{high}$CD25$^+$CD4$^+$ T-cell subpopulation;
an amount of a CD127$^+$CD25$^+$CD4$^+$ T-cell subpopulation;
an amount of a CD45RA$^-$Foxp3$^+$CD4$^+$ T-cell subpopulation;
an amount of a Foxp3$^+$CD25$^+$CD4$^+$ T-cell subpopulation;
an amount of an HLA-DR$^+$ dendritic cell subpopulation;
an amount of a CD80$^+$ dendritic cell subpopulation;
an amount of a CD86$^+$ dendritic cell subpopulation;
an amount of a PD-L1$^+$ dendritic cell subpopulation;
an amount of a CD62L$^{low}$CD8$^+$ T-cell subpopulation;
an amount of a CD137$^+$CD8$^+$ T-cell subpopulation; and
an amount of a CD28$^+$CD62L$^{low}$CD8$^+$ T-cell subpopulation.

For example, the target of administration of the composition of the present invention can be a subject characterized by variables (X, Y), with a value selected from the group consisting of:
an amount of a CD4$^+$ T-cell subpopulation correlated with a dendritic cell stimulation in an anti-tumor immune response;
an amount of a dendritic cell subpopulation correlated with a dendritic cell stimulation by a CD4$^+$ T-cell in an anti-tumor immune response; and
an amount of a CD8$^+$ T-cell subpopulation correlated with a dendritic cell stimulation in an anti-tumor immune response; as (X). The method of the present invention can also calculate variables (X, Y), with a value selected from the group consisting of:
an amount of a CD62L$^{low}$CD4$^+$ T-cell subpopulation;
an amount of a CCR7$^-$CD4$^+$ T-cell subpopulation;
an amount of a LAG-3$^+$CD62L$^{low}$CD4$^+$ T-cell subpopulation;
an amount of an ICOS$^+$CD62L$^{low}$CD4$^+$ T-cell subpopulation;
an amount of a CD45RA$^-$CD4$^+$ T-cell subpopulation;
an amount of a CD45RO$^+$CD4$^+$ T-cell subpopulation;
an amount of an HLA-DR$^+$ dendritic cell subpopulation;
an amount of a CD80$^+$ dendritic cell subpopulation;
an amount of a CD86$^+$ dendritic cell subpopulation;
an amount of a PD-L1$^+$ dendritic cell subpopulation;
an amount of a CD62L$^{low}$CD8$^+$ T-cell subpopulation;
an amount of a CD137$^+$CD8$^+$ T-cell subpopulation; and
an amount of a CD28$^+$CD62L$^{low}$CD8$^+$ T-cell subpopulation; as (X) to target administration to a subject characterized by variables (X, Y).

For example, for the composition of the present invention, variables (X, Y) can be calculated, with an amount of regulatory T-cells or a CD4$^+$ T-cell subpopulation correlated with regulatory T-cells as (Y). The method of the present invention can also calculate variables (X, Y), with a value selected from the group consisting of:
an amount of a CCR4$^+$CD25$^+$CD4$^+$ T-cell subpopulation;
an amount of a CD62L$^{high}$CD25$^+$CD4$^+$ T-cell subpopulation;
an amount of a CD127$^+$CD25$^+$CD4$^+$ T-cell subpopulation;
an amount of a CD45RA$^-$Foxp3$^+$CD4$^+$ T-cell subpopulation; and
an amount of a CD4$^+$Foxp3$^+$CD25$^+$ T-cell subpopulation; as (Y) to target administration to a subject characterized by variables (X, Y).

For example, a subject predicted to be not a part of an ineffective group with respect to cancer immunotherapy can be targeted as the target of administrating the composition of the present invention by comparing a relative value of X to Y with a threshold value (ineffective group threshold value) from the amount of CD4$^+$CD62$^{low}$ T-cells (X) and the amount of CD4$^+$Foxp3$^+$CD25$^+$ T-cells (Y). The amount or ratio of regulatory T-cells or a CD4$^+$ T-cell subpopulation correlated with regulatory T-cells can be used as (Y). The composition of the present invention can be used in combination with any other agents.

In one embodiment, a composition comprises a PD-1 inhibitor. Examples of PD-1 inhibitors include anti-PD-1 antibodies that inhibit a binding between PD-L1 and PD-1, such as nivolumab or pembrolizumab. In another embodiment, the composition comprises a PD-L1 inhibitor. Examples of PD-L1 inhibitors include anti-PD-L1 antibodies that inhibit a binding between PD-L1 and PD-1, such as durvalumab, atezolizumab, and avelumab. Compositions comprising such immune checkpoint inhibitors are understood as attaining a therapeutic effect at an especially high probability when administered to a subject selected using the biomarker of the present invention.

Another aspect of the present invention provides a method of improving or maintaining responsiveness to cancer immunotherapy of a subject. It was discovered that cells selected from the group consisting of:
CD62L$^{low}$CD4$^+$ T-cells;
CCR7$^-$CD4$^+$ T-cells;
LAG-3$^+$CD62L$^{low}$CD4$^+$ T-cells;
ICOS$^+$CD62L$^{low}$CD4$^+$ T-cells;
CCR4$^+$CD25$^+$CD4$^+$ T-cells;
CD45RA$^-$CD4$^+$ T-cells;
CD45RO$^+$CD4$^+$ T-cells;
CD62L$^{high}$CD25$^+$CD4$^+$ T-cells;
CD127$^+$CD25$^+$CD4$^+$ T-cells;
CD45RA$^-$Foxp3$^+$CD4$^+$ T-cells;
Foxp3$^+$CD25$^+$CD4$^+$ T-cells;
HLA-DR$^+$ dendritic cells;
CD80$^+$ dendritic cells;
CD86$^+$ dendritic cells;
PD-L1$^+$ dendritic cells;
CD62L$^{low}$CD8$^+$ T-cells;
CD137$^+$CD8$^+$ T-cells; and
CD28$^+$CD62L$^{low}$CD8$^+$ T-cells;
are important to the response of a subject to cancer immunotherapy. It is understood that use of such T-cells can improve or maintain the responsiveness to cancer immunotherapy of a subject. One embodiment of the present invention is a composition comprising a CD62L$^{low}$CD4$^+$ T-cell. A CD62L$^{low}$CD4$^+$ T-cell or a composition comprising the same is useful for treating or preventing cancer and can be used in combination with cancer immunotherapy. In a still another embodiment, the composition may comprise a CD62L$^{low}$CD8$^+$ T-cell in addition to CD62L$^{low}$CD4$^+$ T-cell or the like.

One embodiment of the present invention provides a method of making cancer immunotherapy effective in a subject for whom the cancer immunotherapy is predicted to be ineffective by using a cell selected from the group consisting of:
CD62L$^{low}$CD4$^+$ T-cells;
CCR7$^-$CD4$^+$ T-cells;
LAG-3$^+$CD62L$^{low}$CD4$^+$ T-cells;

ICOS⁺CD62L$^{low}$CD4⁺ T-cells;
CCR4⁺CD25⁺CD4⁺ T-cells;
CD45RA⁻CD4⁺ T-cells;
CD45RO⁺CD4⁺ T-cells;
CD62L$^{high}$CD25⁺CD4⁺ T-cells;
CD127⁺CD25⁺CD4⁺ T-cells;
CD45RA Foxp3⁺CD4⁺ T-cells;
Foxp3⁺CD25⁺CD4⁺ T-cells;
HLA-DR⁺ dendritic cells;
CD80⁺ dendritic cells;
CD86⁺ dendritic cells;
PD-L1⁺ dendritic cells;
CD62L$^{low}$CD8⁺ T-cells;
CD137⁺CD8⁺ T-cells; and
CD28⁺CD62L$^{low}$CD8⁺ T-cells;

or a composition therefor. Another embodiment of the present invention provides a method for sustaining an effect of cancer immunotherapy by using, for example, CD62L$^{low}$CD4⁺ T-cells or a composition thereof. The results of the inventors' study, which elucidated that CD62L$^{low}$CD4⁺ T-cells of peripheral blood play the role of an accelerator for an anti-tumor immune response in cancer immunotherapy (especially anti-PD-1 antibody therapy and/or anti-PD-L1 antibody therapy), is a novel finding, which provides a new and revolutionary approach to cancer therapy. The inventors have also discovered that a cell selected from the group consisting of:

CCR7⁻CD4⁺ T-cells;
LAG-3⁺CD62L$^{low}$CD4⁺ T-cells;
ICOS⁺CD62L$^{low}$CD4⁺ T-cells;
CCR4⁺CD25⁺CD4⁺ T-cells;
CD45RA⁻CD4⁺ T-cells;
CD45RO⁺CD4⁺ T-cells;
CD62L$^{high}$CD25⁺CD4⁺ T-cells;
CD127⁺CD25⁺CD4⁺ T-cells;
CD45RA⁻Foxp3⁺CD4⁺ T-cells;
Foxp3⁺CD25⁺CD4⁺ T-cells;
HLA-DR⁺ dendritic cells;
CD80⁺ dendritic cells;
CD86⁺ dendritic cells;
PD-L1⁺ dendritic cells;
CD62L$^{low}$CD8⁺ T-cells;
CD137⁺CD8⁺ T-cells; and
CD28⁺CD62L$^{low}$CD8⁺ T-cells also promote anti-tumor immune responses as in the CD62L$^{low}$CD4⁺ T-cell disclosed above. In still another embodiment of the present invention, CD62L$^{low}$CD8⁺ T-cells may be used in addition to CD62L$^{low}$CD4⁺ T-cells.

Some embodiments of the present invention provide a method of refining or purifying CD62L$^{low}$CD4⁺ T-cells or a method of manufacturing a composition comprising CD62L$^{low}$CD4⁺ T-cells. In some embodiments, CD62L$^{low}$CD4⁺ T cells are isolated from a human derived sample. Some embodiments provide a method of preparing CD62L$^{low}$CD4⁺ T cells that have been isolated from a subject for infusion into the subject and a method of infusing such cells into the subject. One embodiment of the present invention is a composition comprising a CD62L$^{low}$CD4⁺ T-cell, which is from a subject to whom the composition is administered. A still another aspect of the present invention provides a method of refining or purifying CD62L$^{low}$CD8⁺ T-cells or a method of manufacturing a composition comprising CD62L$^{low}$CD8⁺ T-cells. Using the same principle, the present invention similarly prepares a cell selected from the group consisting of:

CCR7⁻CD4⁺ T-cells;
LAG-3⁺CD62L$^{low}$CD4⁺ T-cells;
ICOS⁺CD62L$^{low}$CD4⁺ T-cells;
CCR4⁺CD25⁺CD4⁺ T-cells;
CD45RA⁻CD4⁺ T-cells;
CD45RO⁺CD4⁺ T-cells;
CD62L$^{high}$CD25⁺CD4⁺ T-cells;
CD127⁺CD25⁺CD4⁺ T-cells;
CD45RA⁻Foxp3⁺CD4⁺ T-cells;
Foxp3⁺CD25⁺CD4⁺ T-cells;
HLA-DR⁺ dendritic cells;
CD80⁺ dendritic cells;
CD86⁺ dendritic cells;
PD-L1⁺ dendritic cells;
CD62L$^{low}$CD8⁺ T-cells;
CD137⁺CD8⁺ T-cells; and
CD28⁺CD62L$^{low}$CD8⁺ T-cells.

A method of manufacturing a composition comprising CD62L$^{low}$CD4⁺ T-cells can comprise purifying CD62L$^{low}$CD4⁺ T-cells from a T-cell population derived from a human. The purifying may comprise removing a CD62L high expression cell from the T-cell population (negative selection) Purification of CD62L$^{low}$CD4⁺ T-cells by negative selection using an antibody and/or magnetic beads and/or affinity column, or the like is preferable because impurities such as an antibody or magnetic beads do not remain on a cell to be used. The present invention also provides a method of manufacturing a composition comprising CD62L$^{low}$CD8⁺ T-cells.

One embodiment of the present invention is a kit comprising a substance, which specifically binds to CD62L, for purifying CD62L$^{low}$CD4⁺ T-cells. Examples of a substance which specifically binds to CD62L include, but are not limited to, antibodies that are specific to CD62L.

(Biomarkers of the Present Invention)

The biomarker of the present invention is understood to evaluate the overall balance of anti-tumor immune responses, including CD4⁺ T-cells, dendritic cells, and/or CD8+ T-cells to evaluate the overall tumor immunity itself. For this reason, the method of the present invention can be considered effective against a wide range of cancers and tumors. The present invention evaluates the overall anti-tumor immune responses, so that the present invention is also expected to be effective for not only an immune checkpoint inhibitor against PD-1/PD-L1, but also anticancer therapy which acts on other immune checkpoints.

The present invention can also use a marker, which is indicative of an effector T-cell, such as CCR7-, instead of or in addition to CD62L$^{low}$. Alternatively, CD45RA- and/or CD45RO+ can be used. For example, the ratio of a CD45RA⁻CD4⁺ T-cell subpopulation in CD4⁺ T-cells and/or the ratio of CD45RO⁺CD4⁺ T-cell subpopulation in CD4⁺ T-cells can also be used. It was revealed that expression of LAG3 and ICOS can also be used (added or substituted) in a similar manner to CD62L$^{low}$. It was similarly discovered that CCR4 expression can also be used (added or substituted) in a similar manner to CD62L$^{low}$.

Instead of (or in addition to) using CD4⁺ T-cells (CD62L$^{low}$CD4⁺ T-cells) which were used in the Examples, the number/ratio of cells expressing HLA-DR and/or CD80 and/or CD86 in a myeloid dendritic cell (mDC) and/or plasmacytoid dendritic cell (pDC) population can also be used as an indicator. PD-L1 on dendritic cells is also understood to be available as the marker of the present invention.

Further, instead (or in addition to) of using CD4⁺ T-cells (CD62L$^{low}$CD4⁺ T-cells) which were used in the Examples, the number/ratio of cells expressing 4-1BB in CD8+ T-cells can also be used as an indicator.

(Mechanism of the Present Invention)

Although not wishing to be bound by any theory, the anti-tumor immune response phenomenon at a local tumor proposed by the inventors is schematically shown in FIG. 21. FIG. 21 shows cells that can be observed in peripheral blood, i.e., $CD62L^{low}CD4^+$ T-cells, myeloid dendritic cells (mDC), plasmacytoid dendritic cells (pDC), and $CD62L^{low}CD8^+$ T-cells, and marker molecules expressed in these cells, i.e., LAG-3, ICOS, HLA-DR, CD80, and CD137. PD-L1 is expressed in dendritic cells, and PD-1 is expressed in $CD62L^{low}CD4^+$ T-cells and $CD62L^{low}CD8^+$ T-cells.

The composition of T-cells is considered important in anti-tumor immune responses. For example, a stimulation of a dendritic cell by a $CD62L^{low}CD4^+$ T-cell is important. If there are insufficient $CD62L^{low}CD4^+$ T-cells (e.g., the balance of effector T-cells and naive T-cells leans towards naive T-cells), dendritic cells cannot be sufficiently stimulated even with administration of an immune checkpoint inhibitor. As a result, an anti-tumor immune response cannot be sufficient. For this reason, the ratio of $CD62L^{low}CD4^+$ T-cells in $CD4^+$ T-cells is an indicator for predicting an anti-tumor effect due to an immune checkpoint inhibitor. As with CD62L, the ratio of $CD45RA^-CCR7^-$ T-cells in $CD4^+$ T-cells also indicates the balance of effector T-cells and naive T-cells, so that such a ratio can be used as an indicator of the present invention.

Dendritic cells are stimulated by $CD4^+$ T-cells via HLA-DR. Thus, with a decrease in the ratio of HLA-DR+ cells in dendritic cells, the dendritic cells cannot be sufficiently stimulated even with administration of an immune checkpoint inhibitor. As a result, anti-tumor immune responses cannot be sufficient. For this reason, the ratio of HLA-DR+ cells in dendritic cells can also be an indicator for predicting an anti-tumor effect due to an immune checkpoint inhibitor.

Dendritic cells which have been stimulated by $CD4^+$ T-cells stimulate $CD8^+$ T-cells, and stimulated $CD8^+$ T-cells ultimately exert anti-tumor activity. $CD8^+$ T-cells are stimulated by dendritic cells via CD80/CD86 expressed on dendritic cells and CD137 on $CD8^+$ T-cells. Thus, both the ratio of CD80+ cells in dendritic cells and the ratio of CD137+ cells in $CD8^+$ T-cells can be an indicator for predicting an anti-tumor effect due to an immune checkpoint inhibitor.

In addition to the biomarkers revealed from the mechanism disclosed above, LAG-3, ICOS, and CCR4 in $CD4^+$ T-cells were also found to be an indicator for predicting an anti-tumor effect due to an immune checkpoint inhibitor as disclosed in the Examples.

For example, the present invention provides the following items.

(Item 1)

A method of using a relative amount of a $CD4^+$ T-cell subpopulation correlated with a dendritic cell stimulation in an anti-tumor immune response as an indicator for predicting a response to cancer immunotherapy of a subject, comprising determining the relative amount of the $CD4^+$ T-cell subpopulation in a sample derived from the subject, the relative amount higher than an ineffective group threshold value indicating that the subject is not a part of an ineffective group to the cancer immunotherapy.

(Item 2)

The method of item 1, wherein the relative amount of the $CD4^+$ T-cell subpopulation is selected from the group consisting of:

a ratio of a $CD62L^{low}CD4^+$ T-cell subpopulation in $CD4^+$ T-cells;

a ratio of a $CCR7^-CD4^+$ T-cell subpopulation in $CD4^+$ T-cells;

a ratio of a $LAG-3^+CD62L^{low}CD4^+$ T-cell subpopulation in $CD62L^{low}CD4^+$ T-cells;

a ratio of an $ICOS^+CD62L^{low}CD4^+$ T-cell subpopulation in $CD62L^{low}CD4^+$ T-cells;

a ratio of a $CCR4^+CD25^+CD4^+$ T-cell subpopulation in $CD4^+$ T-cells;

a ratio of a $CD62L^{high}CD25^+CD4^+$ T-cell subpopulation in $CD4^+$ T-cells;

a ratio of a $CD127^+CD25^+CD4^+$ T-cell subpopulation in $CD4^+$ T-cells;

a ratio of a $CD45RA^-Foxp3^+CD4^+$ T-cell subpopulation in $CD4^+$ T-cells; and a ratio of a $Foxp3^+CD25^+CD4^+$ T-cell subpopulation in $CD4^+$ T-cells.

(Item 3)

A method of using a ratio of $CD62L^{low}$ T-cells in $CD4^+$ T-cells of a subject as an indicator for predicting a response to cancer immunotherapy of the subject, comprising determining the ratio of $CD62L^{low}$ T-cells in the $CD4^+$ T-cells in a sample derived from the subject, the ratio higher than an ineffective group threshold value indicating that the subject is not a part of an ineffective group to the cancer immunotherapy.

(Item 4)

A method of using a relative amount of a dendritic cell subpopulation correlated with a dendritic cell stimulation in an anti-tumor immune response as an indicator for predicting a response to cancer immunotherapy of a subject, comprising determining a ratio of the dendritic cell subpopulation in dendritic cells in a sample derived from the subject, the ratio higher than an ineffective group threshold value indicating that the subject is not a part of an ineffective group to the cancer immunotherapy.

(Item 5)

The method of item 4, wherein the dendritic cell subpopulation is selected from the group consisting of: an $HLA-DR^+$ dendritic cell subpopulation; a $CD80^+$ dendritic cell subpopulation; a $CD86^+$ dendritic cell subpopulation; and $PD-L1^+$ dendritic cell subpopulation.

(Item 6)

A method of using a relative amount of a $CD8^+$ T-cell subpopulation correlated with a dendritic cell stimulation in an anti-tumor immune response as an indicator for predicting a response to cancer immunotherapy of a subject, comprising determining a ratio of the $CD8^+$ T-cell subpopulation in $CD8^+$ T-cells in a sample derived from the subject, the ratio higher than an ineffective group threshold value indicating that the subject is not a part of an ineffective group to the cancer immunotherapy.

(Item 7)

The method of item 6, wherein the $CD8^+$ T-cell subpopulation is a $CD62L^{low}CD8^+$ T-cell subpopulation, a $CD137^+CD8^+$ T-cell subpopulation, or a $CD28^+CD62L^{low}CD8^+$ T-cell subpopulation.

(Item 8)

A method of using a relative value of amounts (X, Y) selected from the group consisting of:

an amount of a $CD4^+$ T-cell subpopulation correlated with a dendritic cell stimulation in an anti-tumor immune response;

an amount of a dendritic cell subpopulation correlated with a dendritic cell stimulation by a $CD4^+$ T-cell in an anti-tumor immune response;

an amount of a CD8$^+$ T-cell subpopulation correlated with a dendritic cell stimulation in an anti-tumor immune response;

an amount of regulatory T-cells or a CD4$^+$ T-cell subpopulation correlated with regulatory T-cells; and an amount of an ICOS$^+$CD62L$^{low}$CD4$^+$ T-cell subpopulation;

as an indicator for predicting a response to cancer immunotherapy of a subject, the method comprising:

measuring the X; and measuring the Y;

wherein a comparison of a relative value of X to Y with an ineffective group threshold value is used as an indicator for predicting that the subject is not a part of an ineffective group to the cancer immunotherapy.

(Item 9)

The method of item 8, wherein the amounts (X) and (Y) are respectively selected from the group consisting of:

an amount of a CD62L$^{low}$CD4$^+$ T-cell subpopulation;

an amount of a CCR7$^-$CD4$^+$ T-cell subpopulation;

an amount of a LAG-3$^+$CD62L$^{low}$CD4$^+$ T-cell subpopulation;

an amount of an ICOS$^+$CD62L$^{low}$CD4$^+$ T-cell subpopulation;

an amount of a Foxp3$^+$CD25$^+$CD4$^+$ T-cell subpopulation;

an amount of an HLA-DR$^+$ dendritic cell subpopulation;

an amount of a CD80$^+$ dendritic cell subpopulation;

an amount of a CD86$^+$ dendritic cell subpopulation;

an amount of a PD-L1$^+$ dendritic cell subpopulation;

an amount of a CD62L$^{low}$CD8$^+$ T-cell subpopulation;

an amount of a CD137$^+$CD8$^+$ T-cell subpopulation; and an amount of a CD28$^+$CD62L$^{low}$CD8$^+$ T-cell subpopulation.

(Item 10)

The method of item 8 or 9, wherein the relative value is X/Y.

(Item 11)

The method of item 8 or 9, wherein the relative value is $X^2$/Y.

(Item 12)

The method of any one of items 1 to 11, further using a ratio of Foxp3$^+$CD25$^+$ T-cell subpopulation in CD4$^+$ T-cells, a ratio of ICOS$^+$CD62L$^{low}$CD4$^+$ T cell subpopulation in CD62L$^{low}$CD4$^+$ T-cells, a ratio of LAG-3$^+$CD62L$^{low}$CD4$^+$ T cell subpopulation in CD62L$^{low}$CD4$^+$ T-cells, or a ratio of PD-1$^+$CD62L$^{low}$CD4$^+$ T cell subpopulation in CD62L$^{low}$CD4$^+$ T-cells, in a subject who is shown to be not a part of the ineffective group as an indicator of a response to cancer immunotherapy of the subject, wherein the ratio of the Foxp3$^+$CD25$^+$ T-cell subpopulation in the CD4$^+$ T-cells, the ratio of the ICOS$^+$CD62L$^{low}$CD4$^+$ T cell subpopulation in the CD62L$^{low}$CD4$^+$ T-cells the ratio of LAG-3$^+$CD62L$^{low}$CD4$^+$ T cell subpopulation in CD62L$^{low}$CD4$^+$ T-cells, or the ratio of PD-1$^+$CD62L$^{low}$CD4$^+$ T cell subpopulation in CD62L$^{low}$CD4$^+$ T-cells, higher than a response group threshold value indicates that the subject is a part of a response group.

(Item 13)

The method of any one of items 1 to 12, wherein the ineffective group threshold value is determined by considering sensitivity and specificity for the detection of an ineffective group.

(Item 14)

The method of any one of items 1 to 13, wherein the ineffective group threshold value is determined so that sensitivity for the detection of an ineffective group exceeds about 90%.

(Item 15)

The method of any one of items 1 to 13, wherein the ineffective group threshold value is determined so that specificity for the detection of an ineffective group exceeds about 90%.

(Item 16)

The method of any one of items 1 to 15, wherein the sample is a peripheral blood sample.

(Item 17)

The method of any one of items 1 to 16, wherein the cancer immunotherapy comprises administration of an immune checkpoint inhibitor.

(Item 18)

The method of item 17, wherein the immune checkpoint inhibitor is selected from the group consisting of a PD-1 inhibitor and a PD-L1 inhibitor.

(Item 19)

The method of item 18, wherein the PD-1 inhibitor is an anti-PD-1 antibody that inhibits an interaction between PD-1 and PD-L1.

(Item 20)

The method of item 18, wherein the PD-L1 inhibitor is an anti-PD-L1 antibody that inhibits an interaction between PD-1 and PD-L1.

(Item 21)

The method of item 18, wherein the PD-1 inhibitor or PD-L1 inhibitor comprises nivolumab, pembrolizumab, durvalumab, atezolizumab, or avelumab.

(Item 22)

A method of treating a subject with cancer, comprising:

(1) determining a relative amount selected from the group consisting of:

a relative amount of a CD4$^+$ T-cell subpopulation correlated with a dendritic cell stimulation in an anti-tumor immune response;

a relative amount of a dendritic cell subpopulation correlated with a dendritic cell stimulation by a CD4$^+$ T-cell in an anti-tumor immune response; and a relative amount of a CD8$^+$ T-cell subpopulation correlated with a dendritic cell stimulation in an anti-tumor immune response;

(2) determining that the subject is not a part of an ineffective group with respect to a response to cancer immunotherapy if the relative amount is higher than an ineffective group threshold value; and (3) applying the cancer immunotherapy to the subject if the subject is determined to be not a part of an ineffective group.

(Item 23)

The method of item 22, wherein the relative amount is selected from the group consisting of:

a ratio of a CD62L$^{low}$CD4$^+$ T-cell subpopulation in CD4$^+$ T-cells;

a ratio of a CCR7$^-$CD4$^+$ T-cell subpopulation in CD4$^+$ T-cells;

a ratio of a LAG-3$^+$CD62L$^{low}$CD4$^+$ T-cell subpopulation in CD62L$^{low}$CD4$^+$ T-cells;

a ratio of an ICOS$^+$CD62L$^{low}$CD4$^+$ T-cell subpopulation in CD62L$^{low}$CD4$^+$ T-cells;

a ratio of a CCR4$^+$CD25$^+$CD4$^+$ T-cell subpopulation in CD4$^+$ T-cells;

a ratio of a CD62L$^{high}$CD25$^+$CD4$^+$ T-cell subpopulation in CD4$^+$ T-cells;
a ratio of a CD127$^+$CD25$^+$CD4$^+$ T-cell subpopulation in CD4$^+$ T-cells;
a ratio of a CD45RA$^-$Foxp3$^+$CD4$^+$ T-cell subpopulation in CD4$^+$ T-cells;
a ratio of a Foxp3$^+$CD25$^+$CD4$^+$ T-cell subpopulation in CD4$^+$ T-cells;
a ratio of an HLA-DR$^+$ dendritic cell subpopulation in dendritic cells;
a ratio of a CD80$^+$ dendritic cell subpopulation in dendritic cells;
a ratio of a CD86$^+$ dendritic cell subpopulation in dendritic cells;
a ratio of a PD-L1$^+$ dendritic cell subpopulation in dendritic cells;
a ratio of a CD62L$^{low}$CD8$^+$ T-cell subpopulation in CD8$^+$ T-cells;
a ratio of a CD137$^+$CD8$^+$ T-cell subpopulation in CD8$^+$ T-cells; and
an ratio of a CD28$^+$CD62L$^{low}$CD8$^+$ T-cell subpopulation in CD62L$^{low}$CD8$^+$ T-cells.
(Item 24)
A method of treating a subject with cancer, comprising:
determining amounts (X, Y) selected from the group consisting of:
an amount of a CD4$^+$ T-cell subpopulation correlated with a dendritic cell stimulation in an anti-tumor immune response;
an amount of a dendritic cell subpopulation correlated with a dendritic cell stimulation by a CD4$^+$ T-cell in an anti-tumor immune response;
an amount of a CD8$^+$ T-cell subpopulation correlated with a dendritic cell stimulation in an anti-tumor immune response;
an amount of regulatory T-cells or a CD4$^+$ T-cell subpopulation correlated with regulatory T-cells; and
an amount of an ICOS$^+$CD62L$^{low}$CD4$^+$ T-cell subpopulation; using a comparison of a relative value of X to Y with an ineffective group threshold value to determine whether the subject is a part of an ineffective group with respect to a response to cancer immunotherapy; and
applying the cancer immunotherapy to the subject if the subject is determined to be not a part of an ineffective group.
(Item 25)
The method of item 24, wherein the amounts (X) and (Y) are respectively selected from the group consisting of:
an amount of a CD62L$^{low}$CD4$^+$ T-cell subpopulation;
an amount of a CCR7$^-$CD4$^+$ T-cell subpopulation;
an amount of a LAG-3$^+$CD62L$^{low}$CD4$^+$ T-cell subpopulation;
an amount of an ICOS$^+$CD62L$^{low}$CD4$^+$ T-cell subpopulation;
an amount of a Foxp3$^+$CD25$^+$CD4$^+$ T-cell subpopulation;
an amount of an HLA-DR$^+$ dendritic cell subpopulation;
an amount of a CD80$^+$ dendritic cell subpopulation;
an amount of a CD86$^+$ dendritic cell subpopulation;
an amount of a PD-L1$^+$ dendritic cell subpopulation;
an amount of a CD62L$^{low}$CD8$^+$ T-cell subpopulation; and
an amount of a CD137$^+$CD8$^+$ T-cell subpopulation; and
an amount of a CD28$^+$CD62L$^{low}$CD8$^+$ T-cell subpopulation.
(Item 26)
A method of treating a subject with cancer, comprising:
determining amounts (X, Y) selected from the group consisting of:

an amount of a CD4$^+$ T-cell subpopulation correlated with a dendritic cell stimulation in an anti-tumor immune response;
an amount of a dendritic cell subpopulation correlated with a dendritic cell stimulation by a CD4$^+$ T-cell in an anti-tumor immune response;
an amount of a CD8$^+$ T-cell subpopulation correlated with a dendritic cell stimulation in an anti-tumor immune response;
an amount of regulatory T-cells or a CD4$^+$ T-cell subpopulation correlated with regulatory T-cells; and an amount of an ICOS$^+$CD62L$^{low}$CD4$^+$ T-cell subpopulation;
using a comparison of a relative value of X to Y with an ineffective group threshold value to determine whether the subject is a part of an ineffective group with respect to a response;
determining that the subject is a part of a response group with respect to a response to cancer immunotherapy if it is determined that the subject is not a part of an ineffective group, and a ratio of a Foxp3$^+$CD25$^+$ T-cell subpopulation, a ratio of an ICOS$^+$CD62L$^{low}$CD4$^+$ T-cell subpopulation, a ratio of LAG-3$^+$CD62L$^{low}$CD4$^+$ T cell subpopulation, or a ratio of PD-1$^+$CD62L$^{low}$CD4$^+$ T cell subpopulation is higher than a response group threshold value; and
applying the cancer immunotherapy to the subject if the subject is determined to be a part of a response group.
(Item 27)
A kit for predicting a response to cancer immunotherapy of a subject, comprising an agent for detecting a combination of markers selected from the group consisting of:
*a combination of CD4 and CD62L;
*a combination of CD4 and CCR7;
*a combination of CD4, CD62L, and LAG-3;
*a combination of CD4, CD62L, and ICOS;
*a combination of CD4, CD62L, and CD25;
*a combination of CD4, CD127, and CD25;
*a combination of CD4, CD45RA, and Foxp3;
*a combination of CD4, CD25, and Foxp3;
*a combination of CD11c, CD141, and HLA-DR;
*a combination of CD11c, CD141, and CD80;
*a combination of CD11c, CD123, and HLA-DR;
*a combination of CD11c, CD123, and CD80;
*a combination of CD8 and CD62L;
*a combination of CD8 and CD137; and
*a combination of CD28, CD62L, and CD8.
(Item 28)
The kit of item 27, comprising an agent for detecting CD4 and CD62L.
(Item 29)
The kit of item 27, comprising an agent for detecting CD4, CD25, CD62L, and Foxp3.
(Item 30)
The kit of any one of items 27 to 29, wherein the detection agent is an antibody.
(Item 31)
A composition comprising an immune checkpoint inhibitor for treating cancer in a subject, characterized in that the subject has a relative amount selected from the group consisting of:
a relative amount of a CD4$^+$ T-cell subpopulation correlated with a dendritic cell stimulation in an anti-tumor immune response;
a relative amount of a dendritic cell subpopulation correlated with a dendritic cell stimulation by a CD4$^+$ T-cell in an anti-tumor immune response; and a relative amount of a CD8⁺ T-cell subpopulation correlated with a dendritic cell stimulation in an anti-tumor immune response;
wherein the relative amount is equal to or greater than an ineffective group threshold value.

(Item 32)

The composition of item 31, wherein the relative amount is selected from the group consisting of:
a ratio of a CD62L$^{low}$CD4⁺ T-cell subpopulation in CD4⁺ T-cells;
a ratio of a CCR7⁻CD4⁺ T-cell subpopulation in CD4⁺ T-cells;
a ratio of a LAG-3⁺CD62L$^{low}$CD4⁺ T-cell subpopulation in CD62L$^{low}$CD4⁺ T-cells;
a ratio of an ICOS⁺CD62L$^{low}$CD4⁺ T-cell subpopulation in CD62L$^{low}$CD4⁺ T-cells;
a ratio of a CCR4⁺CD25⁺CD4⁺ T-cell subpopulation in CD4⁺ T-cells;
a ratio of a CD62L$^{high}$CD25⁺CD4⁺ T-cell subpopulation in CD4⁺ T-cells;
a ratio of a CD127⁺CD25⁺CD4⁺ T-cell subpopulation in CD4⁺ T-cells;
a ratio of a CD45RA⁻Foxp3⁺CD4⁺ T-cell subpopulation in CD4⁺ T-cells;
a ratio of a Foxp3⁺CD25⁺CD4⁺ T-cell subpopulation in CD4⁺ T-cells;
a ratio of an HLA-DR⁺ dendritic cell subpopulation in dendritic cells;
a ratio of a CD80⁺ dendritic cell subpopulation in dendritic cells;
a ratio of a CD86⁺ dendritic cell subpopulation in dendritic cells;
a ratio of a PD-L1⁺ dendritic cell subpopulation in dendritic cells;
a ratio of a CD62L$^{low}$CD8⁺ T-cell subpopulation in CD8⁺ T-cells;
a ratio of a CD137⁺CD8⁺ T-cell subpopulation in CD8⁺ T-cells; and
a ratio of a CD28⁺CD62L$^{low}$CD8⁺ T-cell subpopulation in CD62L$^{low}$CD8⁺ T-cells.

(Item 33)

A composition comprising an immune checkpoint inhibitor for treating cancer in a subject, characterized in that the subject is a subject selected by comparison of an ineffective group threshold value with a relative value of amounts (X, Y) selected from the group consisting of:
an amount of a CD4⁺ T-cell subpopulation correlated with a dendritic cell stimulation in an anti-tumor immune response;
an amount of a dendritic cell subpopulation correlated with a dendritic cell stimulation in an anti-tumor immune response; and
an amount of a CD8⁺ T-cell subpopulation correlated with a dendritic cell stimulation in an anti-tumor immune response;
an amount of regulatory T-cells or a CD4⁺ T-cell subpopulation correlated with regulatory T-cells; and an amount of an ICOS⁺CD62L$^{low}$CD4⁺ T-cell subpopulation.

(Item 34)

A composition comprising an immune checkpoint inhibitor for treating cancer in a subject, characterized in that
the subject is a subject selected by comparison of an ineffective group threshold value with a relative value of amounts (X, Y) selected from the group consisting of:
an amount of a CD4⁺ T-cell subpopulation correlated with a dendritic cell stimulation in an anti-tumor immune response;
an amount of a dendritic cell subpopulation correlated with a dendritic cell stimulation in an anti-tumor immune response; and
an amount of a CD8⁺ T-cell subpopulation correlated with a dendritic cell stimulation in an anti-tumor immune response;
an amount of regulatory T-cells or a CD4⁺ T-cell subpopulation correlated with regulatory T-cells; and an amount of an ICOS⁺CD62L$^{low}$CD4⁺ T-cell subpopulation, and
in a sample derived from the subject, having
a ratio of Foxp3⁺CD25⁺ T-cell subpopulation in CD4⁺ T-cells;
a ratio of the ICOS⁺CD62L$^{low}$CD4⁺ T-cell subpopulation in the CD62L$^{low}$CD4⁺ T-cells;
a ratio of LAG-3⁺CD62L$^{low}$CD4⁺ T cell subpopulation in CD62L$^{low}$CD4⁺ T-cells; or
a ratio of PD-1⁺CD62L$^{low}$CD4⁺ T cell subpopulation in CD62L$^{low}$CD4⁺ T-cells being higher than a response group threshold value.

(Item 35)

The composition of any one of items 31 to 34, wherein the immune checkpoint inhibitor is selected from the group consisting of a PD-1 inhibitor and a PD-L1 inhibitor.

(Item 36)

The composition of item 35, wherein the PD-1 inhibitor is an anti-PD-L1 antibody that inhibits an interaction between PD-L1 and PD-1.

(Item 37)

The composition of item 35, wherein the PD-L1 inhibitor is an anti-PD-L1 antibody that inhibits an interaction between PD-1 and PD-L1.

(Item 38)

The composition of item 35, wherein the PD-1 inhibitor of PD-L1 inhibitor is nivolumab, pembrolizumab, durvalumab, atezolizumab, or avelumab.

(Item 39)

A composition for treating or preventing cancer, comprising a cell selected from the group consisting of:
a CD62L$^{low}$CD4⁺ T-cell;
a CCR7⁻CD4⁺ T-cell;
a LAG-3⁺CD62L$^{low}$CD4⁺ T-cell;
an ICOS⁺CD62L$^{low}$CD4⁺ T-cell;
a CCR4⁺CD25⁺CD4⁺ T-cell;
a CD62L$^{high}$CD25⁺CD4⁺ T-cell;
a CD127⁺CD25⁺CD4⁺ T-cell;
a CD45RA⁻Foxp3⁺CD4⁺ T-cell;
a Foxp3⁺CD25⁺CD4⁺ T-cell;
an HLA-DR⁺ dendritic cell;
a CD80⁺ dendritic cell;
a CD86⁺ dendritic cell;
a PD-L1⁺ dendritic cell;
a CD62L$^{low}$CD8⁺ T-cell;
a CD137⁺CD8⁺ T-cell; and
a CD28⁺CD62L$^{low}$CD8⁺ T-cell.

(Item 40)

The composition of item 39 for concomitant use with cancer immunotherapy.

(Item 41)

The composition of item 39, characterized in that the composition is administered in combination with an immune checkpoint inhibitor.

(Item 42)

The composition of item 41, wherein the immune checkpoint inhibitor is selected from the group consisting of a PD-1 inhibitor and a PD-L1 inhibitor.

(Item 43)

The composition of item 42, wherein the PD-1 inhibitor is an anti-PD-1 antibody that inhibits an interaction between PD-1 and PD-L1.

(Item 44)

The composition of item 42, wherein the PD-L1 inhibitor is an anti-PD-L1 antibody that inhibits an interaction between PD-1 and PD-L1.

(Item 45)

The composition of item 42, wherein the PD-1 inhibitor or PD-L1 inhibitor comprises nivolumab, pembrolizumab, durvalumab, atezolizumab, or avelumab.

(Item 46)

The composition of any one of items 39 to 45, further comprising a $CD62L^{low}CD8^+$ T-cell.

(Item 47)

The composition of any one of items 39 to 46 for making cancer immunotherapy effective in a subject to whom cancer immunotherapy is predicted to be ineffective.

(Item 48)

The composition of any one of items 39 to 47 for sustaining an effect of cancer immunotherapy.

(Item 49)

The composition of any one of items 39 to 48, wherein the $CD62L^{low}CD4^+$ T-cell is from a subject to whom the composition is administered.

(Item 50)

A method of manufacturing a composition for treating or preventing cancer comprising $CD62L^{low}CD4^+$ T-cells, comprising purifying $CD62L^{low}CD4^+$ T-cells from a T-cell population derived from a human.

(Item 51)

The method of item 50, wherein the purifying comprises removing a CD62L high expression cell from a T-cell population.

(Item 52)

A kit comprising a substance, which specifically binds to CD62L, for purifying $CD62L^{low}CD4^+$ T-cells.

(Item A1)

A method of using a ratio of $CD62L^{low}$ T-cells in $CD4^+$ T-cells of a subject as an indicator for predicting a response to cancer immunotherapy of the subject, comprising determining the ratio of $CD62L^{low}$ T-cells in $CD4^+$ T-cells in a sample derived from the subject, the ratio higher than an ineffective group threshold value indicating that the subject is not a part of an ineffective group to the cancer immunotherapy.

(Item A2)

A method of using a ratio of $Foxp3^+CD25^+$ T-cells in $CD4^+$ T-cells of a subject as an indicator for predicting a response to cancer immunotherapy of the subject, comprising determining the ratio of $Foxp3^+CD25^+$ T-cells in $CD4^+$ T-cells in a sample derived from the subject, the ratio lower than an ineffective group threshold value indicating that the subject is not a part of an ineffective group to the cancer immunotherapy.

(Item A3)

A method of using a relative value of an amount of $CD4^+CD62L^{low}$ T-cells of a subject (X) to an amount of $CD4^+Foxp3^+CD25^+$ T-cells (Y) as an indicator for predicting a response to cancer immunotherapy of the subject, the method comprising:
measuring the X; and
measuring the Y;
wherein a comparison of a relative value of X to Y with an ineffective group threshold value is used as an indicator for predicting that the subject is not a part of an ineffective group to the cancer immunotherapy.

(Item A4)

The method of item A3, wherein the relative value is X/Y.

(Item A5)

The method of item A3, wherein the relative value is $X^2/Y$.

(Item A6)

The method of any one of items A1 to A5, further using a ratio of $Foxp3^+CD25^+$ T-cells in $CD4^+$ T-cells in a subject who is shown not to be a part of the ineffective group as an indicator of a response to cancer immunotherapy of the subject, wherein the ratio of the $Foxp3^+CD25^+CD4^+$ T-cells in the $CD4^+$ T-cells higher than a response group threshold value indicates that the subject is a part of a response group.

(Item A7)

The method of any one of items A1 to A6, wherein the ineffective group threshold value is determined by considering sensitivity and specificity for the detection of an ineffective group.

(Item A8)

The method of any one of items A1 to A7, wherein the ineffective group threshold value is determined so that sensitivity for the detection of an ineffective group exceeds about 90%.

(Item A9)

The method of any one of items A1 to A8, wherein the ineffective group threshold value is determined so that specificity for the detection of an ineffective group exceeds about 90%.

(Item A10)

The method of any one of items A1 to A9, wherein the sample is a peripheral blood sample.

(Item A11)

The method of any one of items A1 to A10, wherein the cancer immunotherapy comprises administration of an immune checkpoint inhibitor.

(Item A12)

The method of item A11, wherein the immune checkpoint inhibitor is selected from the group consisting of a PD-1 inhibitor and a PD-L1 inhibitor.

(Item A13)

The method of item A12, wherein the PD-1 inhibitor is an anti-PD-1 antibody that inhibits an interaction between PD-1 and PD-L1.

(Item A14)

The method of item A12, wherein the PD-L1 inhibitor is an anti-PD-L1 antibody that inhibits an interaction between PD-1 and PD-L1.

(Item A15)

The method of item A12, wherein the PD-1 inhibitor or PD-L1 inhibitor comprises nivolumab, pembrolizumab, durvalumab, atezolizumab, or avelumab.

(Item A16)

A method of treating a subject with cancer, comprising:
determining a ratio of $CD62L^{low}$ T-cells in $CD4^+$ T-cells in a sample derived from the subject;
determining that the subject is not a part of an ineffective group with respect to a response to cancer immunotherapy if the ratio of $CD62L^{low}$ T-cells in $CD4^+$ T-cells is higher than an ineffective group threshold value; and
applying the cancer immunotherapy to the subject if the subject is determined to be not a part of an ineffective group.

(Item A17)

A method of treating a subject with cancer, comprising:
determining a ratio of $Foxp3^+CD25^+$ T-cells in $CD4^+$ T-cells in a sample derived from the subject;

determining that the subject is not a part of an ineffective group with respect to a response to cancer immunotherapy if the ratio of Foxp3$^+$CD25$^+$ T-cells in CD4$^+$ T-cells is lower than an ineffective group threshold value; and applying the cancer immunotherapy to the subject if the subject is determined to be not a part of an ineffective group.

(Item A18)

A method of treating a subject with cancer, comprising:
determining an amount of CD4$^+$CD62L$^{low}$ T-cells (X);
determining an amount of CD4$^+$Foxp3$^+$CD25$^+$ T-cells (Y);
using a comparison of a relative value of X to Y with an ineffective group threshold value to determine whether the subject is a part of an ineffective group with respect to a response to cancer immunotherapy; and
applying the cancer immunotherapy to the subject if the subject is determined to be not a part of an ineffective group.

(Item A19)

A method of treating a subject with cancer, comprising:
determining an amount of CD4$^+$CD62L$^{low}$ T-cells (X);
determining an amount of CD4$^+$Foxp3$^+$CD25$^+$ T-cells (Y);
using a comparison of a relative value of X to Y with an ineffective group threshold value to determine whether the subject is a part of an ineffective group with respect to a response to cancer immunotherapy;
determining that the subject is a part of a response group with respect to a response to cancer immunotherapy if the subject is determined to be not a part of an ineffective group and a ratio of Foxp3$^+$CD25$^+$ T-cells is higher than a response group threshold value; and
applying the cancer immunotherapy to the subject if the subject is determined to be a part of a response group.

(Item A20)

A kit for predicting a response to cancer immunotherapy of a subject, comprising an agent for detecting one or more cell surface markers selected from CD4, CD25, CD62L, and Foxp3.

(Item A21)

The kit of item A20, comprising an agent for detecting CD4 and CD62L.

(Item A22)

The kit of item A20 or A21, comprising an agent for detecting CD4, CD25, CD62L, and Foxp3.

(Item A23)

The kit of any one of items A20 to 22, wherein the detection agent is an antibody.

(Item A24)

A composition comprising an immune checkpoint inhibitor for treating cancer in a subject, characterized in that the subject has a ratio of CD62L$^{low}$ T-cells in CD4+ cells in a sample derived from the subject, wherein the ratio is equal to or greater than an ineffective group threshold value.

(Item A25)

A composition comprising an immune checkpoint inhibitor for treating cancer in a subject, characterized in that the subject has a ratio of Foxp3$^+$CD25$^+$ T-cells in CD4$^+$ cells in a sample derived from the subject, wherein the ratio is equal to or less than an ineffective group threshold value.

(Item A26)

A composition comprising an immune checkpoint inhibitor for treating cancer in a subject, characterized in that the subject is a subject selected by comparison of an ineffective group threshold value with a relative value of an amount of CD4$^+$CD62L$^{low}$ T-cells (X) in a sample derived from the subject to an amount of CD4$^+$Foxp3$^+$CD25+ T-cells (Y) in a sample derived from the subject.

(Item A27)

A composition comprising an immune checkpoint inhibitor for treating cancer in a subject, characterized in that the subject is a subject selected by comparison of an ineffective group threshold value with a relative value of an amount of CD4$^+$CD62L$^{low}$ T-cells (X) in a sample derived from the subject to an amount of CD4$^+$Foxp3$^+$CD25$^+$ T-cells (Y), and in a sample derived from the subject, having a ratio of Foxp3$^+$CD25$^+$ T-cell subpopulation in CD4$^+$ T-cells being equal to or higher than a response group threshold value.

(Item A28)

The composition of any one of items A24 to A27, wherein the immune checkpoint inhibitor is selected from the group consisting of a PD-1 inhibitor and a PD-L1 inhibitor.

(Item A29)

The composition of item A28, wherein the PD-1 inhibitor is an anti-PD-1 antibody that inhibits an interaction between PD-1 and PD-L1.

(Item A30)

The composition of item A28, wherein the PD-L1 inhibitor is an anti-PD-L1 antibody that inhibits an interaction between PD-1 and PD-L1.

(Item A31)

The composition of item A28, wherein the PD-1 inhibitor or PD-L1 inhibitor comprises nivolumab, pembrolizumab, durvalumab, atezolizumab, or avelumab.

(Item A32)

A composition for treating or preventing cancer, comprising a CD62L$^{low}$CD4$^+$ T-cell.

(Item A33)

The composition of item A32 for concomitant use with cancer immunotherapy.

(Item A34)

The composition of item A32, characterized in that the composition is administered in combination with an immune checkpoint inhibitor.

(Item A35)

The composition of items A34, wherein the immune checkpoint inhibitor is selected from the group consisting of a PD-1 inhibitor and a PD-L1 inhibitor.

(Item A36)

The composition of item A35, wherein the PD-1 inhibitor is an anti-PD-1 antibody that inhibits an interaction between PD-1 and PD-L1.

(Item A37)

The composition of item A35, wherein the PD-L1 inhibitor is an anti-PD-L1 antibody that inhibits an interaction between PD-1 and PD-L1.

(Item A38)

The composition of item A35, wherein the PD-1 inhibitor or PD-L1 inhibitor comprises nivolumab, pembrolizumab, durvalumab, atezolizumab, or avelumab.

(Item A39)

The composition of any one of items A32 to A38, further comprising a CD62L$^{low}$CD8$^+$ T-cell.

(Item A40)

The composition of any one of items A32 to A39 for making cancer immunotherapy effective in a subject for whom the cancer immunotherapy is predicted to be ineffective.

(Item A41)

The composition of any one of items A32 to A40 for sustaining an effect of cancer immunotherapy.

(Item A42)

The composition of any one of items A32 to A41, wherein the CD62L$^{low}$CD4$^+$ T-cell is from a subject to whom the composition is administered.

(Item A43)

A method of manufacturing a composition for treating or preventing cancer comprising $CD62L^{low}CD4^+$ T-cells, comprising purifying $CD62L^{low}CD4^+$ T-cells from a T-cell population derived from a human.

(Item A44)

The method of item A43, wherein the purifying comprises removing a CD62L high expression cell from a T-cell population.

(Item A45)

A kit comprising a substance, which specifically binds to CD62L, for purifying $CD62L^{low}CD4^+$ T-cells.

BRIEF DESCRIPTION OF DRAWINGS

FIG. 6 shows the sensitivity and specificity of the percentage of $CD62L^{low}$ cells in $CD4^+$ T-cells upon changing a threshold value for distinguishing a PR+SD group from PD group.

FIG. 8 shows the sensitivity and specificity when using X/Y as a relative value of the percentage of $CD62L^{low}$ cells in $CD4^+$ T-cells (X) to the percentage of $CD25^+$ FoxP3+ cells in $CD4^+$ T-cells upon changing a threshold value for distinguishing a PR+SD group from a PD group.

FIG. 10 shows the sensitivity and specificity when using $X^2/Y$ as a relative value of the percentage of $CD62L^{low}$ cells in $CD4^+$ T-cells (X) to the percentage of $CD25^+FoxP3^+$ cells in $CD4^+$ T-cells upon changing a threshold value for distinguishing a PR+SD group from a PD group.

FIG. 12 shows the sensitivity and specificity of the percentage of $CD25^+FoxP3^+$ cells in $CD4^+$ T-cells upon changing a threshold value for distinguishing a PR group and an SD group.

FIG. 14 is a diagram showing the relationship between the therapeutic effect in mice subjected to T-cell infusion and the ratio of ($CD62L^{low}$ cells in $CD4^+$ T-cells)/ ($CD62L^{high}CD25^+$ cells in $CD4^+$ T-cells). The horizontal axis indicates the number of days from tumor inoculation in mice. The composition of cells indicated by the label was infused. The vertical axis is the tumor size (mm). In the left panel, the ratio of ($CD62L^{low}$ cells in $CD4^+$ T-cells)/ ($CD62L^{high}CD25^+$ cells in $CD4^+$ T-cells) in the spleen of mice subjected to cell infusion was measured as of the time indicated by an arrow. The ratios had each of the values indicated in the bottom row. In the right panel, the ratio of ($CD62L^{low}$ cells in $CD4^+$ T-cells)/($CD62L^{high}CD25^+$ cells in $CD4^+$ T-cells) in the spleen of mice was measured over time. The values changed as indicated in the bottom row.

FIG. 16 is a graph showing the relationship between the ratio of CD80 cells (top right) and the ratio of HLA-DR+ cells (top left) in myeloid dendritic cells (mDC) and PD, SD, and PR, and a graph showing the relationship between the ratio of CD80 cells (bottom right) and the ratio of HLA-DR$^+$ cells (bottom left) in plasmacytoid dendritic cells (pDC) and PD, SD, and PR.

Figure 17:
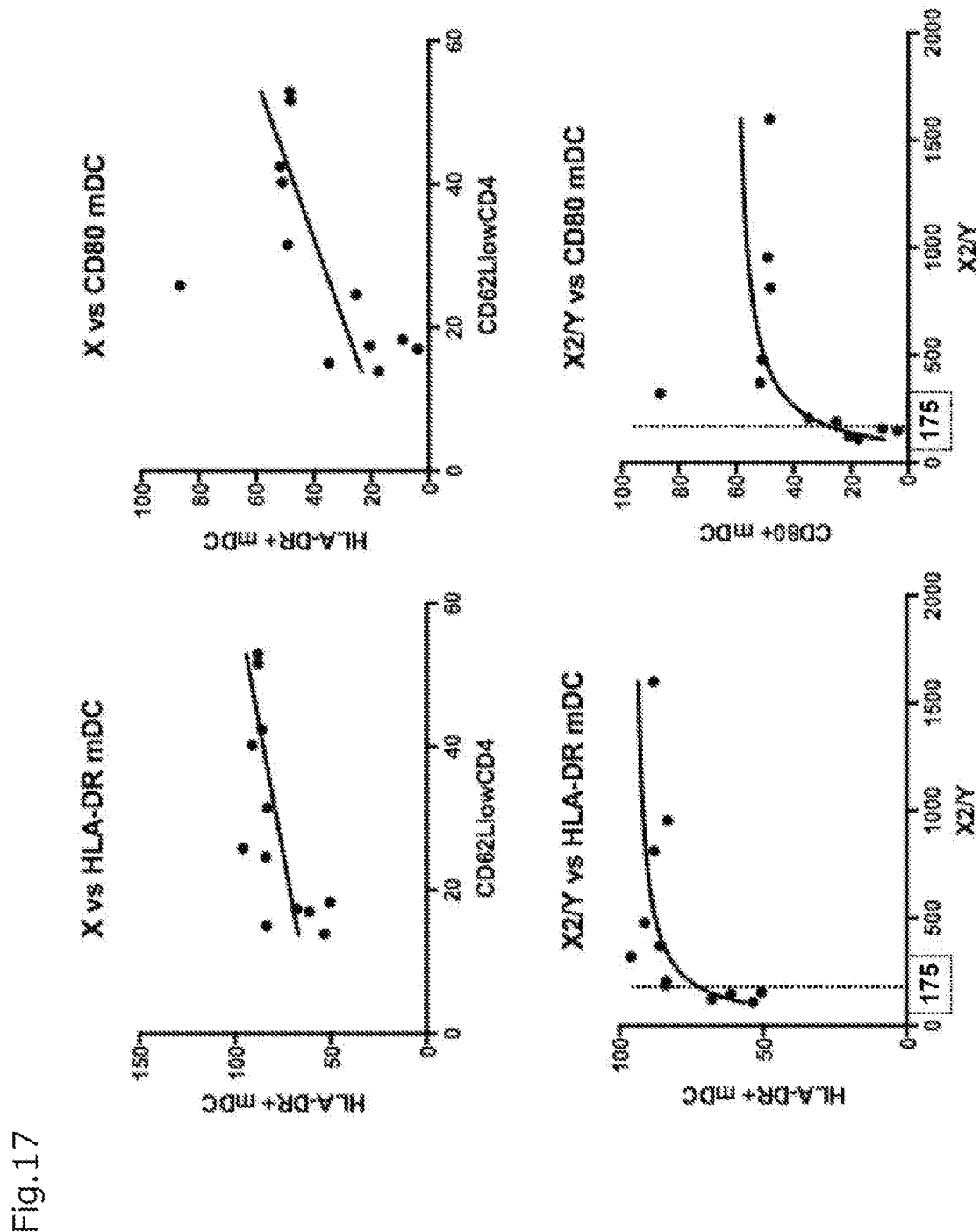

FIG. 17 is a graph showing the correlation between the ratio of CD80 cells (top right) and the ratio of HLA-DR$^+$ cells (top left) in myeloid dendritic cells (mDC) and CD62L$^{low}$CD4$^+$ T-cells, and a graph showing the correlation between the ratio of CD80 cells (bottom right) and the ratio of HLA-DR$^+$ cells (bottom left) in plasmacytoid dendritic cells (pDC) and X$^2$/Y (i.e., (amount of CD62L$^{low}$CD4$^+$ T-cells)$^2$/(CD4$^+$Foxp3$^+$CD25$^+$ T-cell)).

FIG. 18 is a result showing the ratio of CD80 cells (top right) and the ratio of HLA-DR$^+$ cells (top left) in myeloid dendritic cells (mDC) and the ratio of CD137$^+$CD62L$^{low}$CD8$^+$ T-cells to CD62L$^{low}$CD8CD62L$^{low}$CD8$^+$ T-cells.

Figure 19:
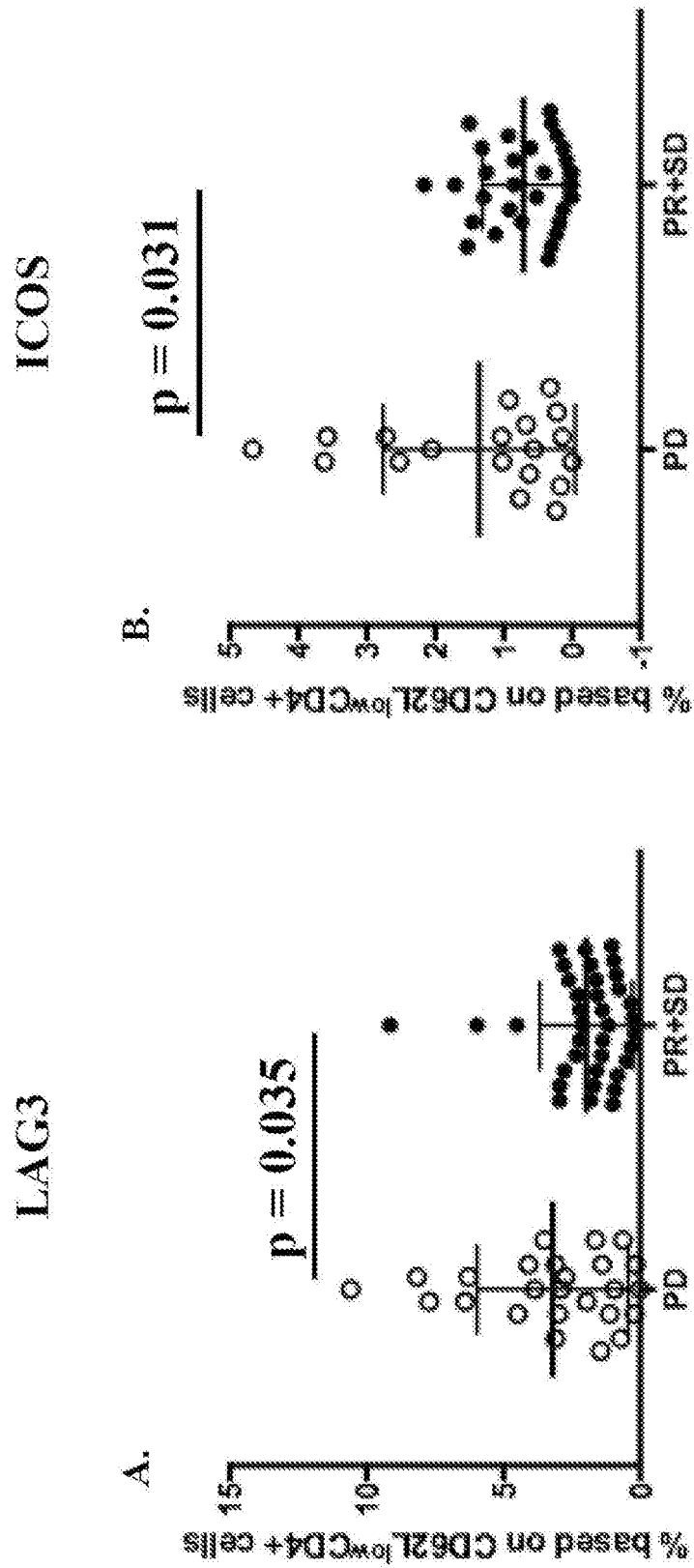

FIG. 19 is a graph showing the relationship between the ratio of ICOS$^+$ cells (right) and the ratio of LAG3$^+$ cells (left) in CD62L$^{low}$CD4$^+$ T-cells and PD and PR+SD.

Figure 20:
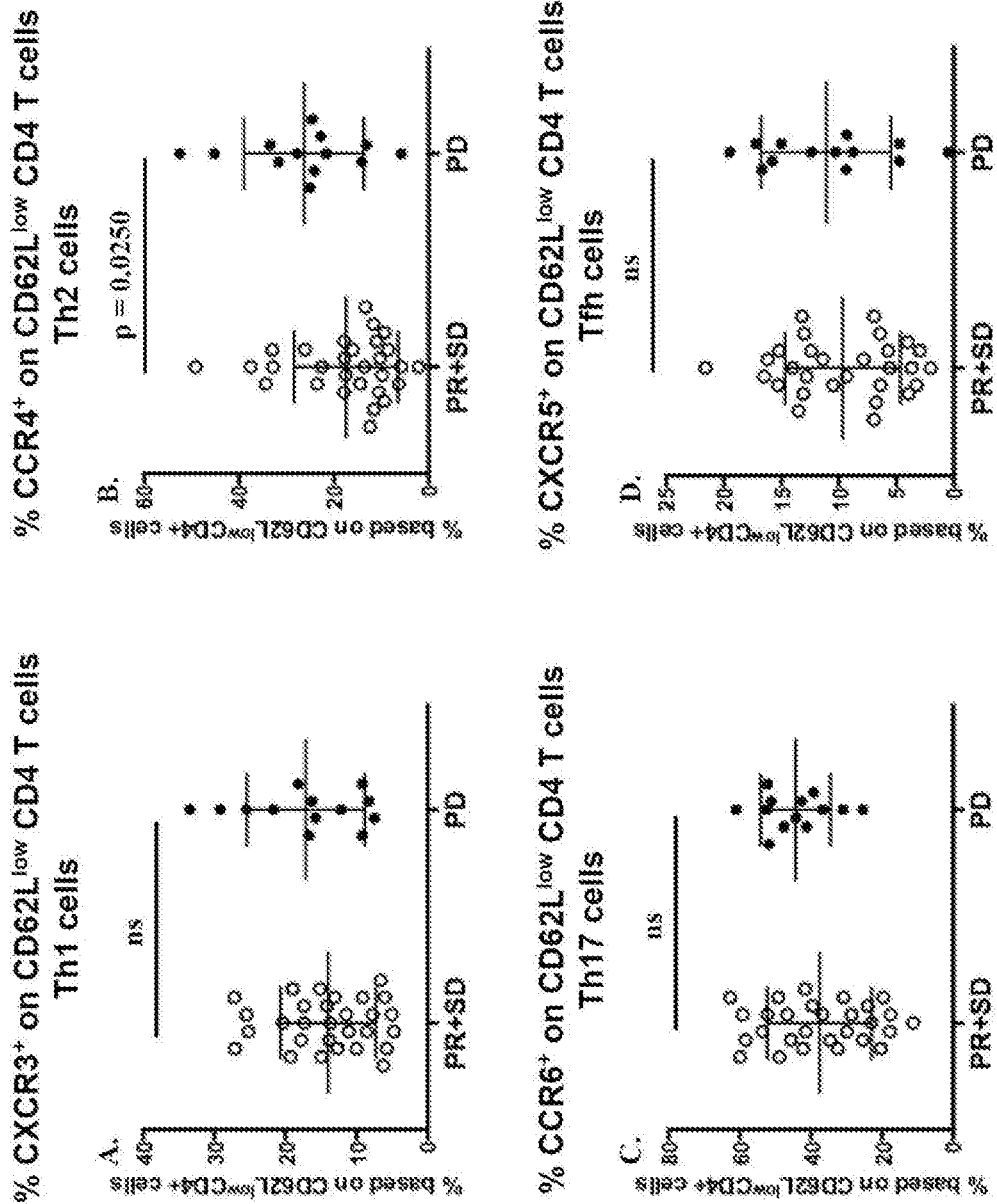

FIG. 20 is a graph showing the relationship between the ratio of CXCR3$^+$ cells (top left), the ratio of CCR4$^+$ cells (top right), the ratio of CCR6$^+$ cells (bottom left), and the ratio of CXCR5$^+$ cells (bottom right) in CD62L$^{low}$CD4$^+$ T-cells and PD and PR+SD. Only CCR4 exhibited a correlation that is sufficient as a marker (p=0.0250).

Figure 21:
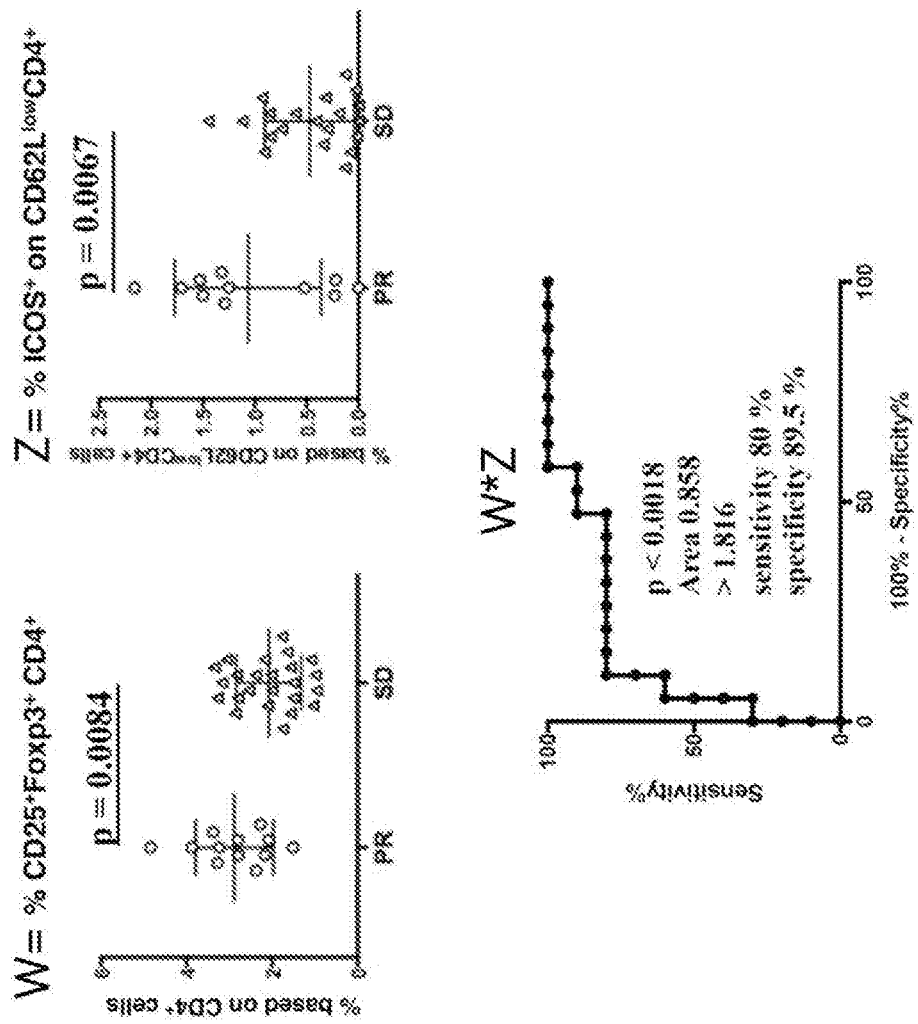

FIG. 21 is a graph showing the relationship between CD25$^+$Foxp3$^+$CD4$^+$ T-cells in CD4$^+$ T-cells (top left) or ICOS$^+$CD62L$^{low}$CD4$^+$ T-cells in CD62L$^{low}$CD4$^+$ T-cells (top right) and PR and SD. The bottom panel shows the sensitivity and specificity upon changing a threshold value of W*Z for distinguishing a PR group and an SD group using the product W*Z of the ratio of CD25$^+$Foxp3$^+$CD4$^+$ T-cells in CD4$^+$ T-cells (W) and the ratio of ICOS$^+$CD62L$^{low}$CD4$^+$ T-cells in CD62L$^{low}$CD4$^+$ T-cells (Z).

Figure 22:
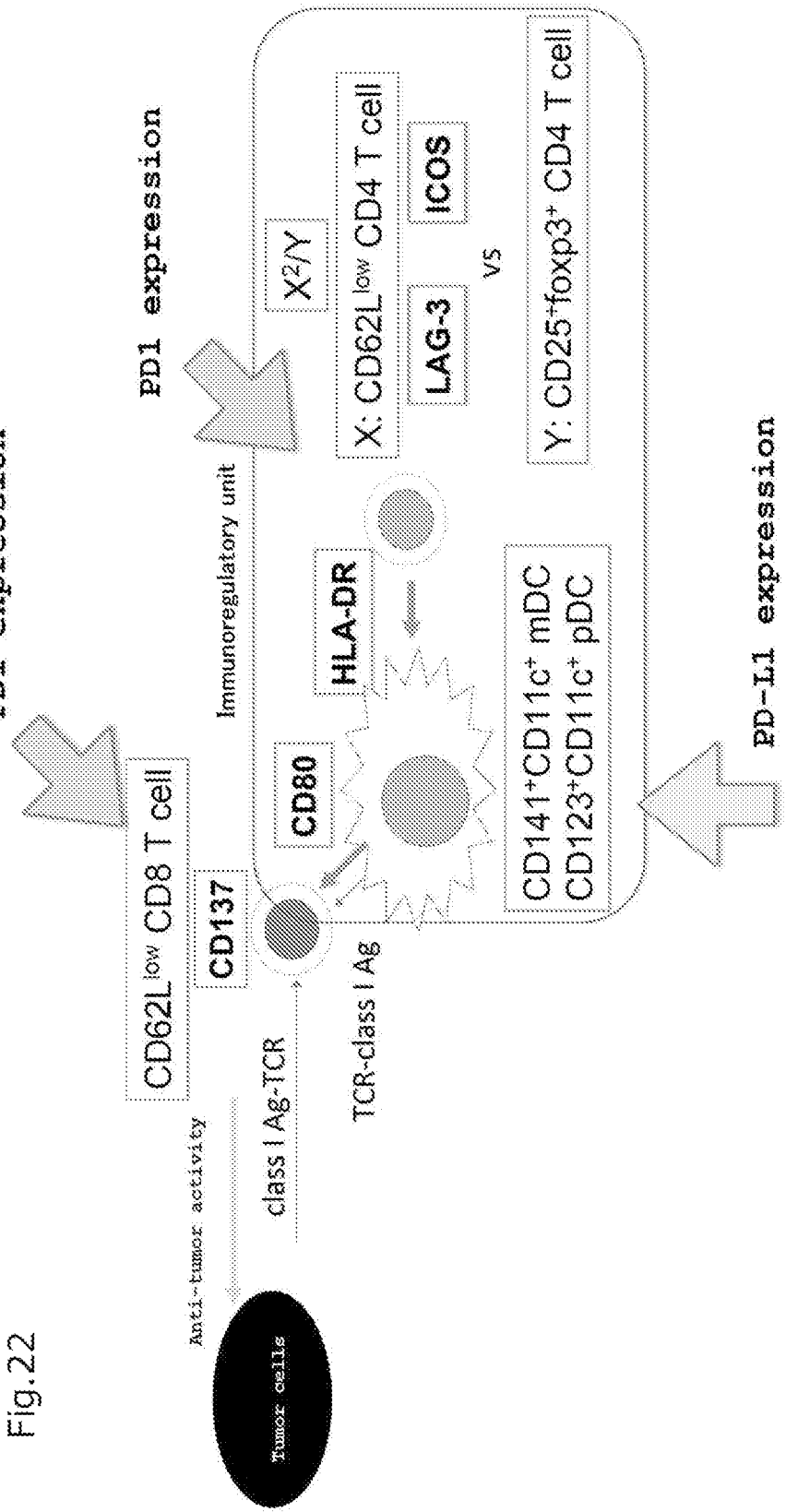

FIG. 22 is a schematic diagram disclosing the mechanism associated with the present invention.

FIG. 23 is a table showing antibodies used in the Examples.

FIG. 24 is a diagram showing logistic regression when using the shown biomarkers alone for determination of a response group.

FIG. 25 is a diagram showing logistic regression for deriving a suitable formula in a combination of the ratio of CD25$^+$Foxp3$^+$CD4$^+$ T-cells in CD4$^+$ T-cells (W) and the ratio of ICOS$^+$CD62L$^{low}$CD4$^+$ T-cells in CD62L$^{low}$CD4$^+$ T-cells (Z) for determination of a response group.

Figure 26:
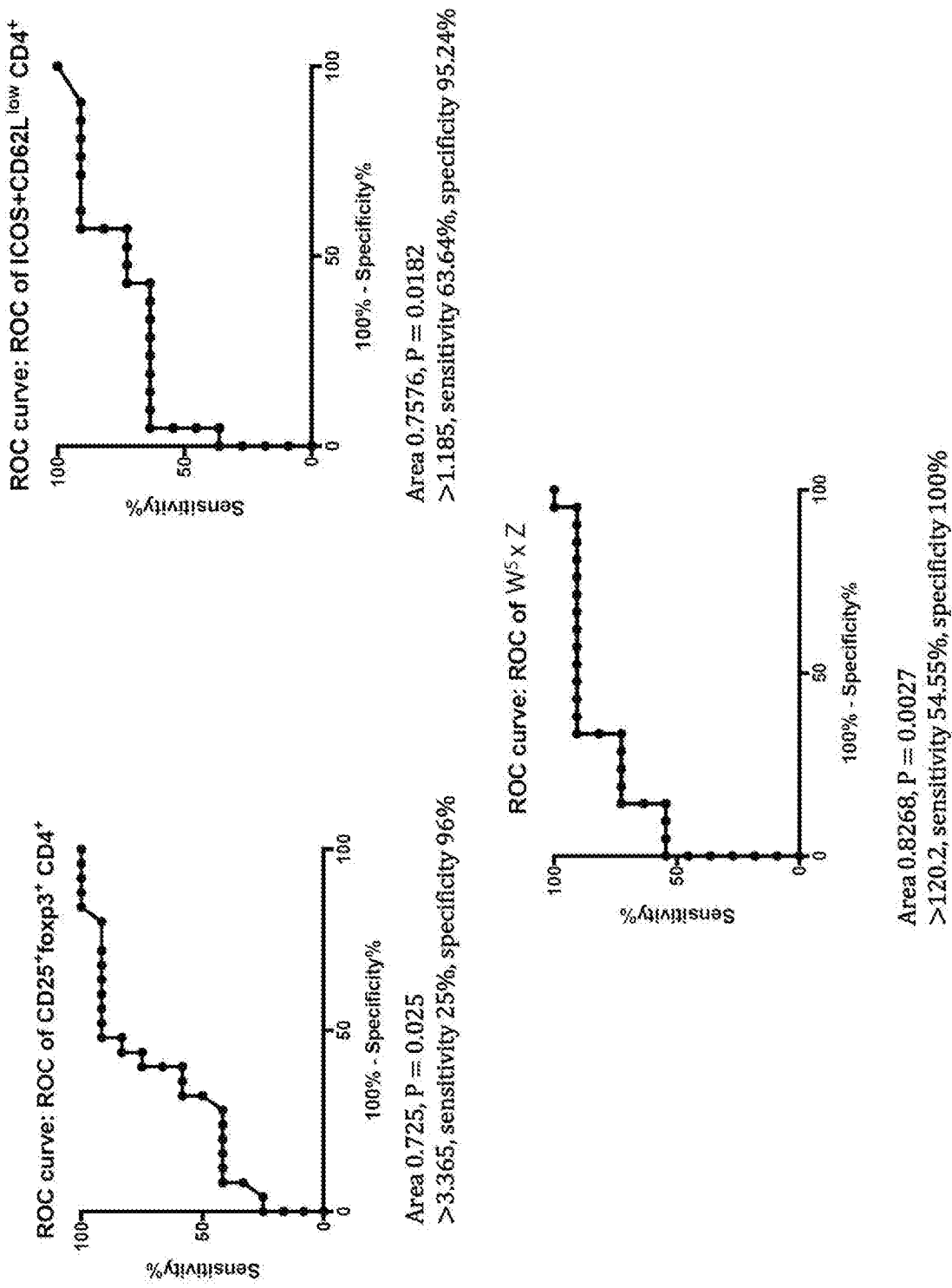

FIG. 26 is a diagram showing results of ROC analysis when using a formula of a combination of the ratio of CD25$^+$Foxp3$^+$CD4$^+$ T-cells in CD4$^+$ T-cells (W) and the ratio of ICOS$^+$CD62L$^{low}$CD4$^+$ T-cells in CD62L$^{low}$CD4$^+$ T-cells (Z), which was found by logistic regression. It is demonstrated that a response group can be determined with higher precision compared to individual biomarkers by using said formula.

FIG. 27 is a diagram showing logistic regression for deriving a suitable formula in a combination of the percentage of CD62L$^{low}$ cells in CD4$^+$ T-cells (X) and the percentage of CD25$^+$FoxP3$^+$in CD4$^+$ T-cells (Y) for determination of an ineffective group.

Figure 28:
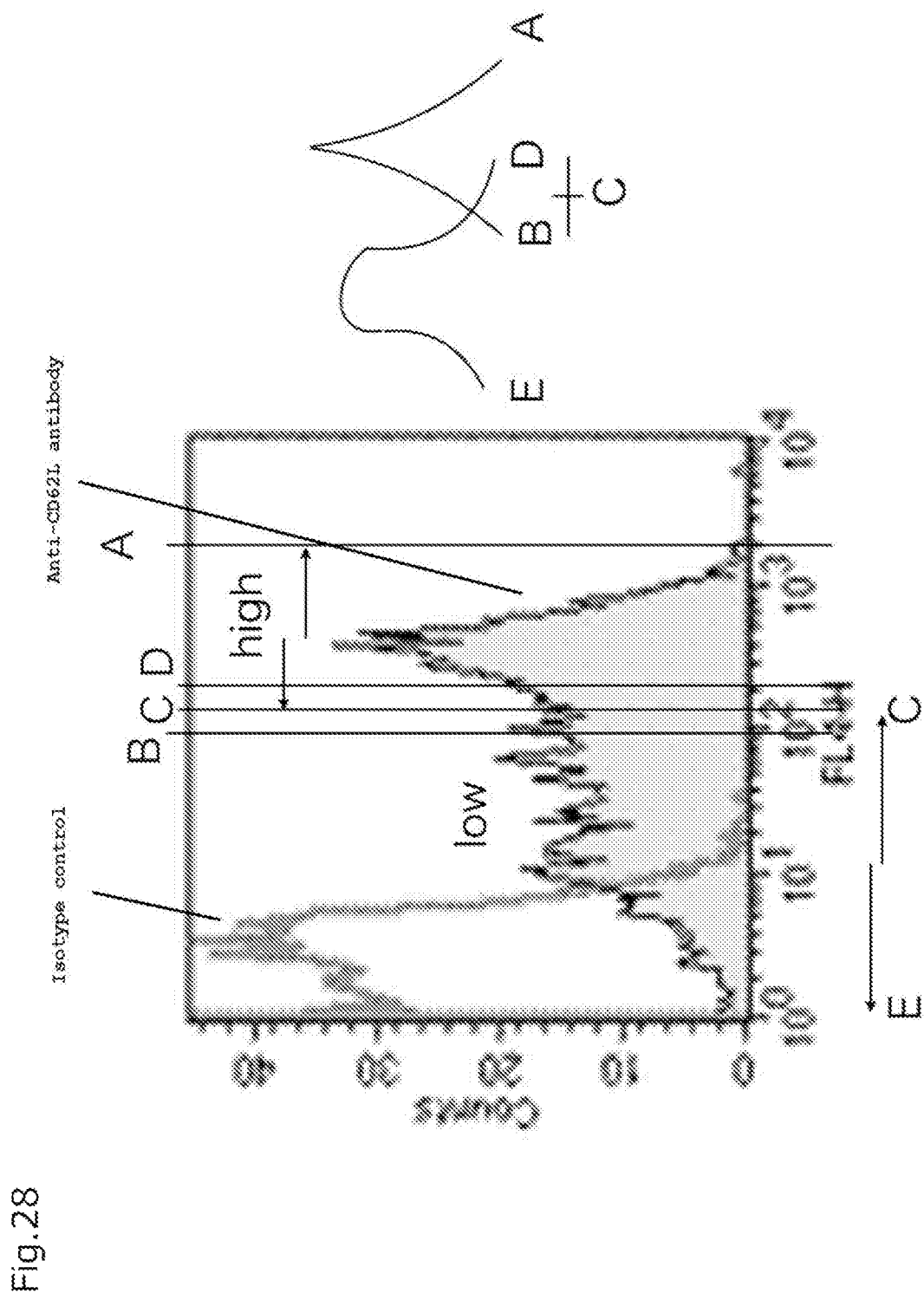

FIG. 28 is a diagram showing one example of a method of setting a threshold value of CD62L$^{low}$ and CD62L$^{high}$.

Figure 29:
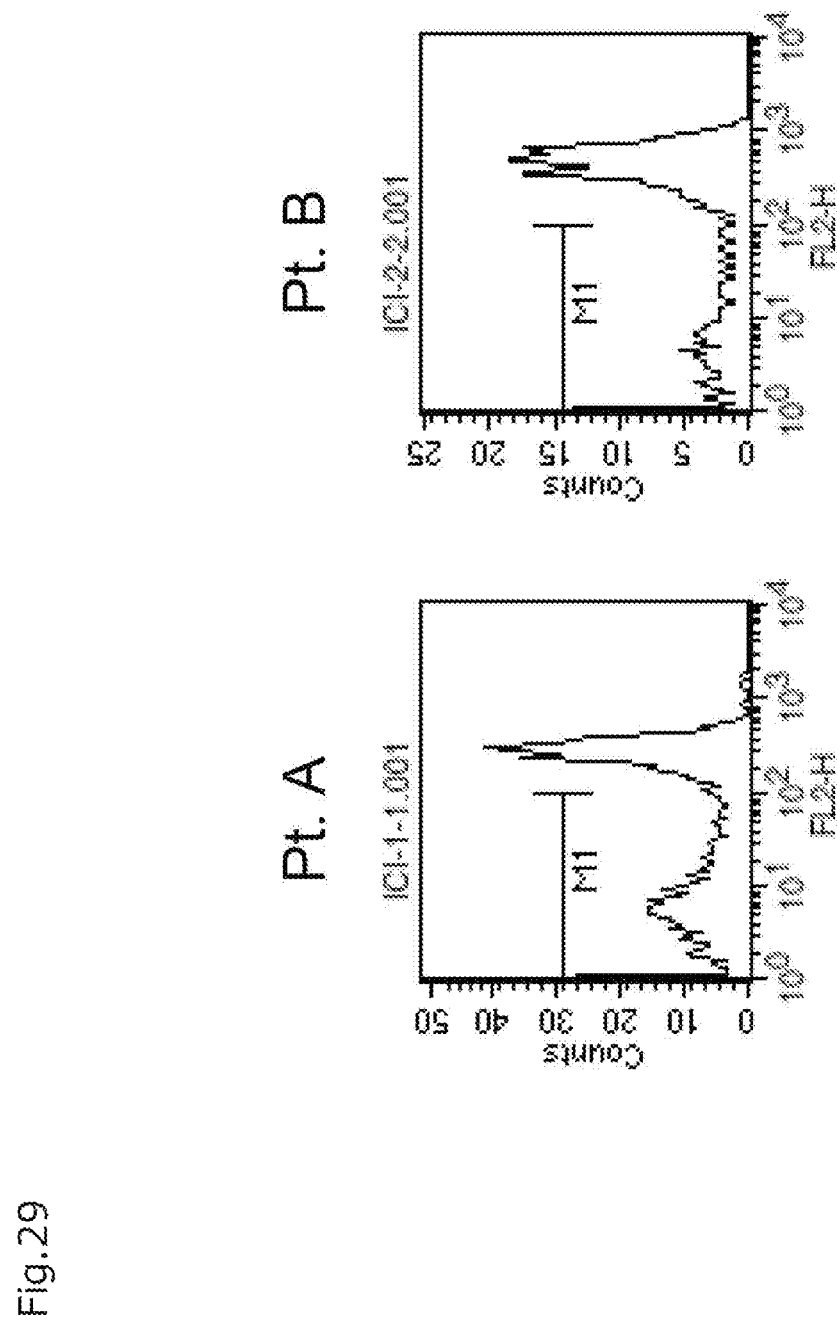

FIG. 29 is a histogram with respect to CD62L expression levels, which shows that CD62L low expression (CD62L$^{low}$) cells are clearly separated.

Figure 30:
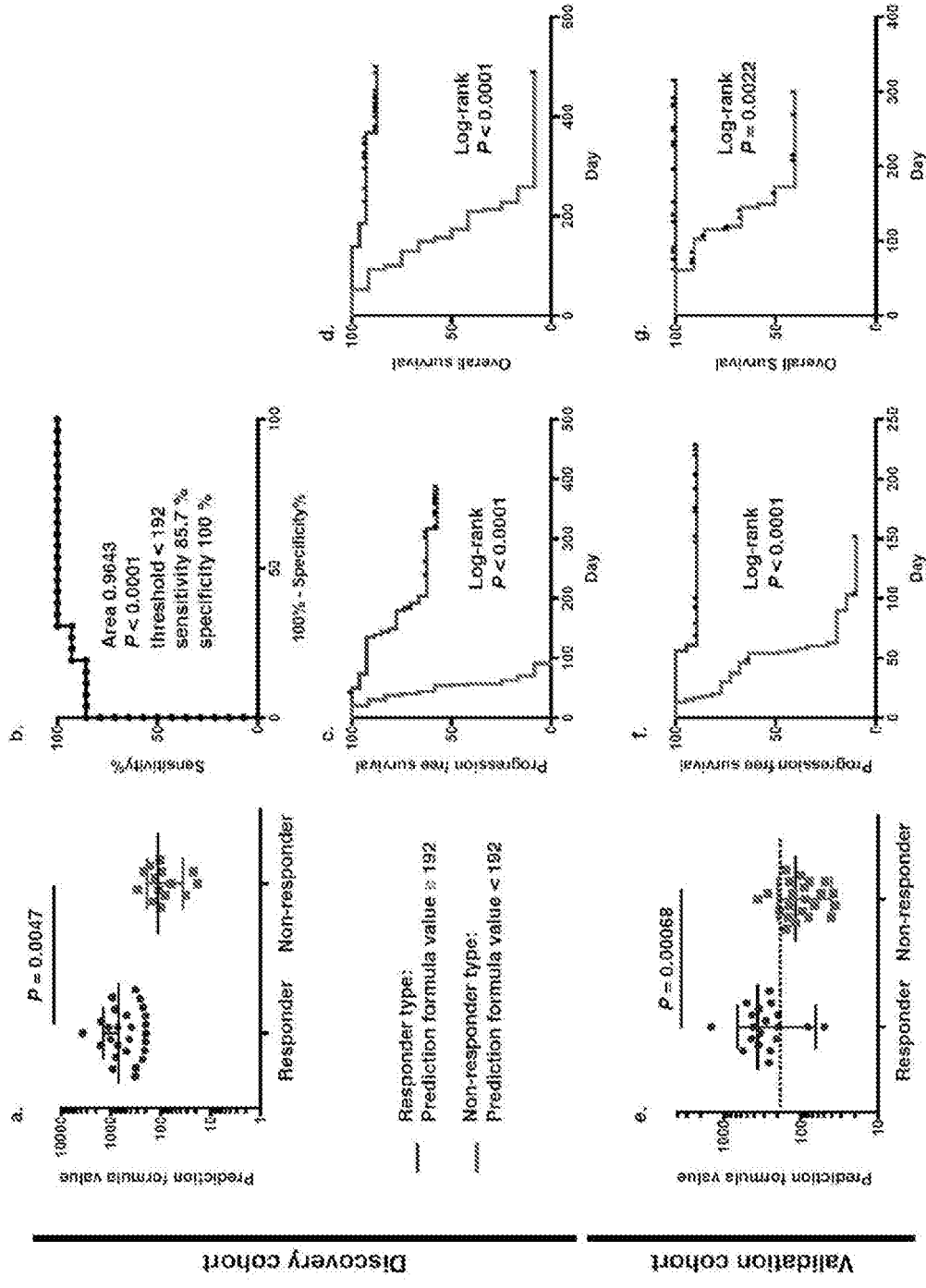

FIG. 30 is a diagram showing the prediction of treatment outcome in the discovery and validation cohorts. (a) Prediction formula values in the patient discovery cohort patients. Prediction formula, X$^2$/Y, was based on the percentages of CD62L$^{low}$ cells (X) and CD25$^+$FOXP3$^+$ cells (Y) in the total population of CD4+ cells. (b) The receiver operating characteristic curve of the prediction formula that predicted Non-responders in the discovery cohort (n=40). The sensitivity and specificity parameters at the threshold value of Prediction formula (192) were 85.7% and 100% (P<0.0001). (c) The progression-free survival (PFS) curves of the discovery cohort patients who were diagnosed as Non-responders or responders on the basis of the threshold value of Prediction formula (192). (d) Overall survival (OS) curves of the discovery cohort. (e) The values of the prediction formula in the validation cohort of patients. In these patients, peripheral blood mononuclear cells were examined before CT evaluation. (f) PFS curves of validation cohort patients. (g) OS curves of validation cohort patients. In panels a and e, data are presented as the mean±standard error of the mean and symbols indicate values from individual patients. Statistical significance of differences was assessed by the Student's two-tailed t-test (a,e) or log-rank test (b-d,f,g).

Figure 31:
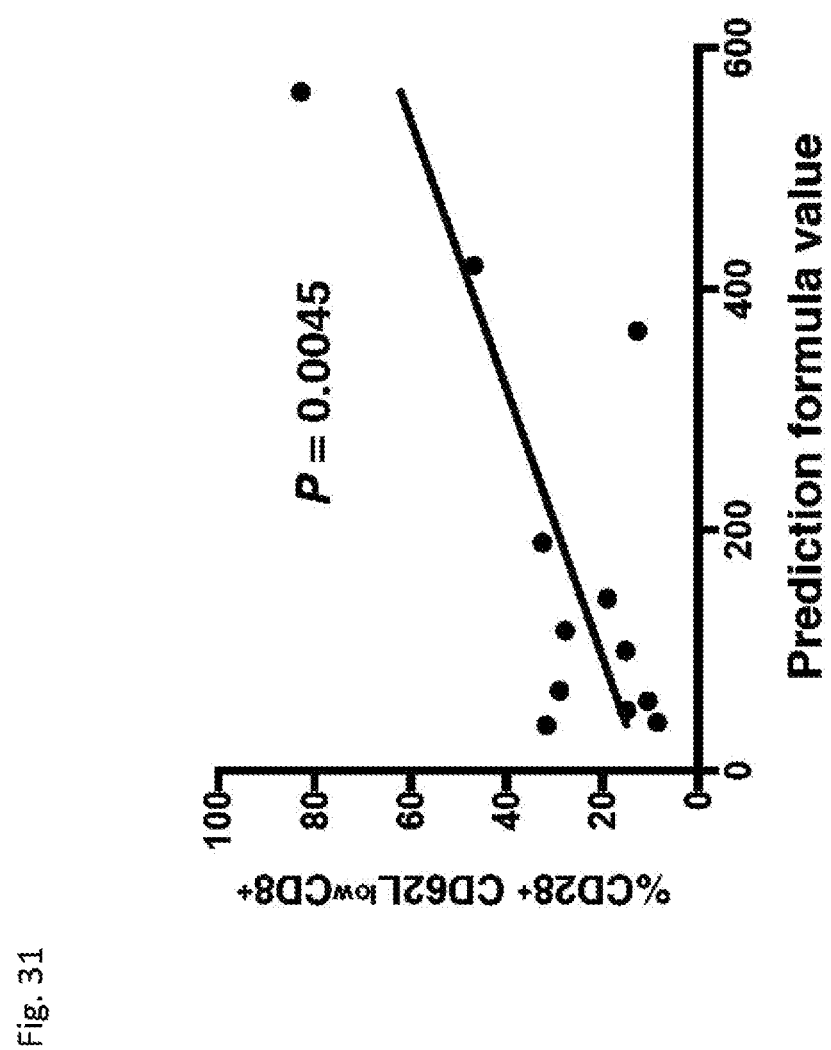

FIG. 31 is a diagram showing correlation between the percentage of CD28$^+$ cells in the total population of CD62L$^{low}$CD8$^+$ T-cells and prediction formula (X$^2$/Y, wherein X=the ratio of CD62L$^{low}$ T-cells in the CD4$^+$ T-cell population (%) and Y=the ratio of CD25$^+$FOXP3$^+$ T-cells in the CD4$^+$ T-cell population (%)) values (N=12).

Figure 32:
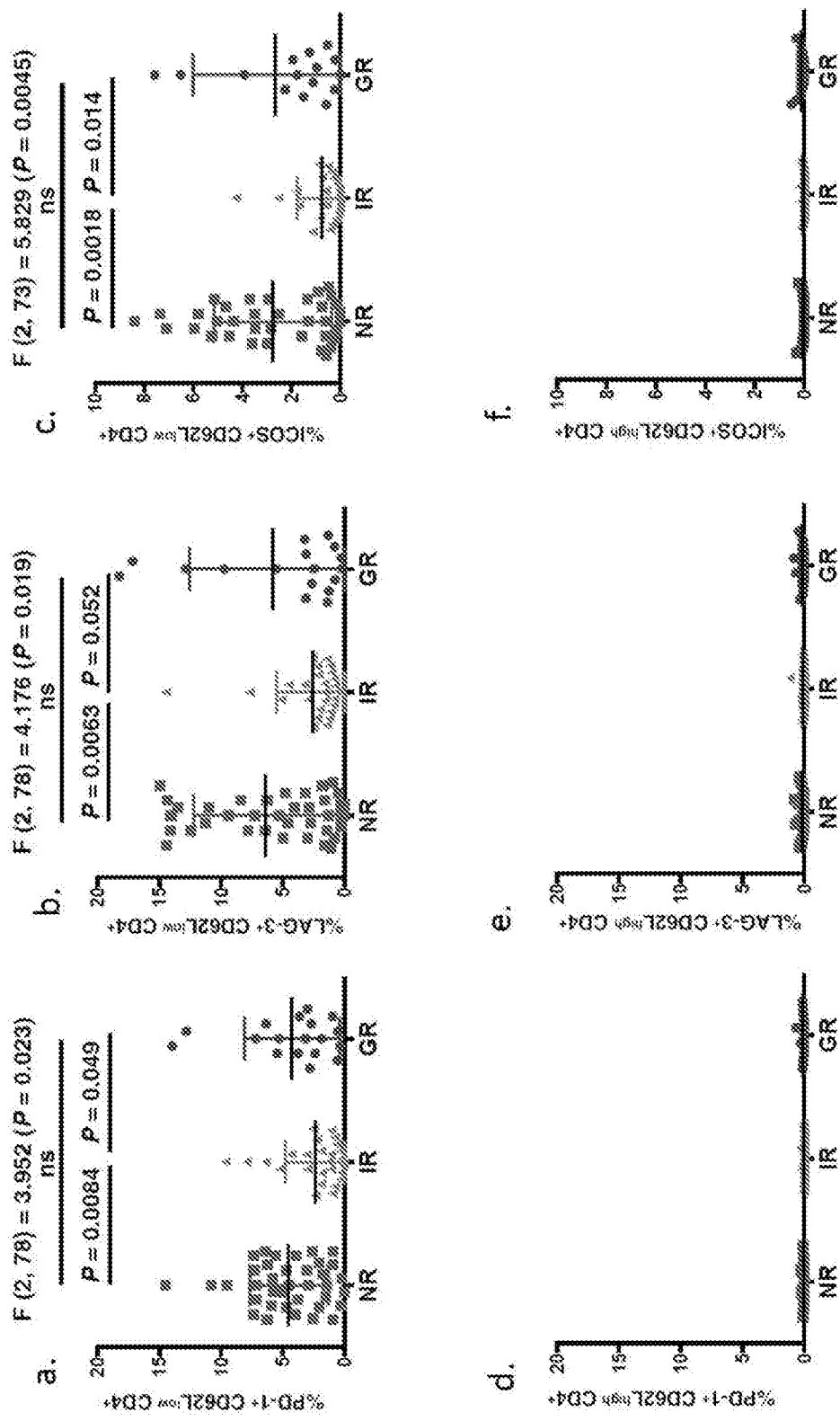

FIG. 32 shows differences in the percentages of T cell sub-populations and prediction formula values in patients with non-small cell lung cancer with different treatment outcomes. FACS (Fluorescence-activated cell sorting) results from peripheral blood samples of three subgroups of patients (N=81 in total) who were good responders (GR), intermediate responders (IR), and non-responders (NR) at 8 weeks during the first tumor response evaluation after Nivolumab treatment. The percentages of PD-1$^+$, LAG-3$^+$ and ICOS$^+$ cells in the total population of CD62L$^{low}$CD4$^+$ cells and CD62L$^{high}$CD4$^+$ cells are indicated in d-f, respectively. Data are presented as the means±standard error of the mean. Symbols indicate values from individual patients. Statistical significance of differences was assessed by one-way analysis of variance (ANOVA) and subsequent post hoc analysis (Two-stage step-up method of Benjamini, Krieger, and Yekutieli).

Figure 33:
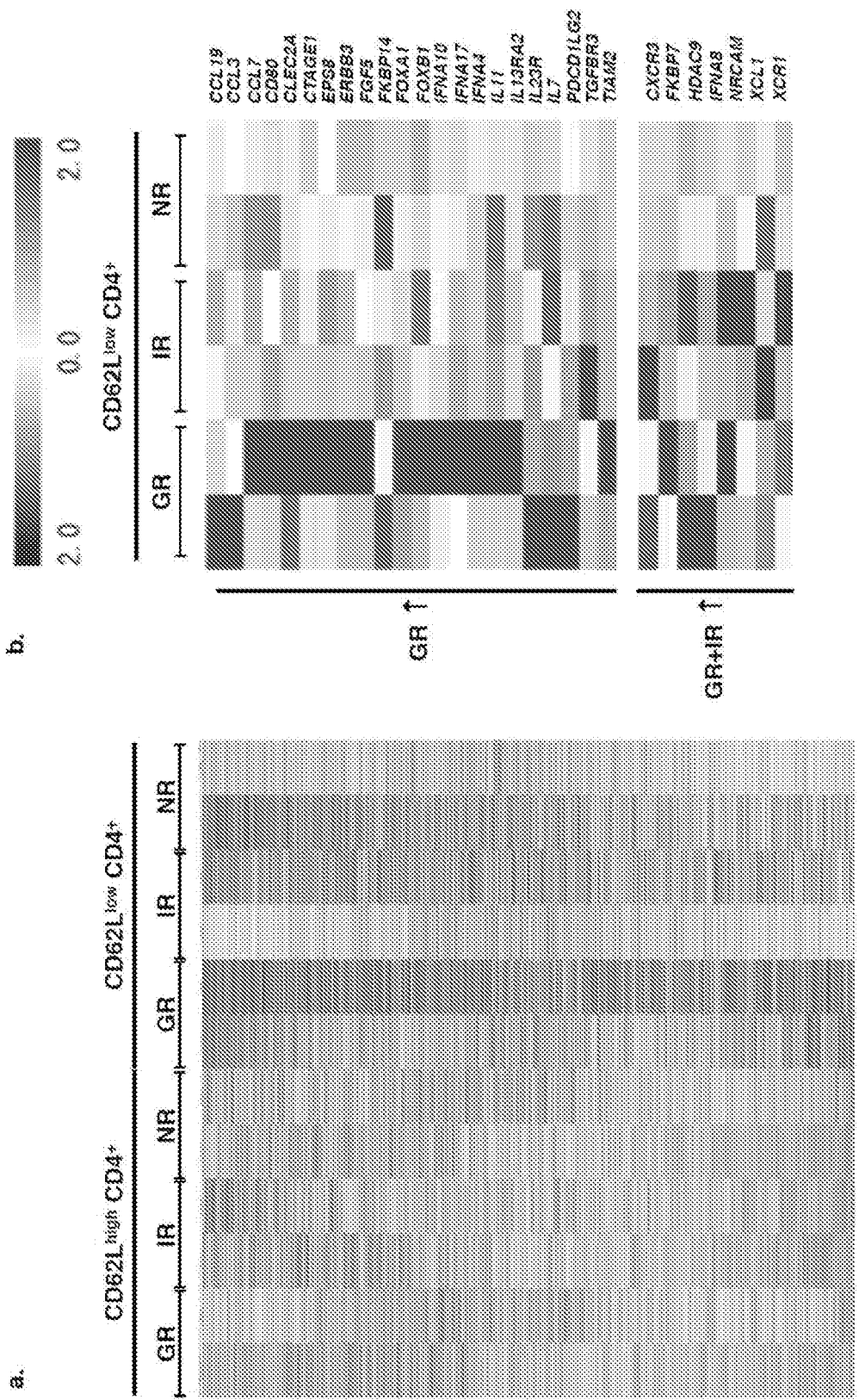

FIG. 33 is a diagram showing gene expression responsible for good response to Nivolumab treatment. FIG. 33a is signatures obtained by comparing gene expression data between CD62L$^{high}$CD4$^+$ and CD62L$^{low}$CD4$^+$ T cells from good responders (GR), intermediate responders (IR), and non-responders (NR). In FIG. 33b, among 39 genes well-known to be related to anti-tumor immunity in the above signatures, the gene expression of 29 is shown in terms of Nivolumab-treatment response. The degree of expression of the genes in CD62L$^{low}$CD4$^+$ T cells is shown, which indicates relatively higher gene expression in GR compared to IR and NR, and in GR and IR compared to NR, is depicted.

FIG. 34a shows immunity-related genes that showed differential expression between CD62L$^{low}$CD4$_+$ T cells and CD62L$^{high}$CD4$_+$ T cells, commonly in good, intermediate, and non-responder patients. It is considered that the recited genes can be used for distinction of cell subpopulations. FIG. 34b shows 53 genes that showed differential expressions related to the response to Nivolumab in CD62L$^{low}$CD4$^+$ T cells. It is understood that the recited genes can be used as markers for distinction of patient groups by examining their expression on CD62L$^{low}$CD4$^+$ T cells. Good responders: GR, intermediate responders: IR, and non-responders: NR.

FIG. 35 is a diagram showing the change of survival ratio in (1) Control group, (2) Antibody group, and (3) Antibody+ Cell group.

DESCRIPTION OF EMBODIMENTS

The present invention is disclosed hereinafter using exemplary Examples while referring to the appended drawings as needed. Throughout the entire specification, a singular expression should be understood as encompassing the concept thereof in the plural form, unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

(Definitions)

As used herein, "biomarker" refers to characteristics that can be objectively measured and evaluated as an indicator of a normal biological process, pathological process, or a pharmacological response to therapeutic intervention.

As used herein, "cancer" refers to malignant tumor, which is highly atypical, expands faster than normal cells, and can destructively infiltrate or metastasize surrounding tissue, or the presence thereof. In the present invention, cancer includes, but is not limited to, solid cancer and hematopoietic tumor.

As used herein, "cancer immunotherapy" refers to a method of treating cancer using a biological defense mechanism such as the immune mechanism of organisms.

As used herein, "anti-tumor immune response" refers to any immune response against tumor in a live organism.

As used herein, "dendritic cell stimulation in an anti-tumor immune response" refers to any phenomenon applying a stimulation to dendritic cells, which occurs in the process of an immune response against tumor in a live organism. Such stimulation can be a direct or indirect factor for inducing an anti-tumor immune response. Although not limited to the following, typically, a dendritic cell stimulation in an anti-tumor immune response is applied by CD4$^+$ T-cells (e.g., effector T-cells), resulting in dendritic cells stimulating CD8$^+$ T-cells, and the stimulated CD8$^+$ T-cells exerting an anti-tumor effect.

As used herein, "correlation" refers to two matters having a statistically significant correlated relationship For example, "relative amount of B correlated with A" refers to the relative amount of B being statistically significantly affected (e.g., increase or decrease) when A occurs.

As used herein, "cell subpopulation" refers to a cell population constituting a part of an entire cell population.

As used herein, the term "relative amount" with regard to cells can be interchangeably used with "ratio". Typically, the terms "relative amount" and "ratio" refer to the number of cells constituting a given cell subpopulation (e.g., CD62L$^{low}$CD4$^+$ T-cells) with respect to the number of cells constituting a specific cell population (e.g., CD4$^+$ T-cell population).

As used herein, "sensitivity" refers to the ratio of number of subjects having a given feature in selected targets to the total number of subjects with the given feature in a subject population when selecting a subject with the given feature from among a population of subjects, i.e., (number of subjects having a given feature in a selected target)/(total number of subjects with the given feature in a subject population).

As used herein, "specificity" refers to the ratio of the number of subjects with a given feature in selected targets to the total number of selected targets when selecting a subject with the given feature from among a population of subjects, i.e., (number of subjects with a given feature among selected targets)/(total number of selected targets).

As used herein, "ineffective group" refers to a group of subjects determined to be progressive (PD, Progressive disease) when a therapeutic effect upon undergoing cancer therapy is determined according to RECIST ver 1.1 at the early stage of up to about 9 weeks after start of the treatment. An ineffective group is also called a PD group, progressive group, or NR (Non-responder) which are interchangeably used herein.

As used herein, "partial response group" refers to a group of subjects determined to be partial response (PR, Partial response) when a therapeutic effect upon undergoing cancer therapy is determined according to RECIST ver 1.1. A partial response group is also called a PR group, which is interchangeably used herein.

As used herein, "stable group" refers to a group of subjects determined to be stable (SD, Stable disease) when a therapeutic effect upon undergoing cancer therapy is determined according to RECIST ver 1.1 at the early stage of up to about 9 weeks after start of the treatment. A "stable group" is also called an SD group or intermediate group, which are interchangeably used herein. Further, once the group turns into disease progression about 1 year after the disease control, this group is called IR (Intermediate Responder). Since most of this group is determined as SD about 9 weeks after the start of the treatment, "stable group" is also used interchangeably with IR (Intermediate Responder) group.

As used herein, "complete response group" refers to a group of subjects determined to be complete response (CR, Complete response) when a therapeutic effect upon undergoing cancer therapy is determined according to RECIST ver 1.1. A "complete response group" is also called a CR group, which is interchangeably used herein. The present invention detects a case where a population of subjects comprises a complete response group (CR) in addition to a partial response group (PR) and a case where a population of subjects comprises a complete response group (CR) without comprising a partial response group (PR) as the same as a partial response group (PR).

As used herein, "response group" is used when a "partial response group" and "complete response group" are collectively called. This is also called a "highly effective group". In addition, a group where a long term disease state control lasted for more than 1 year after starting the treatment is called GR (Good responder). However, since most of this group is identified as "partial response group" or "complete response group" 9 weeks after starting treatment, "response group" can also be used interchangeably with GR (Good responder) group.

As used herein, "relative value" refers to a value obtained by calculating a certain value while using another value as a baseline of comparison.

As used herein, the term "detection agent" broadly refers to all agents that are capable of detecting a substance of interest (e.g., cell surface marker or the like).

As used herein, the "amount" of a certain cell subpopulation encompasses the absolute number of certain cells and relative amount of a ratio in a cell population.

As used herein, "threshold value" refers to a value that is determined for a certain variable value, where the value gives a certain meaning when the changing value is greater or less than the value. A threshold value is also called a cut-off value herein.

As used herein, "ineffective group threshold value" refers to a threshold value used for identifying an ineffective group and stable group+response group in a given population of subjects. An ineffective group threshold value is selected to achieve a predetermined sensitivity and specificity when selecting an ineffective group in a given population of subjects.

As used herein, "response group threshold value" refers to a threshold value used for identifying a stable group and a response group in a given population of subjects or in a given population of subjects from which an ineffective group is removed using an ineffective group threshold value. A response threshold value is selected to achieve a predetermined sensitivity and specificity when selecting a response group in a given population of subjects or in a given population of subjects from which an ineffective group is removed using an ineffective group threshold value.

The term "about", when used to qualify a numerical value herein, is used to mean that the described value encompasses a range of values up to ±10%.

As used herein, "flow cytometry" refers to a technique of measuring the number of cells, individual or other biological particles suspended in a liquid and individual physical/chemical/biological attributes.

(Cancer Immunotherapy)

Cancer immunotherapy is a method of treating cancer using a biological defense mechanism of an organism. Cancer immunotherapy can be largely divided into cancer immunotherapy from strengthening the immune function against cancer and cancer immunotherapy from inhibiting the immune evasion mechanism of cancer. Cancer immunotherapy further includes active immunotherapy for activating the immune function in the body and passive immunotherapy for returning immune cells with an immune function activated or expanded outside the body into the body. The biomarker of the present invention is understood to evaluate the overall balance of the $CD4^+$ T-cell immunity to evaluate the overall tumor immunity itself, so that a therapeutic effect of all cancer immunotherapy can be broadly predicted.

Examples of cancer immunotherapy include non-specific immunopotentiators, cytokine therapy, cancer vaccine therapy, dendritic cell therapy, adoptive immunotherapy, non-specific lymphocyte therapy, cancer antigen specific T-cell therapy, antibody therapy, immune checkpoint inhibition therapy and the like. The Examples of the present specification demonstrate that the biomarker of the present invention accurately predicts a therapeutic effect of especially, although not limited to, immune checkpoint inhibition therapy.

PD-1 inhibitors are representative examples of immune checkpoint inhibitors. Examples of PD-1 inhibitors include, but are not limited to, anti-PD-1 antibody nivolumab (sold as Opdivo™) and pembrolizumab. In one preferred embodiment, nivolumab can be selected. Although not wishing to be bound by any therapy, one of the reasons that therapy using nivolumab is preferred is because the Examples demonstrate that the use of the biomarker of the present invention can clearly identify a responsive subject and a non-responsive subject, and especially because it is revealed that responsiveness and non-responsiveness can be clearly distinguished by a specific threshold value. Of course, it is understood that the biomarker of the present invention can be utilized for other PD-1 inhibitors to the same degree.

The present invention can also use PD-L1 inhibitors to the same extent as PD-1 inhibitors.

It is understood that anti-PD-1 antibodies achieve an anti-cancer effect by releasing the suppression of T-cell activation by a PD-1 signal. It is understood that anti-PD-L1 antibodies also achieve an anticancer effect by releasing the suppression of T-cell activation by a PD-1 signal. While the mechanism of PD-1 inhibiting a T-cell function is not fully elucidated, it is understood that an interaction between PD-1 (programmed death 1) and PD-L1 or PD-L2 recruits a tyrosine phosphatase, SHP-1 or 2, to the cytoplasmic domain of PD-1 to inactivate a T-cell receptor signaling protein ZAP70 to suppress activation of T-cells (Okazaki, T., Chikuma, S., Iwai, Y. et al.: A rheostat for immune responses: the unique properties of PD-1 and their advantages for clinical application. Nat. Immunol., 14, 1212-1218 (2013)). This is understood to be caused by the recruitment of SHP-1 or 2 to a part called an ITSM motif which dephosphorylates proximal signaling kinase of a T-cell receptor in the vicinity. In other words, the memory of "being stimulated by an antigen" is erased from a T-cell that has been stimulated by an antigen.

PD-1 is expressed at a high level in killer T-cells and natural killer cells, which have infiltrated a cancer tissue. It is understood that an immune response mediated by a PD-1 signal from PD-1 is attenuated by PD-L1 on tumor. While the immune response mediated by a PD-1 signal is attenuated by PD-L1, an effect of enhancing an anti-tumor immune response is attained by inhibiting an interaction between PD-1 and PD-L 1 and/or signaling induced by an interaction with an anti-PD-1 antibody.

A PD-L1 inhibitor (e.g., anti-PD-L1 antibodies avelumab, durvalumab, and atezolizumab) is another example of an immune checkpoint inhibitor.

PD-L1 inhibitors bind and inhibit the aforementioned PD-1 pathway to the PD-L1 side to inhibit an interaction between PD-1 and PD-L1 and/or signaling induced by an interaction to induce an anti-tumor immune response. Although not wishing to be bound by any therapy, subjects who are responsive or non-responsive to therapy that inhibits the PD-1 pathway (e.g., anti-PD-1 antibody or anti-PD-L1 antibody) can be clearly identified by using the biomarker of the present invention in view of the results demonstrated in the Examples.

A CTLA-4 inhibitor (e.g., anti-CTLA-4 antibody ipilimumab or tremelimumab) is another example of an immune checkpoint inhibitor.

CTLA-4 inhibitors activate T-cells to induce an anti-tumor immune response. T-cells are activated by an interaction of CD28 on the surface with CD80 or CD86. However, it is understood that surface expressed CTLA-4 (cytotoxic T-lymphocyte-associated antigen 4) preferentially interacts with CD80 or CD86 with higher affinity than CD20 to suppress activation, even for T-cells that have been activated. CTLA-4 inhibitors induce an anti-tumor immune response by inhibiting CTLA-4 to prevent inhibition of an interaction between CD20 and CD80 or CD86.

In another embodiment, an immune checkpoint inhibitor may target an immune checkpoint protein such as TIM-3 (T-cell immunoglobulin and mucin containing protein-3), LAG-3 (lymphocyte activation gene-3), B7-H3, B7-H4, B7-H5 (VISTA), or TIGIT (T cell immuno-receptor with Ig and ITIM domain).

It is understood that the aforementioned immune checkpoints also suppress an immune response to autologous tissue, but immune checkpoints increase in T-cells when an antigen such as a virus is present in vivo for an extended period of time. It is understood that tumor tissue is also an antigen which is present in vivo for an extended period of time, so that an anti-tumor immune response is evaded by such immune checkpoints. The aforementioned immune checkpoint inhibitors invalidate such an evasion function to achieve an anti-tumor effect. Although not wishing to be bound by any therapy, it is understood that the biomarker of the present invention evaluates the balance of the overall anti-tumor immune responses of humans so that it can be used as an indicator for accurately predicting a therapeutic effect of such an immune checkpoint inhibitor.

One embodiment of the present invention provides a composition comprising an immune checkpoint inhibitor. A composition comprising an immune checkpoint inhibitor can attain a significant therapeutic effect at a high probability by administration thereof to a subject who has been selected by evaluation with the biomarker of the present invention.

The composition comprising an immune checkpoint inhibitor of the present invention is generally administered systemically or locally in an oral or parenteral form.

The dosage varies depending on the age, body weight, symptom, therapeutic effect, administration method, treatment time or the like, but is generally administered, for example, orally one to several times a day in the range of 0.1 mg to 100 mg per dose per adult, or is administered parenterally (preferably intravenously) one to several times a day in the range of 0.01 mg to 30 mg per dose per adult or continuously administered intravenously in the range of 1 hour to 24 hours per day. Of course, the dosage varies depending on various conditions, so that an amount less than the above dosage may be sufficient or an amount exceeding the range may be required.

For administration, a composition comprising an immune checkpoint inhibitor can have a dosage form such as a solid agent or liquid agent for oral administration or an injection, topical agent, or suppository for parenteral administration. Examples of solid agents for oral administration include tablets, pills, capsules, powder, granules and the like. Capsules include hard and soft capsules.

The composition of the present invention includes one or more active ingredients (e.g., antibody to an immune checkpoint protein), which is directly used or is mixed with an excipient (lactose, mannitol, glucose, microcrystalline cellulose, starch, or the like), binding agent (hydroxypropyl cellulose, polyvinyl pyrrolidone, magnesium aluminometasilicate, or the like), disintegrant (calcium cellulose glycolate or the like), lubricant (magnesium stearate or the like), stabilizer, solubilizing agent (glutamic acid, aspartic acid, or the like), which is formulated in accordance with a conventional method for use. The composition may also be coated with a coating agent (refined sugar, gelatin, hydroxypropyl cellulose, hydroxypropyl methyl cellulose phthalate, or the like) or coated by two or more layers as needed. Capsules made of a substance that can be absorbed such as gelatin are also encompassed.

The composition of the present invention comprises a pharmaceutically acceptable aqueous agent, suspension, emulsion, syrup, elixir or the like when formulated as a liquid agent for oral administration. In such a liquid agent, one or more active ingredients is dissolved, suspended, or emulsified in a commonly used diluent (purified water, ethanol, a mixture thereof, or the like). Such a liquid agent may also contain a humectant, suspending agent, emulsifier, sweetener, flavor, fragrance, preservative, buffer, or the like.

Examples of injections for parenteral administration include a solution, suspension, emulsion, and solid injection that is used by dissolving or suspending it in a solvent at the time of use. An injection is used by dissolving, suspending or emulsifying one or more active ingredients into a solvent. Examples of solvents that are used include distilled water for injections, saline, vegetable oil, propylene glycol, polyethylene glycol, alcohols such as ethanol, combination thereof, and the like. Such an injection may also comprise a stabilizer, solubilizing agent (glutamic acid, aspartic acid, polysorbate 80™, or the like), suspending agent, emulsifier, analgesic, buffer, preservative, or the like. They are prepared by sterilizing or aseptic operation in the final step. It is also possible to manufacture an aseptic solid agent such as a lyophilized product, which is dissolved in sterilized or aseptic distilled water for injection or another solvent before use.

(Cancer)

Examples of target cancer in the present invention include, but are not limited to, melanoma (malignant melanoma), non-small cell lung cancer, renal cell cancer, malignant lymphoma (Hodgkin's or non-Hodgkin's lymphoma), head and neck cancer, urological cancer (bladder cancer, urothelial cancer, and prostate cancer), small cell lung cancer, thymic carcinoma, gastric cancer, esophageal cancer, esophagogastric junction cancer, liver cancer (hepatocellular carcinoma, intrahepatic cholangiocarcinoma), primary brain tumor (glioblastoma and primary central nervous system lymphoma), malignant pleural mesothelioma, gynecologic cancer (ovarian cancer, cervical cancer and uterine cancer), soft tissue sarcoma, cholangiocarcinoma, multiple myeloma, breast cancer, colon cancer and the like.

(Biomarker)

The present invention provides a novel biomarker for predicting a therapeutic effect of cancer immunotherapy. In one aspect, the T-cell composition of a subject is used as an indicator for predicting a therapeutic effect of cancer immunotherapy.

In one embodiment, a certain indicator of the T-cell composition of a subject at or greater than a response group threshold value indicates that the subject is a part of a response group to cancer immunotherapy. In another embodiment, a certain indicator of the T-cell composition of a subject at or less than a response group threshold value indicates that the subject is a part of a response group to cancer immunotherapy. In yet another embodiment, a certain indicator of the T-cell composition of a subject at or greater than an ineffective group threshold value indicates that the subject is a part of an ineffective group to cancer immunotherapy. In yet another embodiment, a certain indicator of the T-cell composition of a subject at or less than an ineffective group threshold value indicates that the subject is a part of an ineffective group to cancer immunotherapy.

Those skilled in the art can determine a suitable threshold value for each of such indicators. Those skilled in the art can predict a response to cancer immunotherapy of a subject at the indicated sensitivity and/or specificity by using the threshold value (ineffective group threshold value and/or response group threshold value) disclosed herein.

For the indicators disclosed herein, those skilled in the art can appropriately determine a threshold value that would achieve a desired sensitivity and specificity from results of determining an effect of cancer immunotherapy of a reference subject group. The group of subjects who are proven in the Examples of the present specification can be considered as a reference subject group. In other words, those skilled in the art can determine a threshold value from the results of experiments disclosed in the Examples or determine a new threshold value from results of a reference subject population upon practicing the present invention.

Sensitivity refers to the ratio of the number of subjects with a given feature in selected targets to the total number of subjects with the given feature in a population of subjects when selecting subjects with the given feature from among the population of subjects. For example, sensitivity is 100% when all subjects with a given feature in a population of subjects are selected. The sensitivity is 50% when half of subjects with a given feature in a population of subjects are selected. The sensitivity is 0% when none of the subjects with a given feature in a population of subjects are selected. Sensitivity is determined as, for example, (number of subjects with a given feature among selected targets)/(total number of subjects with a given feature in a subject population). Determination with high sensitivity means that when it is desirable to find a subject with a certain condition (e.g., ineffective group with respect to cancer immunotherapy), such a subject is likely to be definitively determined as being in such a condition.

The biomarker of the present invention which enables determination at high sensitivity is very useful for ensuring the discovery of an ineffective group with respect to a certain therapy. It is also possible to select a threshold value so that sensitivity would be high in accordance with such an objective.

Specificity refers to the ratio of the number of subjects with a given feature in selected targets to the total number of selected targets when selecting a subject with the given feature from among a population of subjects. For example, specificity is 100% when all candidates selected from among a subject population have the given feature.

The specificity is 50% when half of the candidates selected from among a subject population have the given feature. The specificity is 0% when none of the candidates selected from among a subject population have the given feature. Specificity is determined as, for example, (number of subjects with a given feature among selected targets)/(total number of selected targets). Determination with high specificity means that the probability of incorrectly determining a subject who is not in a certain condition (e.g., response group with respect to cancer immunotherapy) as not being in such a condition (e.g., response group with respect to cancer immunotherapy) is low.

The biomarker of the present invention which enables determination with high specificity is useful, for example for preventing a determination that would incorrectly determine a response group to a certain therapy as an ineffective group to discontinue therapy. It is also possible to select a threshold value so that specificity would be high in accordance with such an objective.

For example, when identifying a subject as a part of an ineffective group with an indicator at or below a certain threshold value (ineffective group threshold value) when an increase of the indicator is correlated with the effect of cancer immunotherapy, subjects who are determined to be not a part of an ineffective group (i.e., stable group or response group) despite being a part of an ineffective group decreases (sensitivity increases) for threshold values that are set higher, but subjects who are determined as a part of an ineffective group despite not being an ineffective group (e.g., stable group or response group) increases (decrease in specificity). In contrast, subjects who are determined as a part of an ineffective group despite not being a part of an ineffective group (i.e., stable group or response group) decreases (specificity increases) for threshold values that are set lower, but subjects who are determined as not a part of an ineffective group (i.e., stable group or response group) despite being a part of an ineffective group increases (sensitivity decreases).

For the biomarker of the present invention, a threshold value can be set and used so that specificity and/or sensitivity is very high, so that the biomarker of the present invention can be used as an unprecedented and advantageous marker for predicting a therapeutic effect of cancer immunotherapy. Those skilled in the art can also suitably set a threshold value in accordance with the objective in such a range of threshold values at which both the specificity and sensitivity are very high. It should be understood that a proximate value of a specific value can be used as long as determination of interest can be performed even when a specific value is shown as an example of a threshold value.

The ratio of $CD62L^{low}$ T-cells in $CD4^+$ T-cells of a subject can be used as an indicator for predicting a response to cancer immunotherapy of the subject, e.g., as an indicator for selecting an ineffective group. The inventors have discovered that the ratio of $CD62L^{low}$ T-cells in $CD4^+$ T-cells higher than an ineffective group threshold value can predict at a very high precision that the subject is not a part of an ineffective group to cancer immunotherapy in such a case.

An ineffective group threshold value for the ratio of $CD62L^{low}$ T-cells in $CD4^+$ T-cells can be appropriately determined by those skilled in the art based on a reference, or a threshold value (Cutoff) shown in FIG. 6 can be used as an ineffective group threshold value. It should be noted that the ratio may be denoted hereinafter as percent (%).

For example, when using 19.4 as an ineffective group threshold value in the results of FIG. 6, it is understood that the ratio of $CD62L^{low}$ T-cells in $CD4^+$ T-cells can be used as a biomarker for determining whether a subject is a part of an ineffective group with sensitivity of 92.9% and specificity of 96.7%.

When similarly using a value of 14.45 or less (e.g., 14.45, 13.8, 13.3, 12.3, or 10.9) as an ineffective group threshold value for the ratio of $CD62L^{low}$ T-cells in $CD4^+$ T-cells in the results of FIG. 6, an ineffective group can be predicted with the ratio as a biomarker with 100% specificity.

When using a value of 22.55 or greater (e.g., 23.1, 24.1, 24.8, 25.05, 25.45, 25.95, 27, 28.75, or the like) as an ineffective group threshold value for the ratio of $CD62L^{low}$ T-cells in $CD4^+$ T-cells, an ineffective group can be predicted with the ratio as a biomarker with 100% sensitivity.

In other words, an ineffective group threshold value as a ratio of $CD62L^{low}$ T-cells in $CD4^+$ T-cells can be in the range of about 10 to about 30 (%). Examples of such an ineffective group threshold value include about 10, 11, 12, 13, 14, 15, 16, 17, 18, 19, 20, 21, 22, 23, 24, 25, 26, 27, 28, 29, and 30 (%).

The ratio of $Foxp3^+CD25^+$ T-cells in $CD4^+$ T-cells of a subject can also be used as an indicator for predicting a response to cancer immunotherapy of the subject, such as an ineffective group threshold value. The inventors have discovered that a ratio of $Foxp3^+CD25^+$ T-cells in $CD4^+$ T-cells in a subject derived sample lower than an ineffective group threshold value indicates that the subject is not a part of an ineffective group with respect to cancer immunotherapy.

The ineffective group threshold value for a ratio of $Foxp3^+CD25^+$ T-cells in $CD4^+$ T-cells of a subject can be appropriately determined by those skilled in the art from a reference subject. Such an ineffective group threshold value can be in a range of about 2 to about 4 (%). Examples of threshold values include about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 (%).

Indicators of the T-cell composition disclosed herein can be used in combination when preferred. Since the inventors have discovered that multiple indicators independently exhibit correlation with responsiveness, it is understood that multiple indicators, which are combined and used as an indicator for responsiveness, can further improve the precision of prediction.

When two or more indicators are combined as an indicator of responsiveness, an indicator represented by a formula using any number of variables can be used. When multiple indicators ($X_1, X_2, X_3 \ldots X_n$) are used, examples of indicators of responsiveness include but are not limited to the following:

$$F = a_1 X_1^{b1} + a_2 X_2^{b2} + a_3 X_3^{b3} \ldots + a_n X_n^{bn}$$

$$F = X_1^{c1} * X_2^{c2} * X_3^{c3} \ldots * X_n^{cn}$$

wherein each of a, b, and c is any real number. Responsiveness can be predicted from the magnitude of the indicator that is calculated by such a formula. Multivariate analysis by logistic regression or discriminant analysis can be performed on the novel indicators discovered by the inventors to determine a coefficient for use as an indicator of responsiveness to cancer immunotherapy of a subject.

While indicators that are combined are not limited, the inventors have discovered indicators such as the amount of a CD4$^+$ T-cell subpopulation correlated with a dendritic cell stimulation in an anti-tumor immune response, amount of a dendritic cell subpopulation correlated with a dendritic cell stimulation in an anti-tumor immune response, the amount of a CD8$^+$ T-cell subpopulation correlated with a dendritic cell stimulation in an anti-tumor immune response, amount of regulatory T-cells or a CD4$^+$ T-cell subpopulation correlated with regulatory T-cells, and amount of an ICOS$^+$CD62L$^{low}$CD4$^+$ T-cell subpopulation. Indicators that predict responsiveness by different mechanisms can be combined for use as an indicator exhibiting stronger correlation with responsiveness, which is not false correlation.

For example, two or more indicator, such as three, four, five, or more indicators, that are selected from the group consisting of:
 an amount of a CD62L$^{low}$CD4$^+$ T-cell subpopulation;
 an amount of a CCR7$^-$CD4$^+$ T-cell subpopulation;
 an amount of a LAG-3$^+$CD62L$^{low}$CD4$^+$ T-cell subpopulation;
 an amount of an ICOS$^+$CD62L$^{low}$CD4$^+$ T-cell subpopulation;
 an amount of a CD45RA$^-$CD4$^+$ T-cell subpopulation;
 an amount of a CD45RO$^+$CD4$^+$ T-cell subpopulation;
 an amount of an HLA-DR$^+$ dendritic cell subpopulation;
 an amount of a CD80$^+$ dendritic cell subpopulation;
 an amount of a CD86$^+$ dendritic cell subpopulation;
 an amount of a PD-L1$^+$ dendritic cell subpopulation;
 an amount of a CD62L$^{low}$CD8$^+$ T-cell subpopulation;
 an amount of a CD137$^+$CD8$^+$ T-cell subpopulation;
 an amount of a CD28$^+$CD62L$^{low}$CD8$^+$ T-cell subpopulation;
 an amount of a CCR4$^+$CD25$^+$CD4$^+$ T-cell subpopulation;
 an amount of a CD62L$^{high}$CD25$^+$CD4$^+$ T-cell subpopulation;
 an amount of a CD127$^+$CD25$^+$CD4$^+$ T-cell subpopulation;
 an amount of CD45RA$^-$Foxp3$^+$CD4$^+$ T-cell subpopulation; and
 an amount of CD4$^+$Foxp3$^+$CD25$^+$ T-cell subpopulation;
can be used in combination.

It is possible to show that a subject is not a part of an ineffective group with respect to cancer immunotherapy by combining indicators, as responsiveness to cancer immunotherapy. Similarly, it is possible to determine that a subject is a part of a response group with respect to response to cancer immunotherapy by combining indicators, as responsiveness to cancer immunotherapy.

Typically, responsiveness can be predicted by formula F(X, Y) using two indicators (X, Y) disclosed herein as variables. In some cases, a formula is a relative value of X to Y.

Any function of X and Y (F(X, Y)) can be used as a relative value of X to Y. Especially when it is understood that X is positively correlated with responsiveness and Y is negatively correlated with responsiveness, any function of X and Y (F(X, Y)), which monotonically increases with respect to X and monotonically decreases with respect to Y, can be used, but the formula is not limited thereto. With two or more variables representing responsiveness, a formula representing responsiveness can be found by regression from logistic regression or the like by calculating the contribution of each variable to responsiveness.

Examples of F(X, Y) representing responsiveness include, but are not limited to the following.

$$F = aX^r + bY^s$$

$$F = X^r * Y^s$$

wherein a, b, r, and s are any real numbers.

Integers can be used as r and s for simplicity of the formula. In some embodiments, examples of relative values of X to Y include, but are not limited to, $X^n/Y^m$ (n and m are any integer) such as X/Y and $X^2$/Y.

When each of factors X and Y indicates responsiveness to therapy from different mechanisms, combination of such indicators can make the prediction of responsiveness more accurate. The study by the inventors shows that a formula with r and s in the range of −5 to 5 can be used to accurately predict responsiveness to cancer immunotherapy of a subject.

In one embodiment, a subject can be shown to be not a part of an ineffective group with respect to cancer immunotherapy by using the amount of T-cells correlated with a dendritic cell stimulation in an anti-tumor immune response as X and the amount of regulatory T-cells or a CD4$^+$ T-cell subpopulation correlated with regulatory T-cells as Y. In this case, it is demonstrated that responsiveness to cancer immunotherapy of a subject can be accurately predicted using a formula with r and s in the range of −5 to 5. Examples of such a formula include X/Y, $X^2$/Y, $X^3$/Y, $X^4$/Y, $X^5$/Y, X/$Y^2$, $X^2/Y^2$, $X^3/Y^2$, $X^4/Y^2$, $X^5/Y^2$, X/$Y^3$, $X^2/Y^3$, $X^3/Y^3$, $X^4/Y^3$, $X^5/Y^3$, X/$Y^4$, $X^2/Y^4$, $X^3/Y^4$, $X^4/Y^4$, $X^5/Y^4$, X/$Y^5$, $X^2/Y^5$, $X^3/Y^5$, $X^4/Y^5$, $X^5/Y^5$, and the like.

Examples of the present specification show that F=$X^{2.475}$/Y can be used as an indicator by logistic regression for a combination of the amount of CD62L$^{low}$ T-cells in CD4$^+$ T-cells of a subject (X) and the amount of Foxp3$^+$CD25$^+$ T-cells in CD4$^+$ T-cells (Y), but those skilled in the art can appropriately derive a different combination or a different formula for the indicators disclosed herein by a similar analysis.

In regression analysis, a result from a sample greater than the number of combined variables +1 can be used to calculate a coefficient in a formula of a combination of variables. When a form of formula in a combination of two indicators is found by regression analysis, regression analysis is performed using a result in at least four samples. Preferably, regression analysis is performed using results in 20 or more samples. More preferably, regression analysis is performed using results in 30 or more samples. Regression analysis with a greater number of samples can be advantageous in that a combination of indicators that predicts responsiveness of a subject more accurately can be found.

In one embodiment, the amount of CD62L$^{low}$ T-cells in CD4$^+$ T-cells of a subject (X) and the amount of Foxp3$^+$ CD25$^+$ T-cells in CD4$^+$ T-cells (Y) can be used as an ineffective threshold value as a combined indicator. For example, a relative value of X to Y can be used as an indicator for predicting a response with respect to cancer immunotherapy of a subject.

For example, the present invention can calculate variables (X, Y), with a value selected from the group consisting of
an amount of a CD62L$^{low}$CD4$^+$ T-cell subpopulation;
an amount of a CCR7$^-$CD4$^+$ T-cell subpopulation;
an amount of a LAG-3$^+$CD62L$^{low}$CD4$^+$ T-cell subpopulation;
an amount of an ICOS$^+$CD62L$^{low}$CD4$^+$ T-cell subpopulation;
an amount of a CD45RA$^-$CD4$^+$ T-cell subpopulation;
an amount of a CD45RO$^+$CD4$^+$ T-cell subpopulation;
an amount of an HLA-DR$^+$ dendritic cell subpopulation;
an amount of a CD80$^+$ dendritic cell subpopulation;
an amount of a CD86$^+$ dendritic cell subpopulation;
an amount of a PD-L1$^+$ dendritic cell subpopulation;
an amount of a CD62L$^{low}$CD8$^+$ T-cell subpopulation;
an amount of a CD137$^+$CD8$^+$ T-cell subpopulation; and
an amount of a CD28$^+$CD62L$^{low}$CD8$^+$ T-cell subpopulation; as (X).

The method of the present invention can also calculate variables (X, Y), with the amount of a regulatory T cell subpopulation or a CD4$^+$ T cell subpopulation correlated with regulatory T cells as (Y). The method of the present invention can also calculate variables (X, Y), with a value selected from the group consisting of:
an amount of CCR4$^+$CD25$^+$CD4$^+$ T-cell subpopulation;
an amount of CD62L$^{high}$CD25$^+$CD4$^+$ T-cell subpopulation;
an amount of CD127$^+$CD25$^+$CD4$^+$ T-cell subpopulation;
an amount of CD45RA$^-$Foxp3$^+$CD4$^+$ T-cell subpopulation; and
an amount of CD4$^+$Foxp3$^+$CD25$^+$ T-cell subpopulation; as (Y).

The present invention further provides a method of identifying a response group (PR) and stable group (SD) in a subject population determined not to be a part of an ineffective group using the above (X, Y). A method of identifying the response group (PR) and stable group (SD) can predict whether a subject is a part of the response group (PR) or stable group (SD) by calculate variables (Z, W), with
an amount of an ICOS$^+$CD62L$^{low}$CD4$^+$ T-cell subpopulation as (Z) and a value selected from the group consisting of
an amount of a CD4$^+$CD25$^+$ T-cell subpopulation;
an amount of a CD4$^+$Foxp3$^+$ T-cell subpopulation;
an amount of a CD4$^+$Foxp3$^+$CD25$^+$ T-cell subpopulation;
an amount of a CD62L$^{high}$CD25$^+$CD4$^+$ T-cell subpopulation;
an amount of a CD45RA$^-$Foxp3$^+$CD4$^+$ T-cell subpopulation;
an amount of a CCR4$^+$CD25$^+$CD4$^+$ T-cell subpopulation; and
an amount of a CD127$^+$CD25$^+$CD4$^+$ T-cell subpopulation; as (W).

The relative value of X to Y is not particularly limited, but any function of X and Y (F(X, Y)), which monotonically increases with respect to X and monotonically decreases with respect to Y, can be used. For example, such a function can be $$F(X,Y)=G(X)/H(Y); \text{ or}$$

$$F(X,Y)=G(X)-H(Y)$$

wherein G(X) and H(Y) can be monotonically increasing functions with respect to X and Y, respectively. For example, G(X) can be $X^R$, $\log_R X$, $R^X$, or the like, wherein R is any real number satisfying the condition and is preferably a positive integer. For example, H(Y) can be $Y^R$, $\log_R Y$, or $R^Y$, or the like, wherein R is any real number satisfying the condition and is preferably a positive integer. In such a form, the accuracy of prediction can be improved by using a positive prediction for a therapeutic effect of cancer immunotherapy of X in combination with a negative prediction for cancer immunotherapy of Y as an indicator.

Examples of relative values of X to Y include, but are not limited to, $X^n/Y^m$ (n and m are any positive real numbers) such as X/Y and $X^2/Y$. When each of factors X and Y indicates responsiveness to therapy from different mechanisms, combination of such indicators can make the prediction of responsiveness more accurate.

A function using Z and W is not particularly limited. Any function of Z and W (J(Z, W)) can be used. Examples of such a function can be $$J(Z,W)=K(Z)*L(W); \text{ or}$$

$$J(Z,W)=K(Z)+L(W)$$

wherein K(Z) and L(W) can typically be functions which monotonically increase with respect to Z and W, respectively. For example, K(Z) can be $Z^R$, $\log^R Z$, $R^Z$, or the like, wherein R is any real number satisfying the condition and is preferably a positive integer. For example, L(W) can be $W^R$, $\log^R W$, $R^W$, or the like, wherein R is any real number satisfying the condition and is preferably a positive integer. Based on J(Z, W), accuracy of determination of a response group (PR) and stable group (SD) in an ineffective group can be improved. Examples of relative values of Z to W include, but are not limited to, $Z^n*W^m$ (wherein n and m are any real number), such as $W^5*Z$. When each of factors Z and W indicates responsiveness to therapy from different mechanisms, combination of such indicators can make the prediction of responsiveness more accurate.

When the amount of CD62L$^{low}$ T-cells in CD4$^+$ T-cells is X and the amount of Foxp3$^+$CD25$^+$ T-cells in CD4$^+$ T-cells is Y, X/Y can be used as an indicator for predicting a response to cancer immunotherapy of a subject. The inventors have discovered that a subject with a high X/Y is shown to be not a part of an ineffective group with respect to cancer immunotherapy. Thus, a value of X/Y can be used as an ineffective group threshold value.

An ineffective group threshold value for X/Y can be appropriately determined by those skilled in the art based on a reference, or a value (Cutoff) shown in FIG. 8 can be used as an ineffective group threshold value.

When 7.35 is used as an ineffective group threshold value of X/Y, an ineffective group can be predicted using X/Y as a biomarker for determining whether a subject is a part of an ineffective group with sensitivity of 71.4% and specificity of 100%.

When a value of 7.35 or less (e.g., 7.35, 6.83, 6.31, 5.64, 5.01, or the like) is used as an ineffective group threshold value of X/Y, this can predict an ineffective group as a biomarker with specificity of 100%.

When a value of 9.305 or greater (e.g., 9.895, 10.19, 11.71, 12.07, 12.32, 12.42, or the like) is used as an ineffective group threshold value of X/Y, this can predict an ineffective group as a biomarker with sensitivity of 100%.

In other words, an ineffective group threshold value of X/Y can be in the range of about 5 to about 13. Examples of an ineffective group threshold value of X/Y include about 5, 6, 7, 8, 9, 10, 11, 12, and 13.

Furthermore, as a relative value of X to Y, $X^2/Y$ can be used as an ineffective group threshold value, which is an indicator for predicting a response to cancer immunotherapy of a subject. The inventors have discovered that a subject with high $X^2/Y$ is shown to be highly unlikely a part of an ineffective group with respect to cancer immunotherapy.

An ineffective group threshold value for $X^2/Y$ can be appropriately determined by those skilled in the art based on a reference, or a threshold value (Cutoff) shown in FIG. 10 can be used as an ineffective group threshold value.

When 174.3 is used as an ineffective group threshold value for $X^2/Y$, $X^2/Y$ can predict an ineffective group as a biomarker for determining whether a subject is a part of an ineffective group with sensitivity and specificity both at 100%.

110.6, 118.2, 134.9, 151.6, 157.4, 174.3, 194.2, 202.3, 208.3, and the like can be used as other values of ineffective group threshold values for $X^2/Y$.

In other words, an ineffective group threshold value for $X^2/Y$ can be in the range of about 110 to about 210. Examples of ineffective group threshold values for $X^2/Y$ include about 110, 120, 130, 140, 150, 160, 170, 180, 190, 200, and 210.

Those skilled in the art can use other relative values of X to Y by setting an appropriate threshold value at least from the data disclosed herein.

It is also possible to distinguish PR and SD (show that a subject is part of a response group) using results of calculating (e.g., multiplying) two or more indicators (biomarkers, BM) of the present invention. In one embodiment, a value of $Z^n*W^m$ (n and m are positive real numbers), with a first biomarker as "Z" and a second biomarker as "W", can be used to distinguish PR and SD, but this is not limited thereto. It is also possible to use results from calculating (e.g., adding and/or multiplying) three or more biomarkers for distinguishing PR and SD. For example, when a PR group and an SD group are distinguished using the product W*Z of the ratio of CD25$^+$Foxp3$^+$CD4$^+$ T-cells in CD4$^+$ T-cells (W) and the ratio of ICOS$^+$CD62L$^{low}$CD4$^+$ T-cells in CD62L$^{low}$CD4$^+$ T-cells (Z), it was demonstrated that a threshold value of W*Z of 1.816 can be used as a biomarker with sensitivity of 80% and specificity of 89.5% (bottom figure in the middle of FIG. 21). Alternatively, it was demonstrated that $Z*W^5$ can be used as a biomarker with sensitivity of 54.55% and specificity of 100%.

In addition, any function of Z and W (J(Z, W)) can be used as disclosed above. For example, a formula such as $J=Z^r*W^s$ with r and s in the range of −5 to 6 can be used to accurately predict the responsiveness to cancer immunotherapy of a subject. Examples of such a formula include $Z*W$, $Z^2*W$, $Z^3*W$, $Z^4*W$, $Z^5*W$, $Z^6*W$, $Z*W^2$, $Z^2*W^2$, $Z^3*W^2$, $Z^4*W^2$, $Z^5*W^2$, $Z^6*W^2$, $Z*W^3$, $Z^2*W^3$, $Z^3*W^3$, $Z^4*W^3$, $Z^5*W^3$, $Z^6*W^3$, $Z*W^4$, $Z^2*W^4$, $Z^3*W^4$, $Z^4*W^4$, $Z^5*W^4$, $Z^6*W^4$, $Z*W^5$, $Z^2*W^5$, $Z^3*W^5$, $Z^4*W^5$, $Z^5*W^5$, $Z^6*W^5$, $Z*W^6$, $Z^2*W^6$, $Z^3*W^6$, $Z^4*W^6$, $Z^5*W^6$, $Z^6*W^6$, and the like. Examples in the present specification show that $Z*W^5$ can be used as a preferred prediction formula, which combines the ratio of CD25$^+$Foxp3$^+$CD4$^+$ T-cells in CD4$^+$ T-cells (W) and the ratio of ICOS$^+$CD62L$^{low}$CD4$^+$ T-cells in CD62L$^{low}$CD4$^+$ T-cells (Z) by logistic regression or the like (FIGS. 25 and 26). Meanwhile, those skilled in the art can appropriately derive a different combination or different formula for indicators disclosed herein by a similar analysis.

The present specification further provides an indicator that can be used to distinguish a response group (complete response+partial response) and stable group (intermediate group) among a subject population determined as not part of an ineffective group.

The ratio of Foxp3$^+$CD25$^+$ T-cells in CD4$^+$ T-cells can be used as an indicator for predicting a response to cancer immunotherapy of a subject who has been predicted as not a part of an ineffective group. The inventors have discovered that a high ratio of Foxp3$^+$CD25$^+$ T-cells in CD4$^+$ T-cells in subjects shown as not a part of an ineffective group means that the subject is highly likely to be a part of a response group with respect to cancer immunotherapy. CD4$^+$Foxp3$^+$CD25$^+$ T-cells are regulatory T-cells with an immunosuppressive property, so that it was unexpected to find that a subject with a high ratio of such cells is highly likely to respond to cancer immunotherapy.

A ratio of LAG-3$^+$CD62L$^{low}$CD4$^+$ T cell subpopulation in CD62L$^{low}$CD4$^+$ T-cells, or a ratio of PD-1$^+$CD62L$^{low}$CD4$^+$ T cell subpopulation in CD62L$^{low}$CD4$^+$ T-cells can be used as an indicator for predicting a response to cancer immunotherapy of a subject who has been predicted as not a part of an ineffective group. The inventors have discovered that these cell subpopulations can be used to distinguish a response group (complete response+partial response) and stable group (intermediate group).

The method of the present invention can usebe used, for example, a comparison of a relative value of X to Y with a threshold value (ineffective group threshold value) comprising measuring the amount of CD80$^+$ dendritic cells (X) and measuring the amount of a CD28$^+$CD62L$^{low}$CD8$^+$ T-cell (Y) as an indicator for predicting that the subject is not a part of an ineffective group with respect to the cancer immunotherapy.

It is possible to predict that a subject is not a part of an ineffective group with any biomarker disclosed herein combined with any ineffective group threshold value. In addition, it is possible to predict an ineffective group using a threshold value determined for such indicators as an ineffective group threshold value, and use a threshold value for the ratio of Foxp3$^+$CD25$^+$ T-cells in CD4$^+$ T-cells for predicting that a subject population (preferably a subject population with an ineffective group excluded) is a part of a response group with respect to cancer immunotherapy as a response group threshold value.

Alternatively, a method of identifying a response group (PR) and a stable group (SD) in a subject population determined as not a part of an ineffective group is provided. A method of identifying a response group (PR) and a stable group (SD) can predict whether a subject is a part of a response group (PR) or a stable group (SD) by calculating variables (Z, W), with an amount of an ICOS$^+$CD62L$^{low}$CD4$^+$ T-cell subpopulation as (Z) and a value selected from the group consisting of:
an amount of a CD4$^+$CD25$^+$ T-cell subpopulation;
an amount of a CD4$^+$Foxp3$^+$ T-cell subpopulation;
an amount of a CD4$^+$Foxp3$^+$CD25$^+$ T-cell subpopulation;
an amount of a CD62L$^{high}$CD25$^+$CD4$^+$ T-cell subpopulation;
an amount of a CD45RA$^-$Foxp3$^+$CD4$^+$ T-cell subpopulation;
an amount of a CCR4$^+$CD25$^+$CD4$^+$ T-cell subpopulation;
an amount of a CD127$^+$CD25$^+$CD4$^+$ T-cell subpopulation; as (W).

A response group threshold value for the ratio of Foxp3$^+$CD25$^+$ T-cells in CD4$^+$ T-cells can be appropriately determined by those skilled in the art based on a reference, or a result shown in FIG. 12 can be appropriately selected as a response group threshold value. It should be noted that the ratio may be denoted hereinafter as percent (%).

When 2.05 is used as a response group threshold value for the ratio of Foxp3$^+$CD25$^+$ T-cells in CD4$^+$ T-cells, the ratio of Foxp3$^+$CD25$^+$ T-cells in CD4$^+$ T-cells can be used as a biomarker for predicting whether a subject is a part of a response group with sensitivity of 52.6% and specificity of 100%.

When a value of 2.05 or less (e.g., 2.05, 1.895, 1.76, 1.7, 1.61, or the like) is used as a response group threshold value for the ratio of Foxp3$^+$CD25$^+$ T-cells in CD4$^+$ T-cells, this can be used for predicting a response group as a biomarker with specificity of 100%.

When a value of 3.35 or greater (e.g., 3.35, 3.63, 4.365, or the like) is used as a response group threshold value for the ratio of Foxp3$^+$CD25$^+$ T-cells in CD4$^+$ T-cells, this can be used for predicting a response group as a biomarker with sensitivity of 100%.

In other words, a response group threshold value for the ratio of Foxp3$^+$CD25$^+$ T-cells in CD4$^+$ T-cells can be in the range of about 1.6 to about 4.4 (%). Examples of a response group threshold value for the ratio of Foxp3$^+$CD25$^+$ T-cells in CD4$^+$ T-cells include about 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, and 4.4 (%).

Another aspect of the present invention provides a method of applying cancer immunotherapy to a subject selected with any of the biomarkers disclosed above (preferably a combination of biomarkers). One embodiment provides a method of administering an immune checkpoint inhibitor to a subject in which any one of the above biomarkers is in a state indicated by any one of the threshold values disclosed herein.

(Fractionation/Separation of Cells)

A sample for fractionation/separation of T-cells can be suitably collected from a subject using a conventional method. For example, this can be collected from peripheral blood, bone marrow, tumor tissue, hematopoietic tissue, spleen, normal tissue, lymph, or the like of a subject. Sample collection from peripheral blood can be advantageous for being simple and non-invasive.

The composition of T-cells in a sample of a subject can be measured by those skilled in the art using a conventional method. Generally, the number of cells that are positive for a marker (e.g., CD4) defining a cell subpopulation of interest in a sample can be measured using flow cytometry or the like. Some embodiments of the present invention comprise measuring the amount of CD62L$^{low}$ T-cells in CD4$^+$ T-cells (X) and/or the amount of FoxP3$^+$CD25$^+$ T-cells in CD4$^+$ T-cells (Y). The measurement of the composition of a cell population generally uses flow cytometry, but may use a method using an antibody array or immunostaining on a sample comprising cells, protein expression analysis in a sample comprising cells (e.g., western blot, mass spectrometry, HPLC, or the like), mRNA expression analysis in a sample comprising cells (microarray or next generation sequencing), or the like.

To measure the cell count in each cell subpopulation such as CD62L$^{low}$CD4$^+$ T-cell subpopulation and CD4$^+$CD25$^+$ CD4$^+$Foxp3$^+$CD25$^+$ T-cell subpopulation, the measurement may be found by experimentally removing cells other than subpopulations of each kind from all cells. There is a kit for the materialization thereof. For example, cells corresponding to a CD4$^+$CD62L$^{low}$ T-cell subpopulation can be separated from peripheral blood without using a CD4 antibody or CD62L antibody when a CD4$^+$ Effector Memory T cell isolation kit, human (Militenyi Biotech) is used. This is achieved by counting and recording the total live cell count, and counting and recording the number of cells obtained using this kit. When a CD4$^+$CD25$^+$ Regulatory T-cell isolation kit, human (Militenyi Biotech) is used, the cell count corresponding to a CD4$^+$CD25$^+$CD4$^+$Foxp3$^+$CD25$^+$ T-cell subpopulation can be found without using an anti-FoxP3 antibody. Since FoxP3 is localized in the nucleus in cells, this has an advantage of eliminating a step for staining a molecule in the nucleus. As a similar kit, CD4$^+$CD25$^+$CD127$^{dim/-}$Regulatory T cell isolation kit, human (Militenyi Biotech) or CD25$^+$CD49d Regulatory T cell isolation kit, human (Militenyi Biotech) can also be selected.

An antibody does not need to be used. Antibodies that can specifically recognize and bind a molecule expressed on individual cells are prepared so that they can emit color when bound to a molecule expressed on the cell surface or inside the cells. The antibodies are then detected to measure the number of cells that are emitting color. Since the molecules expressed on the cell surface or inside the cells are proteins, mRNA encoding a protein when the protein is expressed is also formed in the cells. In other words, it is sufficient to examine mRNA in individual cells to examine the presence/absence of mRNA encoding a protein of interest. This is made possible by a single cell gene expression analysis, i.e., mRNA analysis at a single cell level. Examples of single cell gene expression analysis include 1) a method of next generation sequencing using Quartz-Seq, 2) a method of isolating cells using a Fluidigm C1 System or ICELL8 Single-Cell System to isolate cells and prepare a library with SMART-Seq v4, 3) a method of separating cells with a cell sorter and measuring the cells with quantitative PCR using an Ambion Single Cell-to-CT kit, 4) CyTOF SYSTEM (Helios), and the like.

In other words, blood is obtained, live cells are counted, and cells are separated with a cell sorter or the like. For example, Ambion Single Cell-to-CT kit can be used on the individual separated cells to measure the expression level of a specific gene with an apparatus for quantitative PCR. Based on the result, individual cells are examined as to which subpopulation among CD62L$^{low}$CD4$^+$ T-cell subpopulation and CD4$^+$Foxp3$^+$CD25$^+$ T-cell subpopulation the cells fall under, and the number of cells falling under each subpopulation is counted. The ratio of the numbers (ratio of x to y) is then found. Examples of candidate genes whose expression is examined include αβTCR, CD3, CD4, CD25, CTLA4, GITR, FoxP3, STAT5, FoxO1, FoxO3, IL-10, TGFbeta, IL-35, SMAD2, SMAD3, SMAD4, CD62Llow, CD44, IL-7R (CD127), IL-15R, CCR7low, BLIMP1, and the like.

As shown in the Example of the present specification, the genes whose expressions are increased in CD62L$^{low}$CD4$^+$ T-cells compared to CD62L$^{high}$CD4$^+$ T-cells include: AURAKA, CCL17, CD101, CD24, FOXF1, GZMA, GZMH, IL18RAP, IL21, IL5RA, ND2, SMAD5, SMAD7, and VEGFA (FIG. 34a). An amount and/or ratio of a cell subpopulation can be determined by measuring the expression of these genes, thereby determining which T cell subpopulation the obtained T cells belong to.

As shown in the Example of the present specification, the genes whose expressions are increased in CD62L$^{high}$CD4$^+$ T-cells compared to CD62L$^{low}$CD4$^+$ T-cells include: BACH2, CCL28, CCR7, CD27, CD28, CD62L, CSNK1D, FOXP1, FOXP3, IGF1R, IL16, IL27RA, IL6R, LEF1, MAL, and TCF7 (FIG. 34a). An amount and/or ratio of a cell subpopulation can be determined by measuring expression of these genes, thereby determining which T cell subpopulation the obtained T cells belong to.

Measurement of the ratio of cell subpopulations or comparison with a threshold value in the present invention may use a reference sample with a defined signal. Signals between a reference prepared to induce a fluorescent signal corresponding to a given cell subpopulation (e.g., particle to which a fluorescent pigment is attached) and a sample comprising a cell population can be compared to measure the amount and ratio of a cell population in the sample by comparison with a reference. Signals between a reference prepared to induce a fluorescent signal corresponding to a predetermined threshold value (e.g., particle to which a fluorescent pigment is attached) and a sample comprising a cell population can also be compared to determine the presence/absence or the marker of the present invention in the T-cell composition in the sample by a comparison with a reference.

When a specific marker is determined to be high (high expression) or low (low expression) in the present invention, those skilled in the art can use a classification baseline for expression intensity that is commonly used in the art. For example, it is possible to divide CD62L into CD62L$^{low}$ and CD62L$^{high}$ using the signal intensity corresponding to a 10E2 signal when using a PE-labeled anti-human CD62L antibody as the boundary.

In one embodiment, CD62L can be determined as high (high expression) or low (low expression) as follows. An antibody which is used as a negative control of the same isotype of an anti-CD62L antibody is prepared. The antibody used as a negative control should not recognize (bind) any antigen on a T-cell, but may non-specifically adsorb thereto. For example, an antibody sold as an isotype control is used. The same fluorescent label is used for an anti-CD62L antibody and the negative control. After preparation, respective fluorescence patterns are overlaid. In a typical pattern, the isotype control has a peak at a portion with a low level of fluorescence while the anti-CD62L antibody has a peak where the fluorescence level is high, and the fluorescence level slowly decreases where the fluorescence is lower (FIG. 28). In FIG. 28, the purple line is the staining pattern of the negative control and the area under the line which is colored with light blue is the staining pattern of the anti-CD62L antibody. The two patterns are compared. While some areas have the same fluorescence level as the negative control, it is determined that the entire peak of the negative control has shifted to the right (=where it is stained). Generally, it is determined thereby that almost all cells were stained by an antibody.

The determination of a boundary of low and high on the x axis (FL4-H) is now discussed. The right side of the figure is a schematic diagram when assuming that the peaks of low and high are divided. The peak of high appears to be horizontally symmetric, but low has a composite peak that cannot be considered horizontally symmetric. The peak of high is located at where FL4-H is, at about 400. The maximum amount of FL4-H of the peak of high (=A) is about 2,000. If the peak of high is considered horizontally symmetric, the inherent minimum amount of high (=B), which is separated by the same distance from FL4-H with the peak to A and is on the opposite side of the peak from A, is about 90. Up to this area, there should be an overlap with the peak of low. While the peak of high horizontally symmetric, horizontal symmetry is lost near D. In other words, D can be inferred to be the inherent maximum value of the peak of low, which means that there is a peak of low up to near D. Ultimately, high and low can be divided at the center of D, which is the maximum value of low, and B, which is the minimum value of high, i.e., C. This value corresponds to 10E2. In other words, the range of high can be C to A, and the range of low can be E to C. The area formed by the peak and each range corresponds to the cell count. The position of C on BD should vary depending on the ratio of sizes of peaks of high and low, sharpness of peaks or the like, but the difference from cases where the position of C is at the center of BD is considered small.

FIG. 29 shows a histogram for CD62L according to FACS analysis. It is understood that CD62L$^{low}$ can be separated very clearly with 10E2 as the boundary.

As used herein, "flow cytometry" refers to a technique of measuring the number of cells, individual or other biological particles suspended in a liquid and individual physical/chemical/biological attributes.

Various cells are analyzed using a flow cytometry technique. In particular, differentiation of blood cells can be determined using a flow cytometry technique. Such a determination of differentiation is starting to be used in diagnosis in addition to research.

Examples of advantages of flow cytometry include: the ratio accounted for blast cells can be readily found; specificity and sensitivity are high; it is highly reproducible; a large number of cells can be analyzed; the time required is short; and the like.

An apparatus using this technique is referred to as a "flow cytometer". A flow cytometer is an equipment for measuring optical characteristics of a suspended matter (cell) from a homogeneous suspension of cells. Cells pass through the focal point of a laser beam on a liquid flow. When passing, optical characteristics of forward scatter, side scatter, and one or more fluorescent light with different wavelengths can be simultaneously measured for individual cells at 500 to 4000 cells per second to quickly and accurately measure biological characteristics such as the cell size, internal structure, the amount of nucleic acid or various antigens that are present in the cell membrane, cytoplasm, or the nucleus.

Scattered light is light scattered to the surrounding after a laser hits a cell. Forward scatter (FSC) is detected in front with respect to the laser optical axis. The scatter light intensity is proportional to the surface area of a cell. In other words, it is understood that a cell is large if the FSC value is relatively large, and the cell is small if the FSC value is small. Side scatter (SSC) is detected at a position that is 90° (perpendicular) to the laser optical axis. The scatter light intensity is proportional to the state of intracellular structure or cell granule. In other words, it is understood that the internal structure of a cell is complex if the SSC value is relatively large, and the internal structure of a cell is simple if the SSC value is small.

Results of flow cytometry can be typically expressed as a dot plot, with FSC as the X axis and SSC as the Y axis. Each cell is represented by a single dot (point) in the graph. The position thereof is determined by the relative values of FSC and SSC. Lymphocytes with a relatively small size and simple internal structure are displayed in the bottom left section, granulocytes with a large size and a granule inside are displayed in the top right section, and mononuclear cells with a large size but a simple internal structure are displayed between the lymphocytes and the granulocytes, as populations separated from one another.

Fluorescent light refers to a light generated when a fluorescent pigment labeling a cell is excited by an irradiated laser beam and releases energy. A flow cytometer (e.g., product name: Becton & Dickinson FACSCalibur) typically irradiates a 488 nm single wavelength laser beam and a 635 nm single wavelength laser beam. A cell itself also has a property of emitting weak fluorescence (autofluorescence). However, when actually attempting to specifically detect a molecule of a cell using fluorescence, it is necessary to bind a fluorescent pigment to a cell or its molecule in some form in advance. For example, FITC (Fluorescein isothiocyanate) absorbs a 488 nm excitation light and mainly emits a 530 nm fluorescent light (green). Labeling of an antibody with FITC in advance leads to a difference in the amount of antibodies bound in accordance with the amount of antigens on the cell surface, resulting in a difference in the fluorescence intensity of FITC. Thus, the amount of antigens that are present on the cell surface can be estimated. FACSCalibur that can be used as an example has four fluorescence detectors installed, which can detect different fluorescence wavelength regions. If multiple fluorescent pigments that emit light with different wavelengths are prepared, up to four different antigens can be simultaneously detected. As a fluorescent pigment other than FITC which is excited by a 488 nm single wavelength laser beam, PE (phycoerythrin) mainly emits a 585 nm fluorescent light, and PerCP (peridinin chlorophyll protein) and PE-Cy5 (carbocyanin-5) mainly emit a 670 nm fluorescent light. APC (allophycocyanin), which is a fluorescent pigment excited by a 635 nm single wavelength laser beam, mainly emits a 670 nm fluorescent light. These fluorescent pigments are combined with various antibodies and used in double or triple staining of cells. CD4, CD8, CD62L, CD25, Foxp3 molecules, and the like that are expressed on the surface of T lymphocytes can be detected with a monoclonal antibody, which specifically react thereto.

Strictly speaking, there are two types of flow cytometers, i.e., equipment which only analyzes cells and equipment capable of sorting analyzed cells. The latter is called "FACS". As used herein, "FACS" is an abbreviation of fluorescence-activated cell sorter and refers to an apparatus used in a method of analyzing a surface antigen of a free cell such as a lymphocyte using a laser beam or sorting a specific cell by the presence/absence of a surface antigen or the like.

A result of flow cytometry can be displayed in a histogram, dot plot, or the like.

As used herein, "histogram" refers to a graph representing intensity of an optical signal of each parameter on the X axis and the cell count on the Y axis in fluorescence measurement using a flow cytometer. 10 thousand or more cells can be counted in total in such a form.

As used herein, "dot plot" refers to a plot of fluorescence intensity of two types of fluorescent pigments on the X and Y axes. In the double- or triple-stained analysis, this can be analyzed using a display method in which the respective fluorescence intensity is placed on the X or Y axis and individual cells correspond to each point on a two dimensional graph.

For example, peripheral blood or bone marrow liquid is collected, and then erythrocytes are removed by hemolytic method or specific gravity centrifugation, then the residual is reacted with a fluorescently labeled antibody (antibody to antigen of interest and a control antibody thereof) and sufficiently washed for observation using flow cytometry. The detected scattered light or fluorescence is converted to an electric signal and analyzed by a computer. The result can distinguish lymphocytes, mononuclear cells, and granulocytes by representing the intensity of FSC as the cell size and the intensity of SSC as intracellular structure. The cell population of interest is gated thereafter as needed to examine the antigen expressing manner in the cells.

In practicing the method of the present invention, those skilled in the art can suitably identify a surface marker of the shown cells to fractionate or count the cells.

CD antigens were agreed upon in an international workshop to be classified (clustering) as clusters mainly by the biochemical feature (especially molecular weight) of an antigen recognized thereby. This is called CD classification. Many types of monoclonal antibodies that recognize a specific leukocyte differentiation antigen are named thereby under a unified convention, which is CD followed by a number, i.e., CD number (i.e., CD1, CD2, and the like).

Typical examples of cell surface markers including CD markers that are used herein are explained hereinafter.

CD4 (6.2): binds to an MHC class II molecule on an antigen presenting cell and functions as a co-receptor of a T lymphocyte antigen receptor complex. CD4 is expressed in MHC class II restricted helper T lymphocyte.

CD8 (6.4): is a dimeric protein with an S—S bond of α and β chains. CD8 binds to an MHC class I molecule on an antigen presenting cell and functions as a co-receptor of a T lymphocyte antigen receptor complex. CD8 is expressed on MHC class I restricted killer T lymphocytes.

CD25: CD25 is a 55 kDa glycoprotein which is also known as a low affinity interleukin-2 receptor α chain (IL-2Rα). CD25 is also expressed in activated T-cells, B cells, and macrophages, and some non-activated $CD4^+$ T-cells, which act as regulatory T-cells. Thus, CD25 is utilized as a marker for regulatory T-cells.

CD62L: CD62L (L-selectin) is a molecule, which is required for recognizing and homing a high endothelial venule (HEV) that is present specifically in lymphoid organs. Naive T-cells have this molecule to prepare for circulation through the lymphoid organs and antigen presentation. Naive T-cells lose a homing molecule upon recognizing an antigen presented by dendritic cells in lymphoid organs is recognized with a T-cell receptor and being primed by effector T-cells. Thus, effector T-cells that have been primed by antigen recognition and cloned and expanded have the $CD62L^{low}$ phenotype.

Foxp3: Foxp3 is a master transcription factor of regulatory T-cells (Treg), i.e., transcription factor playing an essential role in all of differentiation/function expression/maintenance of differentiated status of Tregs. Since expression is nearly specific to Treg, Foxp3 is commonly used as a marker molecule for identifying Tregs. Foxp3 increases CD25 or CTLA4 expression, while suppressing the production of effector cytokines (IL-2, IFNγ, IL-4, IL-17, and the like).

PD-1 is deeply involved with the phenomenon of T cell exhaustion. In short, this phenomenon is attenuation of a T-cell reaction to antigens that are present in large quantity and for an extended period of time. Even if naive T-cells become T-cells with a high level of effector function due to priming by antigen presenting cells, the T-cells, upon exposure to large quantity antigen presentation for an extend period of time, express immune checkpoint molecules PD-1→LAG-3→CD244, lose the function and ultimately result in apoptosis. Since cancer cells are present "in large quantity" and "for an extended period of time", it can be understood that this system is in effect.

(Effect of Preventing/Treating Cancer by $CD62L^{low}CD4^+$ T-Cell Infusion)

Another aspect of the present invention is a method of improving or maintaining/sustaining a therapy effect of cancer immunotherapy by infusion of a specific cell or a composition therefor.

$CD62L^{low}CD4^+$ T-cells have been found to be critical in a response of a subject to cancer immunotherapy. It is understood that the use of such T-cells can improve or maintain responsiveness to cancer immunotherapy of a subject. One embodiment of the present invention is a composition comprising a $CD62L^{low}CD4^+$ T-cell. A $CD62L^{low}CD4^+$ T-cell or a composition comprising the same is useful for concomitant use with cancer immunotherapy.

Although not wishing to be bound by any theory, a therapeutic effect due to $CD62L^{low}CD4^+$ T-cell infusion into a patient on whom a PD-1 inhibitor and/or PD-L1 inhibitor does not achieve a sufficient effect of preventing/treating cancer can be understood as follows.

When PD-L1 expressed on the cancer cell surface binds to PD-1 expressed on the T-cell surface, an anti-tumor effect due to T-cells is suppressed (immune evasion mechanism by cancer cells). Anti-PD-1 antibodies are antibody molecules, which inhibit such a bond between PD-L1 and PD-1 and block the immune evasion mechanism by cancer cells to allow exertion of an anti-tumor effect by T-cells. Thus, it is understood that an anti-tumor effect due to inhibition of a PD-1/PD-L1 bond is primarily exerted in the effector phase where T-cells attack tumor, while the effect in the T-cell priming phase is low. In other words, it is difficult for a PD-1 or PD-L1 inhibitor to exert an anti-tumor effect unless there are already T-cell priming and sufficient effector T-cells. The maximum anti-tumor effect is exerted by anti-PD-1 antibodies on about 20% to 30% of cancer patients, but a T-cell immunity status required for an anti-PD-1 antibody to exert an anti-tumor effect and a method of evaluating such an immunity status were unknown.

CD62L (L-selectin) is a "homing receptor" of lymphocytes. CD62L is expressed on the cell surface of naive T-cells and promotes the migration thereof into the lymph node. When naive T-cells in the lymph node is subjected to antigen stimulation by an antigen presenting cell, the cells are activated into effector T-cells, while the CD62L expression level decreases ($CD62L^{low}$), and differentiate into $CD4^+$ T-cells (helper T-cells) or $CD8^+$ T-cells (cytotoxic T-cells). The inventors have discovered that $CD62L^{low}$ T-cells are very effective as a method of identifying T-cells primed by cancer antigens under circumstances where cancer antigens are unknown and cancer antigen specific T-cells cannot be identified. In a mouse model, $CD62L^{low}$ T-cells separated from a tumor regional lymph node can be adoptively infused to heal a cancer bearing mouse. Use of effector T-cells separated in this manner achieved a greater anti-tumor effect by introducing $CD62L^{low}CD4^+$ T-cells (Example 4 and FIG. 14). Most cancer cells including the tumor system used in this experiment do not express MHC class II antigens. Thus, it is understood that the high anti-tumor effect of $CD62L^{low}CD4^+$ T-cells is attained not by influencing a direct cytocidal function, but instead a function of antigen presenting cells such as dendritic cells to orchestrate the entire T-cell immunity. An excellent anti-tumor effect was also achieved when $CD62L^{low}CD8^+$ T-cells were used together with $CD62L^{low}CD4^+$ T-cells (Example 4 and FIG. 14).

The inventors have discovered that the ratio of $CD62L^{low}CD4^+$ T-cells in all T-cells is clearly correlated with an anti-tumor effect of anti-PD-1 antibodies, i.e., it is essential to comprise $CD62L^{low}CD4^+$ T-cells, which are T-cells exerting an anti-tumor effect, in order to exert an anti-tumor effect with anti-PD-1 antibodies.

Although not wishing to be bound by any theory, it is understood from this finding that T-cell immunity, which is ordinarily sufficient to exert an anti-tumor effect, is prepared, but immunity is evaded due to attenuation of antigen recognition signals by PD-1/PD-L1 in cancer patients comprising many $CD62L^{low}CD4^+$ T-cells. $CD62L^{low}CD4^+$ T-cells activate antigen presenting cells such as dendritic cells to activate a priming phase. Further, primed $CD8^+$ T-cells need to be subjected to antigen presentation from local antigen presenting cells that have been activated by effector $CD4^+$ T-cells in order to acquire a cytotoxic function. In this regard, it is understood that a PD-1/PD-L1 binding inhibitor, which restores attenuation of an antigen recognition signal primarily in the effector phase is complementary to the function of effector $CD4^+$ T-cells. It is understood that the antigen presenting cell function, which should present cancer antigens, is still suppressed even if the immune evasion mechanism is blocked with an anti-PD-1 antibody in patients who do not comprise a large quantity of $CD62L^{low}CD4^+$ T-cells, resulting in an unsatisfactory anti-tumor effect.

In view of the above, it is understood that administration of $CD62L^{low}CD4^+$ T-cells can exert an anti-tumor effect with an anti-PD-1 antibody on patients with low $CD62L^{low}CD4^+$ T-cell count resulting in an anti-tumor effect is not being exerted with an antiPD-1 antibody.

(Manufacture and Use of Cell Containing Composition)

A method of manufacturing a composition comprising a $CD62L^{low}CD4^+$ T-cell can comprising purifying $CD62L^{low}CD4^+$ T-cells from a T-cell population derived from a human. The purifying may comprise removing a CD62L high expression cell from a T-cell population (negative selection) Purification of $CD62L^{low}CD4^+$ T-cells by negative selection using an antibody and/or magnetic beads, or the like is preferable because impurities such as an antibody or magnetic beads do not remain on a cell to be used.

One embodiment of the present invention is a kit comprising a substance, which specifically binds to CD62L, for purifying $CD62L^{low}CD4^+$ T-cells. Examples of substances which specifically bind to CD62L include, but are not limited to, antibodies that are specific to CD62L. Those skilled in the art can isolate and expand a specific T-cell subpopulation disclosed herein in accordance with a method disclosed herein, e.g., flow cytometry. In one embodiment, the composition disclosed herein provides a $CD4^+CD62L^{low}$ T-cell.

T lymphocytes can be collected in accordance with a known technique and concentrated or drained by a known technique such as flow cytometry and/or affinity binding to an antibody such as immunomagnetic selection. After the concentration and/or draining step, in vitro expansion of desired T lymphocytes can be performed in accordance with a known technique (including, but not limited to, the technique disclosed in U.S. Pat. No. 6,040,177 by Riddell et al.) or a variation thereof that will be apparent to those skilled in the art.

For example, a desired T-cell population or subpopulation may be expanded by adding a first T lymphocyte population to a medium in vitro, then adding a feeder cell to the medium (e.g., so that the produced cell population contains at least about 5, 10, 20, 40 or more feeder cells for every T lymphocyte in the first population to be expanded), and incubating the culture (e.g., for a sufficient time to increase the number of T-cells). The culture can be typically incubated under conditions, such as temperature, that are suitable for the expansion of T lymphocytes. For growth of human T lymphocytes, the temperature is generally, for example, at least about 25° C., preferably at least about 30° C., and more preferably about 37° C.

Cells can be separated and/or expanded, and then stored as needed and administered to a subject thereafter in accordance with the method disclosed herein or a method that is well known in the art.

The amount of cells of interested (e.g., $CD62L^{low}CD4^+$ T-cell) in the composition comprising cell of the present invention, can be appropriately determined by the skilled in the art such that the intended effect is exerted, for example, may be at least $2\times10^8$, preferably at least $6\times10^8$, more preferably at least $2\times10^9$, for human administration.

A composition comprising cells disclosed herein can comprise a pharmaceutically acceptable carrier or excipient in addition to a cell of interest (e.g., $CD62L^{low}CD4^+$ T-cell). As used herein, "pharmaceutically acceptable" means approved by a government supervisory authority or listed in the Pharmacopoeia or other commonly recognized pharmacopoeia for use in animals, or more specifically humans. As used herein, "carrier" refers to a culture, infusion solution, perfusate, diluent, adjuvant, excipient, or vehicle, which is administered with a therapeutic agent. The composition comprising cells of the present invention comprises cells as the main ingredient, so that a carrier can preferably maintain cells such as culture, infusion solution or perfusate. For example, when a pharmaceutical composition is intravenously administered, saline and aqueous dextrose are preferred carriers. Preferably, an aqueous saline solution and aqueous dextrose and glycerol solution are used as a liquid carrier of an injectable solution. When a medicament is orally administered, water is a preferred carrier. Examples of suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, middle chain fatty acid triglyceride, polyoxyethylene hydrogenated castor oil 60, refined sugar, carboxymethylcellulose, cornstarch, inorganic salt, and the like. When desired, a composition can also contain a small amount of humectant or emulsifier, or a pH buffering agent. These compositions can be in a form of a solution, suspension, emulsion, tablet, pill, capsule, powder, sustained release formulation or the like. A composition can also be formulated as a suppository by using a traditional binding agent and a carrier such as a triglyceride. An oral formulation can also comprise a standard carrier such as a medical grade mannitol, lactose, starch, magnesium stearate, saccharine sodium, cellulose or magnesium carbonate. Examples of suitable carriers are disclosed in E. W. Martin, Remington's Pharmaceutical Sciences (Mark Publishing Company, Easton, U.S.A). Such a composition contains a therapeutically effective amount of a therapeutic agent, preferably in a refined form, together with a suitable amount of carrier to be provided in a form that is suitable for administration to a patient. A formulation must be suitable to the manner of administration. A formulation may additionally comprise, for example, a surfactant, excipient, coloring agent, flavoring agent, preservative, stabilizer, buffering agent, solubilizing agent, isotonizing agent, binding agent, disintegrant, lubricant, flow promoter, corrigent or the like.

Preferred Embodiments

One embodiment of the present invention is a method of using an amount selected from:

an amount of a $CD4^+$ T-cell subpopulation correlated with a dendritic cell stimulation in an anti-tumor immune response;

an amount of a dendritic cell subpopulation correlated with a dendritic cell stimulation by a $CD4^+$ T-cell in an anti-tumor immune response;

an amount of a $CD8^+$ T-cell subpopulation correlated with a dendritic cell stimulation in an anti-tumor immune response;

an amount of regulatory T-cells or a $CD4^+$ T-cell subpopulation correlated with regulatory T-cells; and an amount of an $ICOS^+CD62L^{low}CD4^+$ T-cell subpopulation;

in a subject as a variable (indicator) of a formula for predicting a response to cancer immunotherapy of the subject. In one embodiment, a variable (indicator) of a formula for predicting a response to cancer immunotherapy of a subject is selected from the group consisting of:

an amount of a $CD62L^{low}CD4^+$ T-cell subpopulation;

an amount of a $CCR7^-CD4^+$ T-cell subpopulation;

an amount of a $CD45RA^-CD4^+$ T-cell subpopulation;

an amount of a $CD45RO^+CD4^+$ T-cell subpopulation;

an amount of a $LAG-3^+CD62L^{low}CD4^+$ T-cell subpopulation;

an amount of an $ICOS^+CD62L^{low}CD4^+$ T-cell subpopulation;

an amount of a $CCR4^+CD25^+CD4^+$ T-cell subpopulation;

an amount of a $CD62L^{high}CD25^+CD4^+$ T-cell subpopulation;

an amount of a $CD127^+CD25^+CD4^+$ T-cell subpopulation; an amount of a $CD45RA\ Foxp3^+CD4^+$ T-cell subpopulation;

an amount of a $CD4^+CD25^+$ T-cell subpopulation;

an amount of a $CD4^+Foxp3^+$ T-cell subpopulation;

an amount of a $Foxp3^+CD25^+CD4^+$ T-cell subpopulation;

an amount of an $HLA-DR^+$ dendritic cell subpopulation;

an amount of a $CD80^+$ dendritic cell subpopulation;

an amount of a $CD86^+$ dendritic cell subpopulation;

an amount of a $PD-L1^+$ dendritic cell subpopulation;

an amount of a $CD62L^{low}CD8^+$ T-cell subpopulation;

an amount of a $CD137^+CD8^+$ T-cell subpopulation; and an amount of a $CD28^+CD62L^{low}CD8^+$ T-cell subpopulation.

One embodiment of the present invention is a method of using a relative amount selected from:

a relative amount of a $CD4^+$ T-cell subpopulation correlated with a dendritic cell stimulation in an anti-tumor immune response;

a relative amount of a dendritic cell subpopulation correlated with a dendritic cell stimulation by a $CD4^+$ T-cell in an anti-tumor immune response;

a relative amount of a CD8$^+$ T-cell subpopulation correlated with a dendritic cell stimulation in an anti-tumor immune response;

a relative amount of regulatory T-cells or a CD4$^+$ T-cell subpopulation correlated with regulatory T-cells; and a relative amount of an ICOS$^+$CD62L$^{low}$CD4$^+$ T-cell subpopulation;

in a subject as a variable (indicator) of a formula for predicting a response to cancer immunotherapy of the subject. In one embodiment, the relative amount, as a variable (indicator) of a formula for predicting a response to cancer immunotherapy of a subject, is selected from the group consisting of:

a ratio of a CD62L$^{low}$CD4$^+$ T-cell subpopulation in CD4$^+$ T-cells;

a ratio of a CCR7$^-$CD4$^+$ T-cell subpopulation in CD4$^+$ T-cells;

a ratio of a CD45RA$^-$CD4$^+$ T-cell subpopulation in CD4$^+$ T-cells;

a ratio of a CD45RO$^+$CD4$^+$ T-cell subpopulation in CD4$^+$ T-cells;

a ratio of a LAG-3$^+$CD62L$^{low}$CD4$^+$ T-cell subpopulation in CD62L$^{low}$CD4$^+$ T-cells;

a ratio of an ICOS$^+$CD62L$^{low}$CD4$^+$ T-cell subpopulation in CD62L$^{low}$CD4$^+$ T-cells;

a ratio of a CCR4$^+$CD25$^+$CD4$^+$ T-cell subpopulation in CD4$^+$ T-cells;

a ratio of a CD62L$^{high}$CD25$^+$CD4$^+$ T-cell subpopulation in CD4$^+$ T-cells;

a ratio of a CD127$^+$CD25$^+$CD4$^+$ T-cell subpopulation in CD4$^+$ T-cells;

a ratio of a CD45RA$^-$Foxp3$^+$CD4$^+$ T-cell subpopulation in CD4$^+$ T-cells;

a ratio of a CD4$^+$CD25$^+$ T-cell subpopulation in CD4$^+$ T-cells;

a ratio of a CD4$^+$Foxp3$^+$ T-cell subpopulation in CD4$^+$ T-cells;

a ratio of a Foxp3$^+$CD25$^+$CD4$^+$ T-cell subpopulation in CD4$^+$ T-cells;

a ratio of an HLA-DR$^+$ dendritic cell subpopulation in dendritic cells;

a ratio of a CD80$^+$ dendritic cell subpopulation in dendritic cells;

a ratio of a CD86$^+$ dendritic cell subpopulation in dendritic cells;

a ratio of a PD-L1$^+$ dendritic cell subpopulation in dendritic cells;

a ratio of a CD62L$^{low}$CD8$^+$ T-cell subpopulation in CD8$^+$ T-cells;

a ratio of a CD137$^+$CD8$^+$ T-cell subpopulation in CD8$^+$ T-cells; and an ratio of a CD28$^+$CD62L$^{low}$CD8$^+$ T-cell subpopulation in CD62L$^{low}$CD8$^+$ T-cells.

One embodiment of the present invention is a method of using an amount selected from:

an amount of a CD4$^+$ T-cell subpopulation correlated with a dendritic cell stimulation in an anti-tumor immune response;

an amount of a dendritic cell subpopulation correlated with a dendritic cell stimulation by a CD4$^+$ T-cell in an anti-tumor immune response;

an amount of a CD8$^+$ T-cell subpopulation correlated with a dendritic cell stimulation in an anti-tumor immune response; and an amount of regulatory T-cells or a CD4$^+$ T-cell subpopulation correlated with regulatory T-cells;

in a subject as a variable (indicator) of a formula for predicting a response to cancer immunotherapy of the subject, wherein an indicator formula higher than a threshold value (ineffective group threshold value) indicates that the subject is not a part of an ineffective group to the cancer immunotherapy. In one embodiment, a variable (indicator) of a formula for predicting a response to cancer immunotherapy of a subject is selected from the group consisting of:

an amount of a CD62L$^{low}$CD4$^+$ T-cell subpopulation;

an amount of a LAG-3$^+$CD62L$^{low}$CD4$^+$ T-cell subpopulation;

an amount of a CCR7$^-$CD4$^+$ T-cell subpopulation;

an amount of a CD45RA$^-$CD4$^+$ T-cell subpopulation;

an amount of a CD45RO$^+$CD4$^+$ T-cell subpopulation;

an amount of an HLA-DR$^+$ dendritic cell subpopulation;

an amount of a CD80$^+$ dendritic cell subpopulation;

an amount of a CD86$^+$ dendritic cell subpopulation;

an amount of a PD-L1$^+$ dendritic cell subpopulation;

an amount of a CD62L$^{low}$CD8$^+$ T-cell subpopulation;

an amount of a CD137$^+$CD8$^+$ T-cell subpopulation;

an amount of a CD28$^+$CD62L$^{low}$CD8$^+$ T-cell subpopulation;

an amount of a CD4$^+$Foxp3$^+$CD25$^+$ T-cell subpopulation;

an amount of a CD62L$^{high}$CD25$^+$CD4$^+$ T-cell subpopulation;

an amount of a CD45RA$^-$Foxp3$^+$CD4$^+$ T-cell subpopulation;

an amount of a CCR4$^+$CD25$^+$CD4$^+$ T-cell subpopulation; and an amount of a CD127$^+$CD25$^+$CD4$^+$ T-cell subpopulation;

wherein an indicator formula higher than a threshold value (ineffective group threshold value) indicates that the subject is not a part of an ineffective group to the cancer immunotherapy.

One embodiment of the present invention is a method of using a relative amount selected from:

a relative amount of a CD4$^+$ T-cell subpopulation correlated with a dendritic cell stimulation in an anti-tumor immune response;

a relative amount of a dendritic cell subpopulation correlated with a dendritic cell stimulation by a CD4$^+$ T-cell in an anti-tumor immune response;

a relative amount of a CD8$^+$ T-cell subpopulation correlated with a dendritic cell stimulation in an anti-tumor immune response; and a relative amount of regulatory T-cells or a CD4$^+$ T-cell subpopulation correlated with regulatory T-cells;

in a subject as a variable (indicator) of a formula for predicting a response to cancer immunotherapy of the subject, wherein an indicator formula higher than a threshold value (ineffective group threshold value) indicates that the subject is not a part of an ineffective group to the cancer immunotherapy. In one embodiment, the relative amount, as a variable (indicator) of a formula for predicting a response to cancer immunotherapy of a subject is selected from the group consisting of:

a ratio of a CD62L$^{low}$CD4$^+$ T-cell subpopulation in CD4$^+$ T-cells;

a ratio of a LAG-3$^+$CD62L$^{low}$CD4$^+$ T-cell subpopulation in CD62L$^{low}$CD4$^+$ T-cells;

a ratio of a CCR7$^-$CD4$^+$ T-cell subpopulation in CD4$^+$ T-cells;

a ratio of a CD45RA$^-$CD4$^+$ T-cell subpopulation in CD4$^+$ T-cells;

a ratio of a CD45RO$^+$CD4$^+$ T-cell subpopulation in CD4$^+$ T-cells;

a ratio of an HLA-DR⁺ dendritic cell subpopulation in dendritic cells;
a ratio of a CD80⁺ dendritic cell subpopulation in dendritic cells;
a ratio of a CD86⁺ dendritic cell subpopulation in dendritic cells;
a ratio of a PD-L1⁺ dendritic cell subpopulation in dendritic cells;
a ratio of a CD62L$^{low}$CD8⁺ T-cell subpopulation in CD8⁺ T-cells;
a ratio of a CD137⁺CD8⁺ T-cell subpopulation in CD8⁺ T-cells;
an ratio of a CD28⁺CD62L$^{low}$CD8⁺ T-cell subpopulation in CD62L$^{low}$CD8⁺ T-cells;
a ratio of a CD4⁺Foxp3⁺CD25⁺ T-cell subpopulation in CD4⁺ T-cells;
a ratio of a CD62L$^{high}$CD25⁺CD4⁺ T-cell subpopulation in CD4⁺ T-cells;
a ratio of a CD45RA⁻Foxp3⁺CD4⁺ T-cell subpopulation in CD4⁺ T-cells;
a ratio of a CCR4⁺CD25⁺CD4⁺ T-cell subpopulation in CD4⁺ T-cells; and
a ratio of a CD127⁺CD25⁺CD4⁺ T-cell subpopulation in CD4⁺ T-cells;
wherein an indicator formula higher than a threshold value (ineffective group threshold value) indicates that the subject is not a part of an ineffective group to the cancer immunotherapy.

One embodiment of the present invention is a method of predicting a response to cancer immunotherapy of a subject using amounts (X, Y) selected from:
an amount of a CD4⁺ T-cell subpopulation correlated with a dendritic cell stimulation in an anti-tumor immune response;
an amount of a dendritic cell subpopulation correlated with a dendritic cell stimulation by a CD4⁺ T-cell in an anti-tumor immune response;
an amount of a CD8⁺ T-cell subpopulation correlated with a dendritic cell stimulation in an anti-tumor immune response; and
an amount of regulatory T-cells or a CD4⁺ T-cell subpopulation correlated with regulatory T-cells;
as a variable (indicator) of formula F(X, Y), wherein formula F(X, Y) higher than a threshold value (ineffective group threshold value) indicates that the subject is not a part of an ineffective group to the cancer immunotherapy. In one embodiment, formula F(X, Y) can be calculated, with a variable (indicator) of a formula for predicting a response to cancer immunotherapy of a subject, which is a value selected from the group consisting of:
an amount of a CD62L$^{low}$CD4⁺ T-cell subpopulation;
an amount of a LAG-3⁺CD62L$^{low}$CD4⁺ T-cell subpopulation;
an amount of a CCR7⁻CD4⁺ T-cell subpopulation;
an amount of a CD45RA⁻CD4⁺ T-cell subpopulation;
an amount of a CD45RO⁺CD4⁺ T-cell subpopulation;
an amount of an HLA-DR⁺ dendritic cell subpopulation;
an amount of a CD80⁺ dendritic cell subpopulation;
an amount of a CD86⁺ dendritic cell subpopulation;
an amount of a PD-L1⁺ dendritic cell subpopulation;
an amount of a CD62L$^{low}$CD8⁺ T-cell subpopulation;
an amount of a CD137⁺CD8⁺ T-cell subpopulation; and
an amount of a CD28⁺CD62L$^{low}$CD8⁺ T-cell subpopulation
as (X). In one embodiment, F(X, Y) can be calculated, with a variable (indicator) of a formula for predicting a response to cancer immunotherapy of a subject, which is a value selected from the group consisting of:
an amount of a CD4⁺Foxp3⁺CD25⁺ T-cell subpopulation;
an amount of a CD62L$^{high}$CD25⁺CD4⁺ T-cell subpopulation;
an amount of a CD45RA⁻Foxp3⁺CD4⁺ T-cell subpopulation;
an amount of a CCR4⁺CD25⁺CD4⁺ T-cell subpopulation; and
an amount of a CD127⁺CD25⁺CD4⁺ T-cell subpopulation;
as (Y). Formula F(X, Y) higher than a threshold value (ineffective group threshold value) indicates that the subject is not a part of an ineffective group to the cancer immunotherapy.

One embodiment of the present invention is a method of predicting a response to cancer immunotherapy of a subject using amounts (X, Y) selected from:
a relative amount of a CD4⁺ T-cell subpopulation correlated with a dendritic cell stimulation in an anti-tumor immune response;
a relative amount of a dendritic cell subpopulation correlated with a dendritic cell stimulation by a CD4⁺ T-cell in an anti-tumor immune response;
a relative amount of a CD8⁺ T-cell subpopulation correlated with a dendritic cell stimulation in an anti-tumor immune response; and
a relative amount of regulatory T-cells or a CD4⁺ T-cell subpopulation correlated with regulatory T-cells;
in a subject as a variable (indicator) of formula F(X, Y), wherein formula F(X, Y) higher than a threshold value (ineffective group threshold value) indicates that the subject is not a part of an ineffective group to the cancer immunotherapy. In one embodiment, formula F(X, Y) can be calculated, with a variable (indicator) of a formula for predicting a response to cancer immunotherapy of a subject, which is a value selected from the group consisting of:
a ratio of a CD62L$^{low}$CD4⁺ T-cell subpopulation in CD4⁺ T-cells;
a ratio of a LAG-3⁺CD62L$^{low}$CD4⁺ T-cell subpopulation in CD62L$^{low}$CD4⁺ T-cells;
a ratio of a CCR7⁻CD4⁺ T-cell subpopulation in CD4⁺ T-cells;
a ratio of a CD45RA⁻CD4⁺ T-cell subpopulation in CD4⁺ T-cells;
a ratio of a CD45RO⁺CD4⁺ T-cell subpopulation in CD4⁺ T-cells;
a ratio of an HLA-DR⁺ dendritic cell subpopulation in dendritic cells;
a ratio of a CD80⁺ dendritic cell subpopulation in dendritic cells;
a ratio of a CD86⁺ dendritic cell subpopulation in dendritic cells;
a ratio of a PD-L1⁺ dendritic cell subpopulation in dendritic cells;
a ratio of a CD62L$^{low}$CD8⁺ T-cell subpopulation in CD8⁺ T-cells;
a ratio of a CD137⁺CD8⁺ T-cell subpopulation in CD8⁺ T-cells; and
an ratio of a CD28⁺CD62U° wCD8⁺ T-cell subpopulation in CD62L$^{low}$CD8⁺ T-cells as (X). In one embodiment, formula F(X, Y) can be calculated, with a variable (indicator) of a formula for predicting a response to cancer immunotherapy of a subject, which is a value selected from the group consisting of:
a ratio of a CD4⁺Foxp3⁺CD25⁺ T-cell subpopulation in CD4⁺ T-cells;

a ratio of a CD62L$^{high}$CD25$^+$CD4$^+$ T-cell subpopulation in CD4$^+$ T-cells;

a ratio of a CD45RA$^-$Foxp3$^+$CD4$^+$ T-cell subpopulation in CD4$^+$ T-cells;

a ratio of a CCR4$^+$CD25$^+$CD4$^+$ T-cell subpopulation in CD4$^+$ T-cells; and a ratio of a CD127$^+$CD25$^+$CD4$^+$ T-cell subpopulation in CD4$^+$ T-cells; as (Y). Formula F(X, Y) higher than a threshold value (ineffective group threshold value) indicates that the subject is not a part of an ineffective group to the cancer immunotherapy.

Another embodiment of the present invention is a method of predicting a response to cancer immunotherapy of a subject, wherein formula F(X, Y) higher than a threshold value (ineffective group threshold value) indicates that the subject is not a part of an ineffective group to the cancer immunotherapy. Formula F(X, Y) can be calculated, with a variable (indicator) of a formula for predicting a response to cancer immunotherapy of a subject, which is a value selected from the group consisting of:

an amount of a CD62L$^{low}$CD4$^+$ T-cell subpopulation;
an amount of a LAG-3$^+$CD62L$^{low}$CD4$^+$ T-cell subpopulation;
an amount of a CCR7$^-$CD4$^+$ T-cell subpopulation;
an amount of a CD45RA$^-$CD4$^+$ T-cell subpopulation;
an amount of a CD80$^+$ dendritic cell subpopulation;
an amount of a CD62L$^{low}$CD8$^+$ T-cell subpopulation;
an amount of a CD137$^+$CD8$^+$ T-cell subpopulation; and
an amount of a CD28$^+$CD62U$^\circ$ wCD8$^+$ T-cell subpopulation as (X), and a value selected form the group consisting of:
an amount of a CD4$^+$Foxp3$^+$CD25$^+$ T-cell subpopulation;
an amount of a CD62L$^{high}$CD25$^+$CD4$^+$ T-cell subpopulation; and
an amount of a CD45RA$^-$Foxp3$^+$CD4$^+$ T-cell subpopulation; as (Y).

Another embodiment of the present invention is a method of predicting a response to cancer immunotherapy of a subject, wherein formula F(X, Y) higher than a threshold value (ineffective group threshold value) indicates that the subject is not a part of an ineffective group to the cancer immunotherapy. Formula F(X, Y) can be calculated, with a variable (indicator) of a formula for predicting a response to cancer immunotherapy of a subject, which is a value selected from the group consisting of:

a ratio of a CD62L$^{low}$CD4$^+$ T-cell subpopulation in CD4$^+$ T-cells;

a ratio of a LAG-3$^+$CD62L$^{low}$CD4$^+$ T-cell subpopulation in CD62L$^{low}$CD4$^+$ T-cells;

a ratio of a CCR7$^-$CD4$^+$ T-cell subpopulation in CD4$^+$ T-cells;

a ratio of a CD45RA$^-$CD4$^+$ T-cell subpopulation in CD4$^+$ T-cells;

a ratio of a CD80$^+$ dendritic cell subpopulation in dendritic cells;

a ratio of a CD62L$^{low}$CD8$^+$ T-cell subpopulation in CD8$^+$ T-cells;

a ratio of a CD137$^+$CD8$^+$ T-cell subpopulation in CD8$^+$ T-cells; and an ratio of a CD28$^+$CD62L$^{low}$CD8$^+$ T-cell subpopulation in CD62L$^{low}$CD8$^+$ T-cells as (X), and a ratio of a CD4$^+$Foxp3$^+$CD25$^+$ T-cell subpopulation in CD4$^+$ T-cells;

a ratio of a CD62L$^{high}$CD25$^+$CD4$^+$ T-cell subpopulation in CD4$^+$ T-cells; and a ratio of a CD45RA$^-$Foxp3$^+$CD4$^+$ T-cell subpopulation in CD4$^+$ T-cells; as (Y).

Any function (F(X, Y)) of X and Y which monotonically increases with respect to X and monotonically decreases with respect to Y can be used as the aforementioned formula F(X, Y). Examples of formula F(X, Y) indicating responsiveness include $F=X^r*Y^s$, wherein r and s are any real numbers. When X is positively correlated with responsiveness and Y is negatively correlated with responsiveness, it is preferable that r is a positive number and s is a negative number. Integers can be used for r and s for simplicity of the formula. For instance, F(X, Y) can be represented as Xn*Ym, wherein n and m are any integers. Examination of the inventors has shown that responsiveness to cancer immunotherapy of a subject can be accurately predicted using a formula with r and s in the range of −3 to 3. Examples of preferred forms of the formula include, but are not limited to, X/Y, $X^2$/Y, X*Y, and the like.

One embodiment of the present invention is a method of using an amount selected from:

an amount of regulatory T-cells or a CD4$^+$ T-cell subpopulation correlated with regulatory T-cells;

an amount of an ICOS$^+$CD62L$^{low}$CD4$^+$ T-cell subpopulation;

an amount of an LAG-3$^+$CD62L$^{low}$CD4$^+$ T cell subpopulation; and an amount of an PD-1$^+$CD62L$^{low}$CD4$^+$ T cell subpopulation;

in a subject determined to be not a part of an ineffective group as a variable (indicator) of a formula for predicting a response to cancer immunotherapy of the subject, wherein an indicator formula higher than a threshold value (response group threshold value) indicates that the subject is a part of a response group to the cancer immunotherapy. In one embodiment, a variable (indicator) of a formula for predicting a response to cancer immunotherapy of a subject is selected from the group consisting of:

an amount of an ICOS$^+$CD62L$^{low}$CD4$^+$ T-cell subpopulation;

an amount of a CD4$^+$CD25$^+$ T-cell subpopulation;

an amount of a CD4$^+$Foxp3$^+$ T-cell subpopulation;

an amount of a CD4$^+$Foxp3$^+$CD25$^+$ T-cell subpopulation;

an amount of a CD62L$^{high}$CD25$^+$CD4$^+$ T-cell subpopulation;

an amount of a CD45RA$^-$Foxp3$^+$CD4$^+$ T-cell subpopulation;

an amount of a CCR4$^+$CD25$^+$CD4$^+$ T-cell subpopulation;

an amount of a CD127$^+$CD25$^+$CD4$^+$ T-cell subpopulation;

an amount of an LAG-3$^+$CD62L$^{low}$CD4$^+$ T cell subpopulation; and an amount of an PD-1$^+$CD62L$^{low}$CD4$^+$ T cell subpopulation.

One embodiment of the present invention is a method of using a relative amount selected from:

a relative amount of regulatory T-cells or a CD4$^+$ T-cell subpopulation correlated with regulatory T-cells;

a relative amount of an ICOS$^+$CD62L$^{low}$CD4$^+$ T-cell subpopulation;

a relative amount of an LAG-3$^+$CD62L$^{low}$CD4$^+$ T cell subpopulation; and a relative amount of an PD-1$^+$CD62L$^{low}$CD4$^+$ T cell subpopulation;

in a subject determined to be not a part of an ineffective group as a variable (indicator) of a formula for predicting a response to cancer immunotherapy of the subject, wherein an indicator formula higher than a threshold value (response group threshold value) indicates that the subject is a part of a response group to the cancer immunotherapy. In one embodiment, a variable (indicator) of a formula for predicting a response to cancer immunotherapy of a subject is selected from the group consisting of:

a ratio of an ICOS$^+$CD62L$^{low}$CD4$^+$ T-cell subpopulation in CD62L$^{low}$CD4$^+$ T-cells;

a ratio of a CD4$^+$CD25$^+$ T-cell subpopulation in CD4$^+$ T-cells;

a ratio of a CD4$^+$Foxp3$^+$ T-cell subpopulation in CD4$^+$ T-cells;

a ratio of a CD4$^+$Foxp3$^+$CD25$^+$ T-cell subpopulation in CD4$^+$ T-cells;

a ratio of a CD62L$^{high}$CD25$^+$CD4$^+$ T-cell subpopulation in CD4$^+$ T-cells;

a ratio of a CD45RA$^-$Foxp3$^+$CD4$^+$ T-cell subpopulation in CD4$^+$ T-cells;

a ratio of a CCR4$^+$CD25$^+$CD4$^+$ T-cell subpopulation in CD4$^+$ T-cells;

a ratio of a CD127$^+$CD25$^+$CD4$^+$ T-cell subpopulation in CD4$^+$ T-cells;

an ratio of an LAG-3$^+$CD62L$^{low}$CD4$^+$ T cell subpopulation in CD4$^+$ T-cells; and an ratio of an PD-1$^+$CD62L$^{low}$CD4$^+$ T cell subpopulation in CD4$^+$ T-cells.

One embodiment of the present invention is a method of using amounts (W, Z) selected from:

an amount of regulatory T-cells or a CD4$^+$ T-cell subpopulation correlated with regulatory T-cells; and an amount of an ICOS$^+$CD62L$^{low}$CD4$^+$ T-cell subpopulation; in a subject determined to be not a part of an ineffective group as variables (indicators) of formula J(W, Z) for predicting a response to cancer immunotherapy of the subject, wherein formula J(W, Z) higher than a threshold value (response group threshold value) indicates that the subject is a part of a response group to the cancer immunotherapy. In one embodiment, formula J(W, Z) can be calculated, with a variable (indicator) of a formula for predicting a response to cancer immunotherapy of a subject, which is an amount of an ICOS$^+$CD62L$^{low}$CD4$^+$ T-cell subpopulation as (Z) and a value selected from the group consisting of:

an amount of a CD4$^+$CD25$^+$ T-cell subpopulation;
an amount of a CD4$^+$Foxp3$^+$ T-cell subpopulation;
an amount of a CD4$^+$Foxp3$^+$CD25$^+$ T-cell subpopulation;
an amount of a CD62L$^{high}$CD25$^+$CD4$^+$ T-cell subpopulation;
an amount of a CD45RA$^-$Foxp3$^+$CD4$^+$ T-cell subpopulation;
an amount of a CCR4$^+$CD25$^+$CD4$^+$ T-cell subpopulation; and
an amount of a CD127$^+$CD25$^+$CD4$^+$ T-cell subpopulation; as (W). Formula J(W, Z) higher than a threshold value (response group threshold value) indicates that the subject is a part of a response group to the cancer immunotherapy.

One embodiment of the present invention is a method of using amounts (Z, W) selected from:

a relative amount of regulatory T-cells or a CD4$^+$ T-cell subpopulation correlated with regulatory T-cells; and a relative amount of an ICOS$^+$CD62L$^{low}$CD4$^+$ T-cell subpopulation;

in a subject determined to be not a part of an ineffective group, as variables (indicators) of formula J(W, Z) for predicting a response to cancer immunotherapy of the subject, wherein formula J(W, Z) higher than a threshold value (response group threshold value) indicates that the subject is a part of a response group to the cancer immunotherapy. In one embodiment, formula J(W, Z) can be calculated, with a variable (indicator) of a formula for predicting a response to cancer immunotherapy of a subject, which is a ratio of an ICOS$^+$CD62L$^{low}$CD4$^+$ T-cell subpopulation in CD62L$^{low}$CD4$^+$ T-cells as (Z) and a value selected from the group consisting of:

a ratio of CD4$^+$CD25$^+$ T-cell subpopulation in CD4$^+$ T-cells;

a ratio of a CD4$^+$Foxp3$^+$ T-cell subpopulation in CD4$^+$ T-cells;

a ratio of a CD4$^+$Foxp3$^+$CD25$^+$ T-cell subpopulation in CD4$^+$ T-cells;

a ratio of a CD62L$^{high}$CD25$^+$CD4$^+$ T-cell subpopulation in CD4$^+$ T-cells;

a ratio of a CD45RA$^-$Foxp3$^+$CD4$^+$ T-cell subpopulation in CD4$^+$ T-cells;

a ratio of a CCR4$^+$CD25$^+$CD4$^+$ T-cell subpopulation in CD4$^+$ T-cells; and a ratio of a CD127$^+$CD25$^+$CD4$^+$ T-cell subpopulation in CD4$^+$ T-cells; as (W). Formula J(W, Z) higher than a threshold value (response group threshold value) indicates that the subject is a part of a response group to the cancer immunotherapy.

Another embodiment of the present invention is a method of predicting a response to cancer immunotherapy of a subject who has been determined to be not a part of an ineffective group, wherein formula J(W, Z) higher than a threshold value (response group threshold value) indicates that the subject is a part of a response group to the cancer immunotherapy. Formula J(W, Z) can be calculated, with variables (indicators) of a formula for predicting a response to cancer immunotherapy of a subject, which are:

an amount of an ICOS$^+$CD62L$^{low}$CD4$^+$ T-cell subpopulation as (Z) and a value selected from the group consisting of:

an amount of a CD4$^+$CD25$^+$ T-cell subpopulation;
an amount of a CD4$^+$Foxp3$^+$ T-cell subpopulation;
an amount of a CD4$^+$Foxp3$^+$CD25$^+$ T-cell subpopulation;
an amount of a CD62L$^{high}$CD25$^+$CD4$^+$ T-cell subpopulation; and
an amount of a CD45RA$^-$Foxp3$^+$CD4$^+$ T-cell subpopulation; as (W).

Another embodiment of the present invention is a method of predicting a response to cancer immunotherapy of a subject who has been determined to be not a part of an ineffective group, wherein formula J(W, Z) higher than a threshold value (response group threshold value) indicates that the subject is a part of a response group to the cancer immunotherapy. Formula J(W, Z) can be calculated, with variables (indicators) of a formula for predicting a response to cancer immunotherapy of the subject, which are:

a ratio of an ICOS$^+$CD62L$^{low}$CD4$^+$ T-cell subpopulation in CD62L$^{low}$CD4$^+$ T-cells; as (Z) and a value selected from the group consisting of:

a ratio of a CD4$^+$CD25$^+$ T-cell subpopulation in CD4$^+$ T-cells;

a ratio of a CD4$^+$Foxp3$^+$ T-cell subpopulation in CD4$^+$ T-cells;

a ratio of a CD4$^+$Foxp3$^+$CD25$^+$ T-cell subpopulation in CD4$^+$ T-cells;

a ratio of a CD62L$^{high}$CD25$^+$CD4$^+$ T-cell subpopulation in CD4$^+$ T-cells; and a ratio of a CD45RA$^-$Foxp3$^+$CD4$^+$ T-cell subpopulation in CD4$^+$ T-cells; as (W).

Any function (J(Z, W)) of Z and W which monotonically increases with respect to Z and monotonically increases with respect to W can be used as the aforementioned formula J(Z, W). Examples of formula J(Z, W) indicating responsiveness include $J=Z^r*W^s$, wherein r and s are any real numbers. When Z is positively correlated with responsiveness and W is negatively correlated with responsiveness, it is preferable that r is a positive number and s is a negative number. Integers can be used for r and s for simplicity of the formula. For instance, J(Z, W) can be represented as $Z^n*W^m$, wherein n and m are any integers. Examination of the inventors have shown that responsiveness to cancer immunotherapy of a subject can be accurately predicted using a formula with r and s in the range of −5 to 6. Examples of preferred forms of the formula include, but are not limited to, $Z/W$, $Z^2/W$, $Z*W$, $Z*W^5$ and the like.

The method disclosed herein, including those disclosed above, can be used to apply cancer immunotherapy to a subject who has been indicated as not a part of an ineffective group with respect to the cancer immunotherapy and/or as a part of a responsive group. Any cancer immunotherapy disclosed herein can be used.

One embodiment provides a composition for treating cancer in a subject who has been indicated as not a part of an ineffective group with respect to the cancer immunotherapy and/or as a part of a responsive group by using the method disclosed herein, including those disclosed above. The composition can comprise any active ingredient disclosed herein and have any constitution disclosed herein.

(General Techniques)

Molecular biological approaches, biochemical approaches, and microbiological approaches used herein are well known and conventional approaches in the art that are disclosed in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press; Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997, and the like. The relevant portions (which can be the entire document) of the above documents are incorporated herein by reference.

As used herein, "or" is used when "at least one or more" of the listed matters in the sentence can be employed. When explicitly described herein as "within the range" of "two values", the range also includes the two values themselves.

Reference literatures such as scientific literatures, patents, and patent applications cited herein are incorporated herein by reference to the same extent that the entirety of each document is specifically described.

As disclosed above, the present invention has been disclosed while showing preferred embodiments to facilitate understanding. The present invention is disclosed hereinafter based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

The present invention is exemplified by the following Examples herein.

(1) [Example Demonstrating Enablement of the Invention of Markers]

Example 1: Therapeutic Effect of Anti-PD-1 Antibody and T-Cell Population Composition This Example demonstrates that analysis of $CD62L^{low}CD4^+$ T-cells and $Foxp3^+CD25^+CD4^+$ T-cells using peripheral blood can predict a therapeutic effect of therapy with an anti-PD-1 antibody.

(2) [Example Demonstrating Enablement of Invention of Cell Infusion]

Example 2: Hypothetical Example of Infusing $CD62L^{low}$ Cells

Example 3: Follow Up Observation

The Example demonstrates that an anti-tumor immune response of a patient is correlated with the T-cell composition, i.e., increase in $CD62L^{low}$ cells enhances the anti-tumor immune response in a patient undergoing anti-PD-1 therapy to reduce tumor.

Example 4: Cell Infusion into Mice

The Example demonstrates that the percentage of $CD62L^{low}CD4^+$ T-cell increases by infusing $CD62L^{low}CD4^+$ T-cells in mice. An increase in the percentage of $CD62L^{low}$ $CD4^+$ T-cell and Treg also enhances anti-tumor immune responses in mice.

Example 5: Isolation/Expansion of $CD62L^{low}$ Cells

The Example demonstrates that $CD62L^{low}$ cells can be successfully isolated and expanded.

(Example 1: Therapeutic effect of anti-PD-1 antibody and T-cell population composition)

1-1. Objective

The objective of this Example is to demonstrate that analysis of $CD62L^{low}CD4^+$ T-cells and $Foxp3^+CD25^+CD4^+$ T-cells using peripheral blood can predict a therapeutic effect of therapy with an anti-PD-1 antibody. The relationship between a therapeutic effect of an anti-PD-1 antibody and T-cell population composition was investigated.

1-2. Materials and Methods

Figure 2:
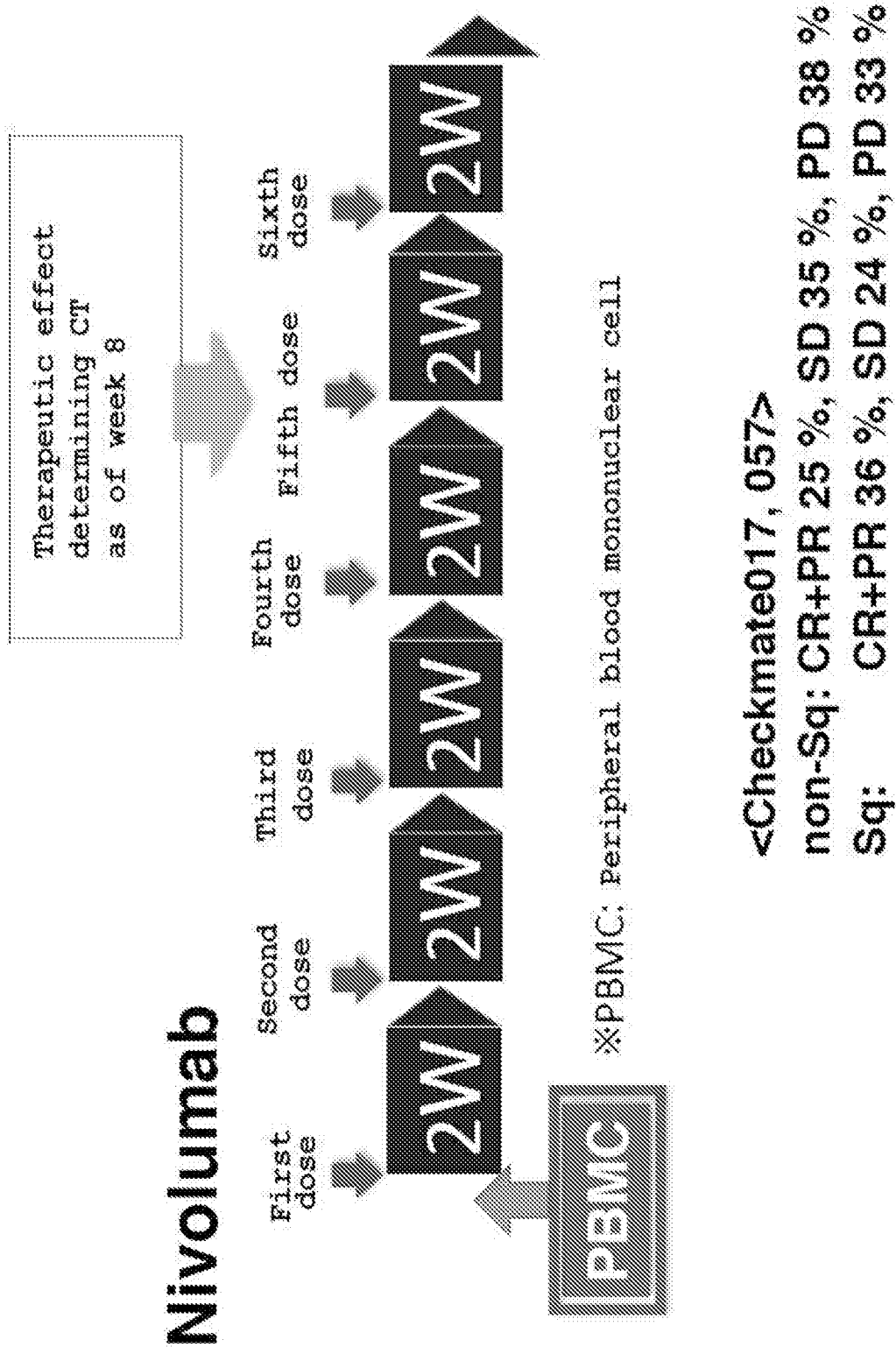
FIG. 2 is a schematic diagram showing the procedure of measuring a therapeutic effect in Example 1.

The effect of nivolumab therapy in non-small cell lung cancer patients was studied in accordance with the protocol shown in FIG. 2.

Peripheral blood was collected the day before nivolumab therapy from non-small cell lung cancer patients who have already undergone therapy.

CT was administered for determining the effect at week 8 from the start of nivolumab therapy. Partial response (PR), stable (SD), and progressive (PD) at this point were determined. The criteria of determination was in accordance with RECIST ver. 1.1. The following Table 1 shows the Characteristics of patients.

TABLE 1

Characteristic of patients (n = 44)

Age

| | |
|---|---|
| Median, value | 67 |
| Range | 51-84 |

Sex-number (%)

| | |
|---|---|
| Male | 30 (68) |
| Female | 14 (32) |

Histological diagnosis-number (%)

| | |
|---|---|
| Squamous | 12 (27) |
| Non-squamous | 32 (73) |

History of smoking-number (%)

| | |
|---|---|
| Current or previous smoker | 33 (75) |
| No history of smoking | 11 (25) |

Pathological phase-number (%)

| | |
|---|---|
| c-stage III | 9 (20) |
| c-stage IV | 26 (59) |
| Post-op recurrence | 9 (20) |

EGFR status-number (%)

| | |
|---|---|
| Wild-type | 37 (84) |
| Mutant (exon 19del or L858R) | 7 (16) |

The composition of a peripheral blood T-cell population of subjects was analyzed as follows.

(1) Blood Collection 8 ml of blood was collected in a blood collecting tube for mononuclear cell separation (product name: BD Vacutainer® CPT™, BD Japan), which was gently inverted and mixed at room temperature.

(2) Centrifugation (Separation of Mononuclear Cells by Specific Gravity Centrifugation)

After blood collection, BD Vacutainer® CPT™ was centrifuged at 1500 to 1800×g for 15 minutes (centrifuge name/manufacturer: Kubota).

(3) Collection

About half of the plasma layer was aspirated so as not to disturb the cell layer above a gel barrier. The cell layer above the gel barrier was collected with a Pasteur pipette and transferred into a 50 ml tube (Falcon tube or the like). A phosphate-buffered balanced salt solution (10% FBS PBS) supplemented with 10% fetal bovine serum was added so that the mixture was 30 ml or greater. The mixture was centrifuged (4° C., 400 to 450 g×5 minutes) and washed twice.

(4) Cell Count

After completion of the first washing/centrifugation, 10 ml of PBS supplemented with 10% FBS (inactivated at 56° C. in 30 minutes) was added to resuspend cells. 50 µl of cell suspension in a centrifuge tube was collected. 0.1% trypan blue solution (50 µl) and the cell suspension were stirred. The cells were placed in an Improved Neubauer hemocytometer to count the cells.

(5) Freezing

After completion of the second washing/centrifugation, CELLBANKER™2 (Takara Bio) was used. Cells were resuspended in $5\times10^5$ to $5\times10^6$/ml, and transferred into a 2.0 ml cryogenic vial (Corning). After treatment, the cells were promptly frozen in a −80° C. deep freezer (Panasonic). After 24 hours and within one week of the above treatment, the cells were transferred into liquid nitrogen (under liquid phase).

(6) Culture

The frozen cells were adjusted to be 1 to $5\times10^5$/ml in an RPMI 1640 medium (FBS 10%) and cultured for 24 to 36 hours in a T-25 cell culture flask at 37° C. with 5% $CO^2$.

(7) Cell Adjustment

Cell culture was collected in a 15 ml centrifuge tube and was centrifuged at 1500 rpm for 10 minutes to gather the cells at the bottom of the centrifuge tube. After the centrifugation, the supernatant was removed. 10 ml of FACS buffer was added to cell pellets to resuspend the cells with a pipette. The cells were against centrifuged at 1500 rpm for 10 minutes, and then the supernatant was aspirated. The cells were counted and adjusted so that the final cell concentration was $1.0\times10^6$ cells/ml. FACS buffer: 2% FBS, 0.05% Azide in PBS.

(8) Antibody Reaction

Suspension of peripheral blood mononuclear cells was placed in each FACS tube at 0.5 ml ($5\times10^5$ cells would be in each tube). The tube was centrifuged with a centrifuge at 1500 rpm for 5 minutes. The cell pellets were left while aspirating and removing only the supernatant.

Tube 1

20 µl of FITC labeled anti-human CD4 antibody (25 µg/ml)

20 µl of PE labeled anti-human CD62L antibody (5 µg/ml)

20 µl of PE-Cy5 labeled anti-human CD8 antibody (5 µg/ml)

An antibody solution and cell suspension were stirred and mixed. The tubes were maintained at 4° C. After 30 minutes, 1 ml of FACS buffer was added to each tube with a Komagome pipette, and the mixture was centrifuged with a centrifuge at 1500 rpm for 5 minutes. The supernatant was aspirated and removed. 0.5 ml of 1% paraformaldehyde was added to each tube, from which the supernatant was aspirated while leaving only the cell pellets, to suspend the cells.

Tube 2

20 µl of FITC labeled anti-human CD4 antibody (25 µg/ml)

20 µl of PE-Cy5 labeled anti-human CD25 antibody (5 µg/ml)

An antibody solution and cell suspension were stirred and mixed. The tubes were maintained at 4° C. After 30 minutes, 1 ml of FACS buffer was added to each tube, and the mixture was centrifuged with a centrifuge at 1500 rpm for 5 minutes. The supernatant was aspirated and removed. Intracellular Fixation and Permeabilization buffer set™ (eBioscience) was used for cytoplasmic staining with 3 µl of PE labeled anti-human FOXP3 antibodies (500 µg/ml). 0.5 ml of 1% paraformaldehyde was added to each tube, from which the supernatant was aspirated while leaving only the cell pellets, to suspend the cells.

(9) Analysis by Flow Cytometry (Product Name: FACS Calibur™; BD Japan)

Measurement of Samples

Fluorescence of tubes 1 and 2 are measured.

Incorporation of analysis data for 30,000 cells

Analysis

STEP 1 Tube 1 is analyzed to identify a lymphocyte region using two-dimensional analysis using FSC or SSC. Cells gated in the lymphocyte region are further gated with respect to CD4+ fraction to obtain a histogram plot of CD62L (cell count in the blue region)

STEP 2 Tube 2 is analyzed to obtain two-dimensional analysis data with Foxp3 and CD25, which are gated in the lymphocyte region and CD4+ region.

(Cell Count in the Orange Region)

STEP 3 Calculation of the ratio of $CD62L^{low}CD4^{+}$/$Foxp3^{+}CD25^{+}CD4^{+}$ Formula Cell count in STEP 1/cell count in STEP 2

Figure 1:
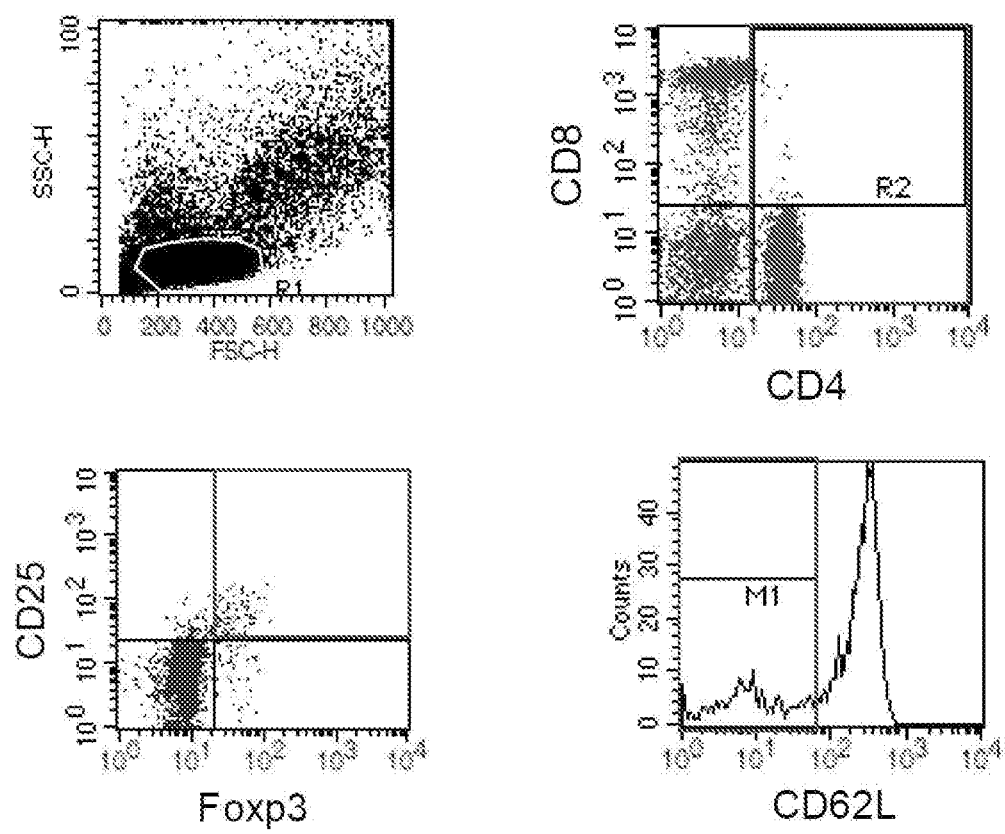
FIG. 1 is a diagram showing results of fractionation by flow cytometry of T-cells in a peripheral blood sample obtained from a subject. The top left diagram identifies a lymphocyte region by two-dimensional analysis using FSC and SSC. The top right diagram is a fraction with respect to CD8 and CD4 expression. The bottom left diagram is a fraction of $CD25^+FoxP3^+$. The bottom right diagram is a histogram with respect to CD62L expression levels. CD62L low expression ($CD62L^{low}$) cells are fractionated in a double peak distribution.

FIG. 1 shows an example of a result for cell fractions in flow cytometry. It should be noted that mRNA was measured with a microarray between $CD62L^{low}$ and $CD62L^{high}$. While the present Example fractionates cells using flow cytometry, other separation methods can also be used.

(Determination)

If lower than a predetermined value, Progressive Disease is predicted, for which drug is not effective.

If higher than a predetermined value, go to STEP 4

STEP 4

Formula Cell count in the orange region/cell count for R1 and R2 in STEP 1×100 (%)

(Determination)

If lower than a predetermined value, Stable Disease (SD) is predicted.

If higher than a predetermined value, Partial Response (PR) is predicted.

Statistical analysis was conducted on the relationship between the resulting T-cell population composition and observed therapeutic effect.

1-3. Results

The following Table 2 shows the observed therapeutic effect on patients.

TABLE 2

| Response to nivolumab Objective response in 8 weeks-number (%) | |
| --- | --- |
| Complete or partial response | 11 (25) |
| Stable | 19 (43) |
| Progressive | 14 (32) |

Confirmed complete and partial responses were evaluated in accordance with the Response Evaluation Criteria in Solid Tumors, version 1.1 by the testers.

The ratio of therapeutic effect observed in this Example is approximately the same as the response rate obtained in the phase III clinical trial called checkmate 017. Thus, it is understood that there is no bias in a response to nivolumab.

Figure 3:
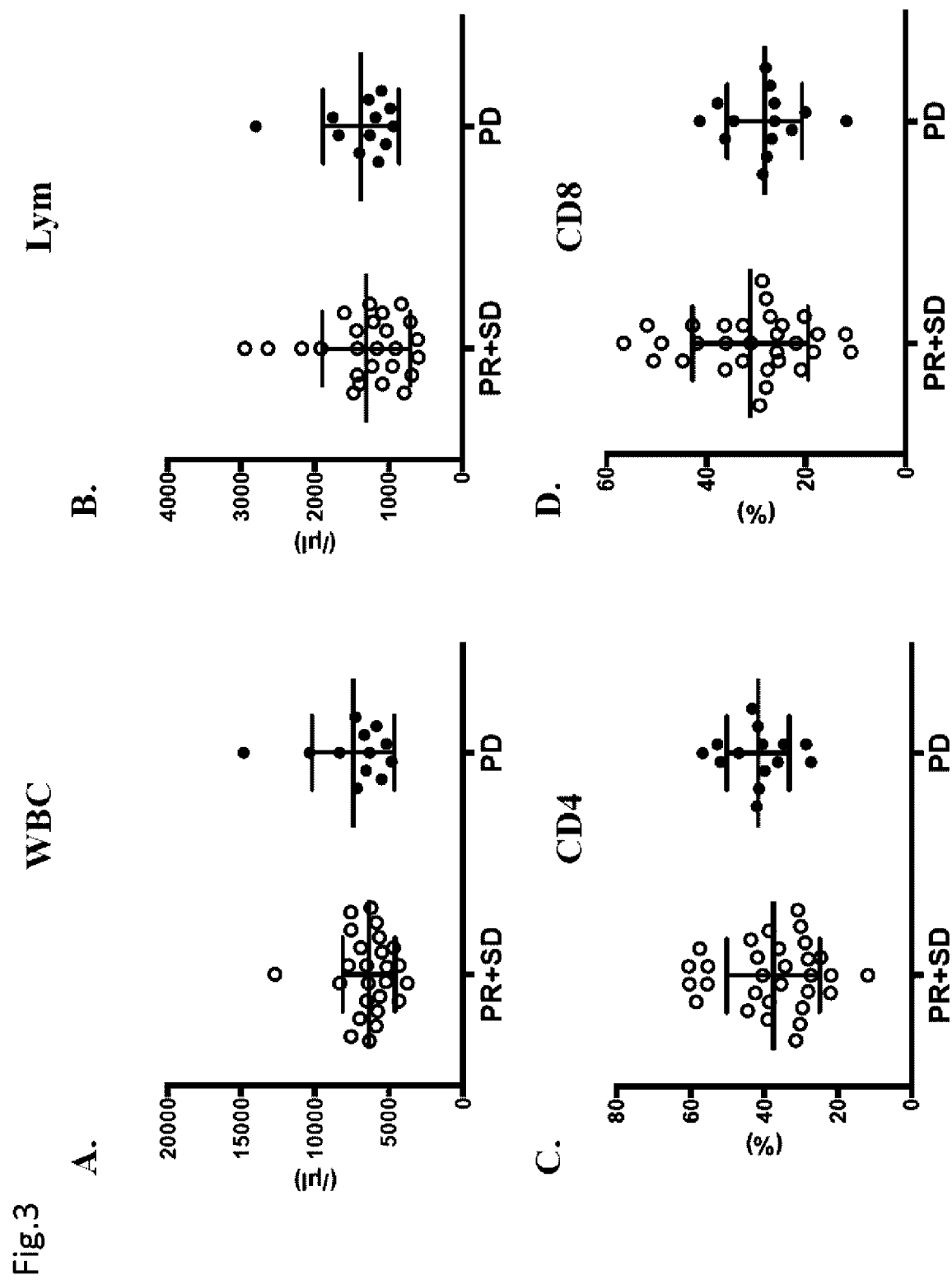
FIG. 3 is a diagram comparing the cell count and T-cell composition between an ineffective group and other groups. Panel A (WBC) compares the peripheral blood white blood cell (White Blood Cell) count. Panel B (Lym) compares the lymphocyte count. Panel C compares the percentage of CD4+ cells. Panel D compares the percentage of CD8+ cells. A significant difference was not found between the ineffective group and other groups with respect to these parameters.

As shown in FIG. 3, there is no significant difference in the peripheral blood white blood cell count, lymphocyte count, $CD4^{+}$ cell percentage, or CD8+ cell percentage between PR+SD groups and PD groups. The subject population in this Example did not comprise a complete response (CR) group. If a CR group were present, the CR group would be identified as a part of the PR group of the present invention.

The result shows that the percentage of $CD62^{low}$ cells in CD8 cells was significantly lower in PD groups (FIG. 4A). However, the percentage of PR+SD group and PD group overlaps over a wide range, where P=0.0138 in a significance test. In contrast, the percentage of $CD62^{low}$ cells in $CD4^{+}$ cells was completely different between the PR+SD group and the PD group with almost no overlap (FIG. 4B). Meanwhile, the result shows that the percentage of $CD25^{+}Foxp3+$ cells, which are regulatory T-cells in CD4+ cells was significantly higher in the PD group (FIG. 4C). It is the consensus in the art that the $CD25^{+}Foxp3^{+}CD4^{+}$ cell fraction can be considered a regulatory T-cell fraction.

Figure 4:
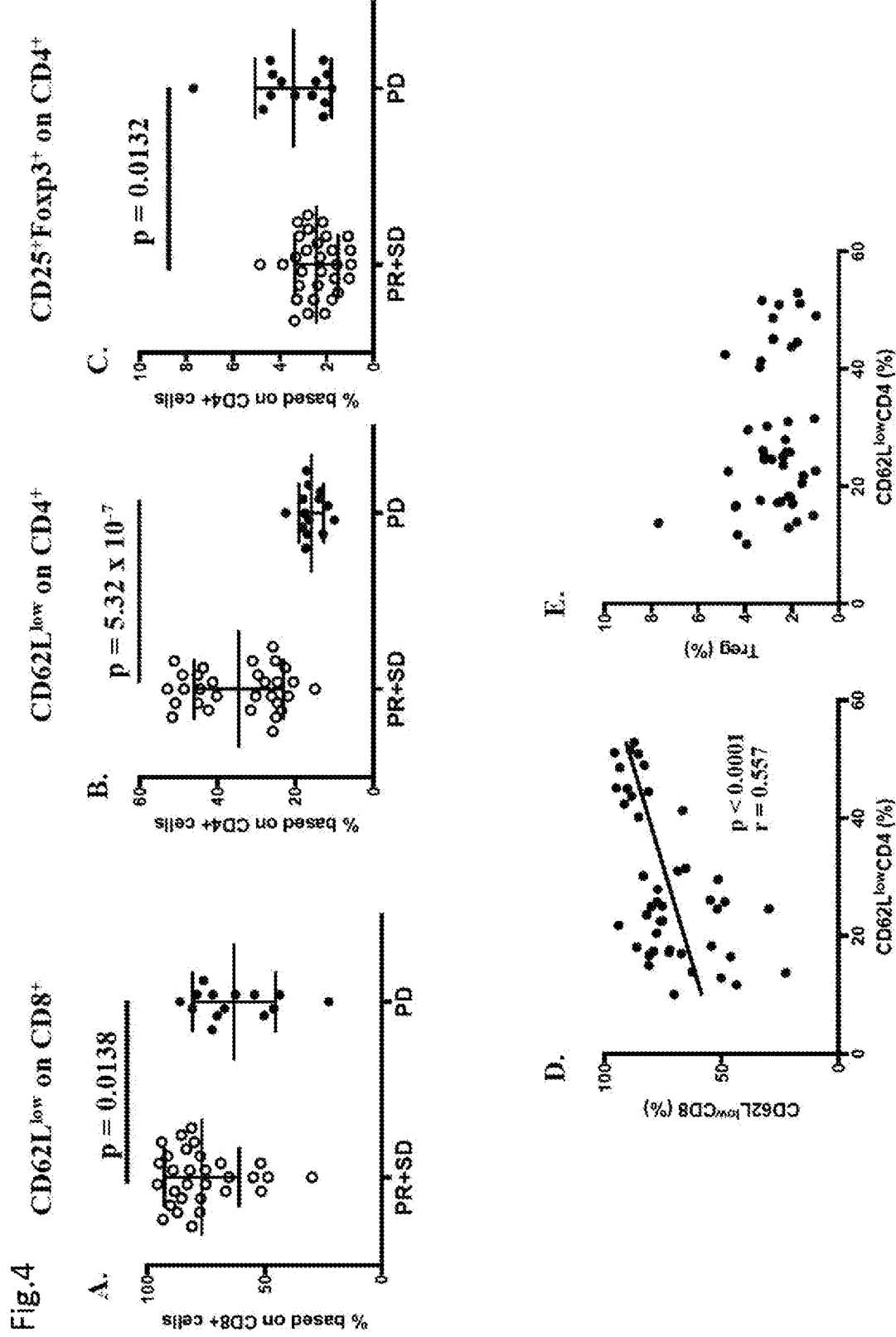
FIG. 4 is a diagram comparing the T-cell composition between an ineffective group and other group. Panel A compares the percentage of $CD62L^{low}$ cells in $CD8^+$ T-cells. This is significantly lower for a PD group. P=0.0138. Panel B compares the percentage of $CD62L^{low}$ cells in $CD4^+$ T-cells. A more significant decrease was observed in the PD group than the percentage of $CD62L^{low}$ cells in $CD8^+$ T-cells. $P=5.32\times10^{-7}$. Panel C compares the percentage of $CD25^+FoxP3^+$ cells in CD4+ T-cells. This was significantly higher in the PD group. P=0.0132. Panel D is a scatter diagram for the percentage of $CD62L^{low}$ cells in $CD8^+$ T-cells and the percentage of $CD62L^{low}$ cells in $CD4^+$ T-cells. A week correlation was found between these values. Panel E is a scatter diagram of the percentage of $CD62L^{low}$ cells in $CD4^+$ T-cells and the percentage of $CD25^+FoxP3^+$ cells in $CD4^+$ T-cells. A correlation was not found between these values. It is understood that they each independently contribute to responsiveness to cancer immunotherapy.

Furthermore, results of analyzing the correlation among three T-cell subpopulations with a difference between PD group and the PR+SD group are shown in panels D and E of FIG. 4. A strong correlation was found between the percentage of $CD62L^{low}CD8^{+}$ and the percentage of $CD62L^{low}CD4+$ (FIG. 4D). As biological significance, the $CD8^{+}$ effector count is suggested to be regulated by $CD4^{+}$ effectors. This shows that it is preferable to use only one of them as a biomarker. It is demonstrated that use of the percentage of $CD62L^{low}CD4^{+}$, which has a very small p value, as a biomarker for the effector side is very useful in the prediction of a therapeutic effect of an immune checkpoint inhibitor.

Furthermore, a correlation was not found between regulatory T-cells and the percentage of $CD62L^{low}CD4^{+}$. This indicates that the respective cell counts are regulated by different mechanisms. It is understood that the precision of predicting a therapeutic effect can be enhanced by using both in combination as a biomarker.

FIGS. 5 to 12 show the results of further examining a parameter which can be used as a biomarker.

Figure 5:
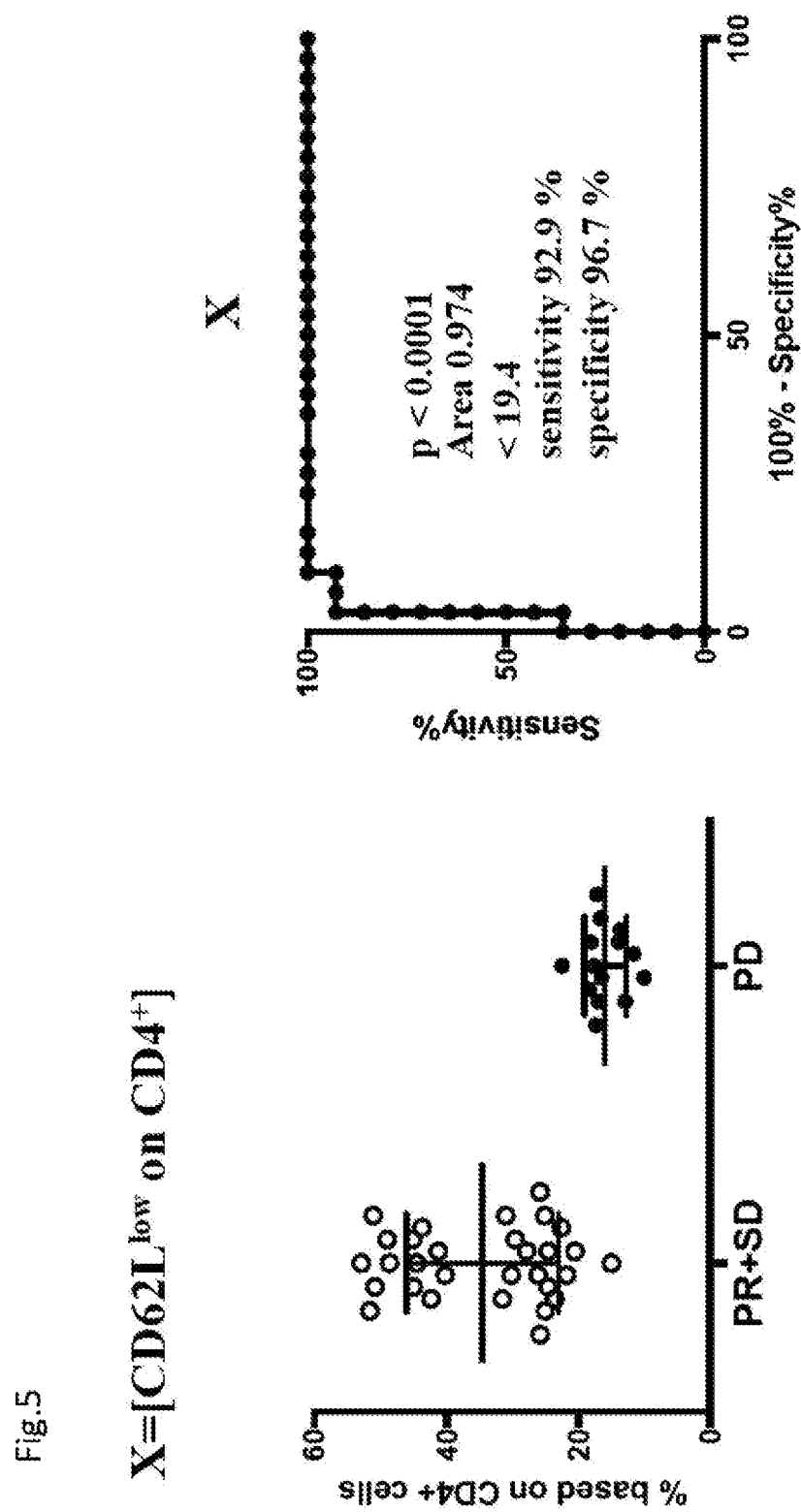
FIG. 5 shows the performance of the percentage of $CD62L^{low}$ cells in $CD4^+$ T-cells as an indicator for distinguishing a PR+SD group from a PD group. The right panel plots the sensitivity and specificity upon changes in a threshold value. The area of the region under the plotted points is 0.974. Thus, this is understood as a very good marker.

A very good result of 92.6% sensitivity and 96.7% specificity was obtained with 19.4% as the threshold value, even by using only the percentage of $CD62L^{low}CD4^{+}$ with a large difference (FIG. 5). The sensitivity and specificity for various threshold values are shown in FIG. 6.

Figure 7:
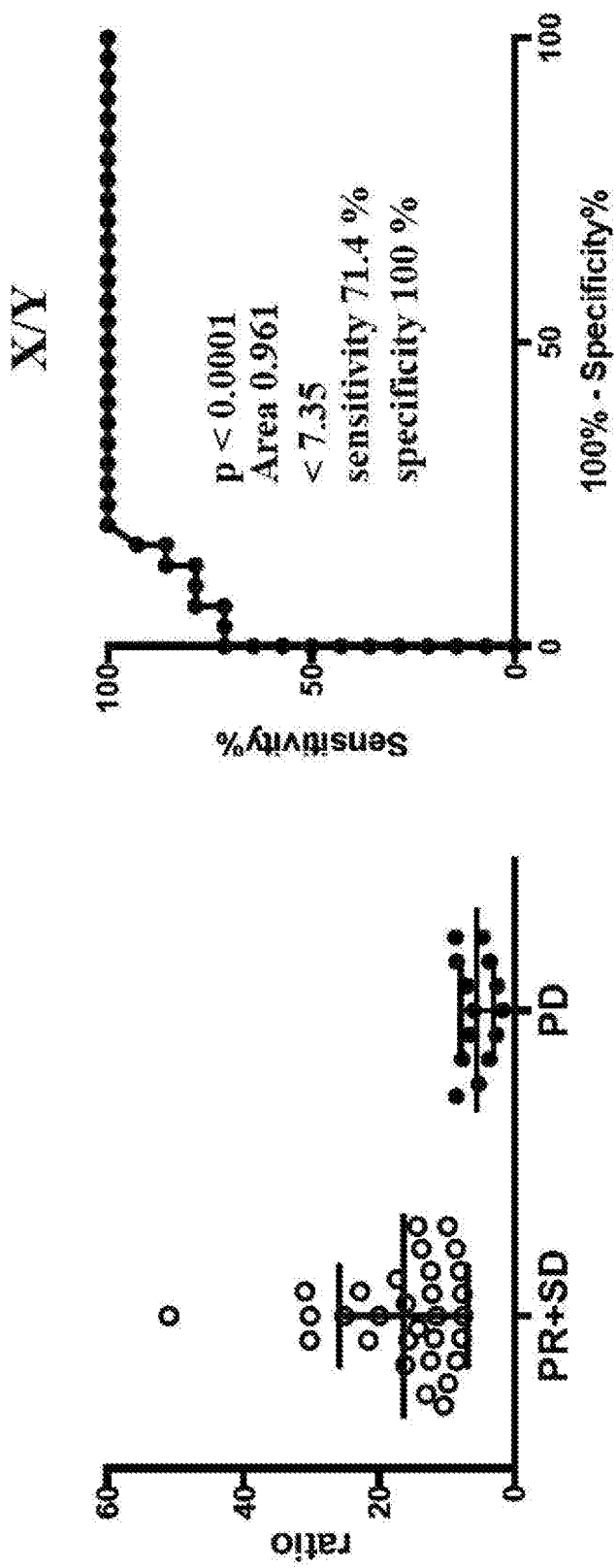
FIG. 7 shows the performance of the relative value (X/Y) of the percentage of $CD62L^{low}$ cells in $CD4^+$ T-cells (X) to the percentage of $CD25^+FoxP3^+$ cells in $CD4^+$ T-cells (Y) as an indicator for distinguishing a PR+SD group from a PD group. The right panel plots the sensitivity and specificity upon changing a threshold value. The area of the region under the plotted points is 0.961. Thus, this is understood as a very good marker.

The precision of prediction using a relative value of regulator T-cells and the percentage of $CD62L^{low}CD4+$ was examined. FIG. 7 shows the results of a ratio (X/Y) of two factors that move differently in a PD group as a numerator and a denominator when using the percentage of $CD62L^{low}CD4+$ as X and the percentage of CD25+Foxp3+CD4+ as Y. It is understood that use of this indicator can clearly distinguish a patient in which regulatory T-cells have significantly increased so that an anti-tumor effect is no longer observed. FIG. 8 shows sensitivity and specificity for various threshold values. It is understood that a marker with specificity of 100% and sensitivity of 71.4% is obtained when a threshold value is 7.35.

For a formula using a combination of these factors, a suitable formula was examined using logistic regression from results in a sample of N=40 while considering the weighting for these factors with respect to the effect on therapeutic effects. A logistic regression model was used to find a coefficient, resulting in deriving the formula of $X^{2.475}/Y$ (FIG. 27). It is understood that responsiveness can be accurately predicted by using a formula with a coefficient in the vicinity thereof ($X^{2-3}/Y$). For example, it is understood that formulas such as $X^{2}/Y$ and $X^{3}/Y$ can be used.

Figure 9:
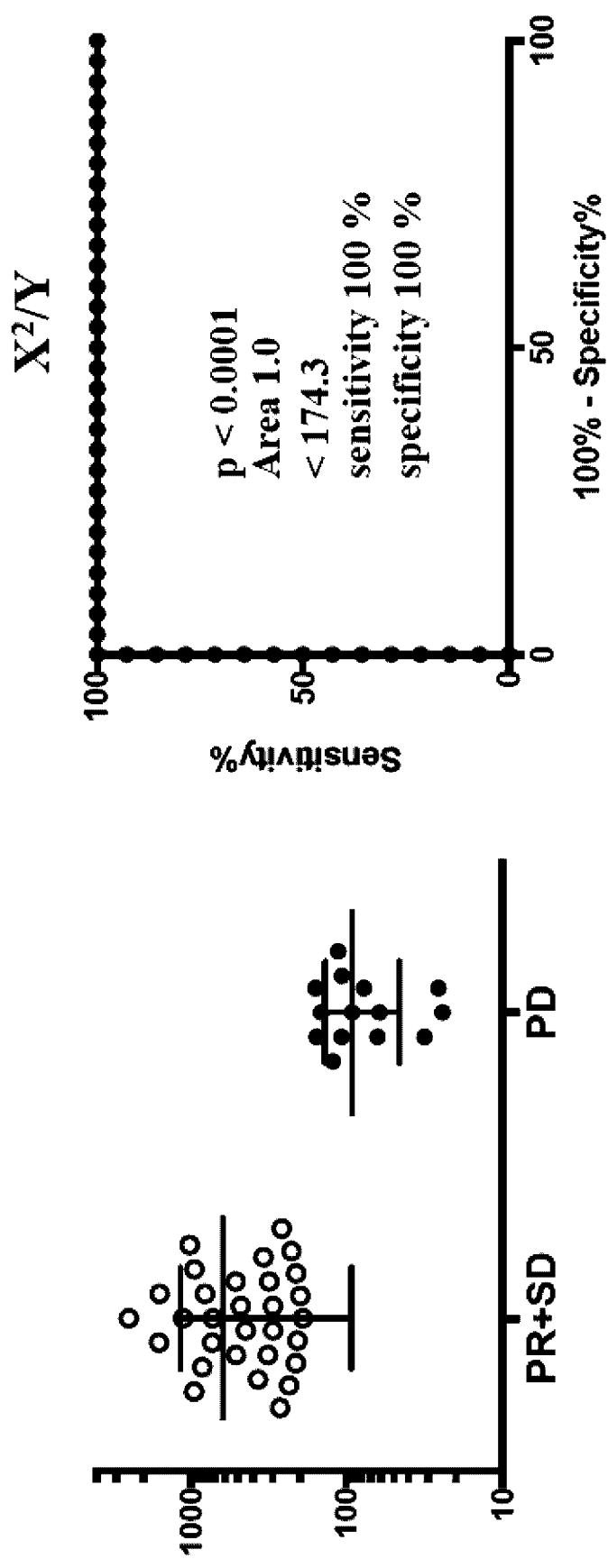
FIG. 9 shows the performance of a relative value ($X^2/Y$) of the percentage of $CD62L^{low}$ cells in $CD4^+$ T-cells (X) to the percentage of $CD25^+FoxP3^+$ cells in $CD4^+$ T-cells as an indicator for distinguishing a PR+SD group from a PD group. The right panel is a plot of sensitivity and specificity upon changing a threshold value. The area of the region under the plotted points is 1.0, which shows that the indicator is a very advantageous marker enabling the determination at sensitivity and specificity of 100%.

FIGS. 9 and 10 show results of squaring the percentage of $CD62L^{low}CD4+$ and using $X^{2}/Y$ as the relative value of X and Y in particular. It is understood that this can be utilized as a very good biomarker with sensitivity and specificity of 100%. FIG. 10 shows sensitivity and specificity for various threshold values. It is understood that this can be utilized as a very good biomarker with sensitivity and specificity of 100% when using this value with a threshold value of 174.3.

Figure 11:
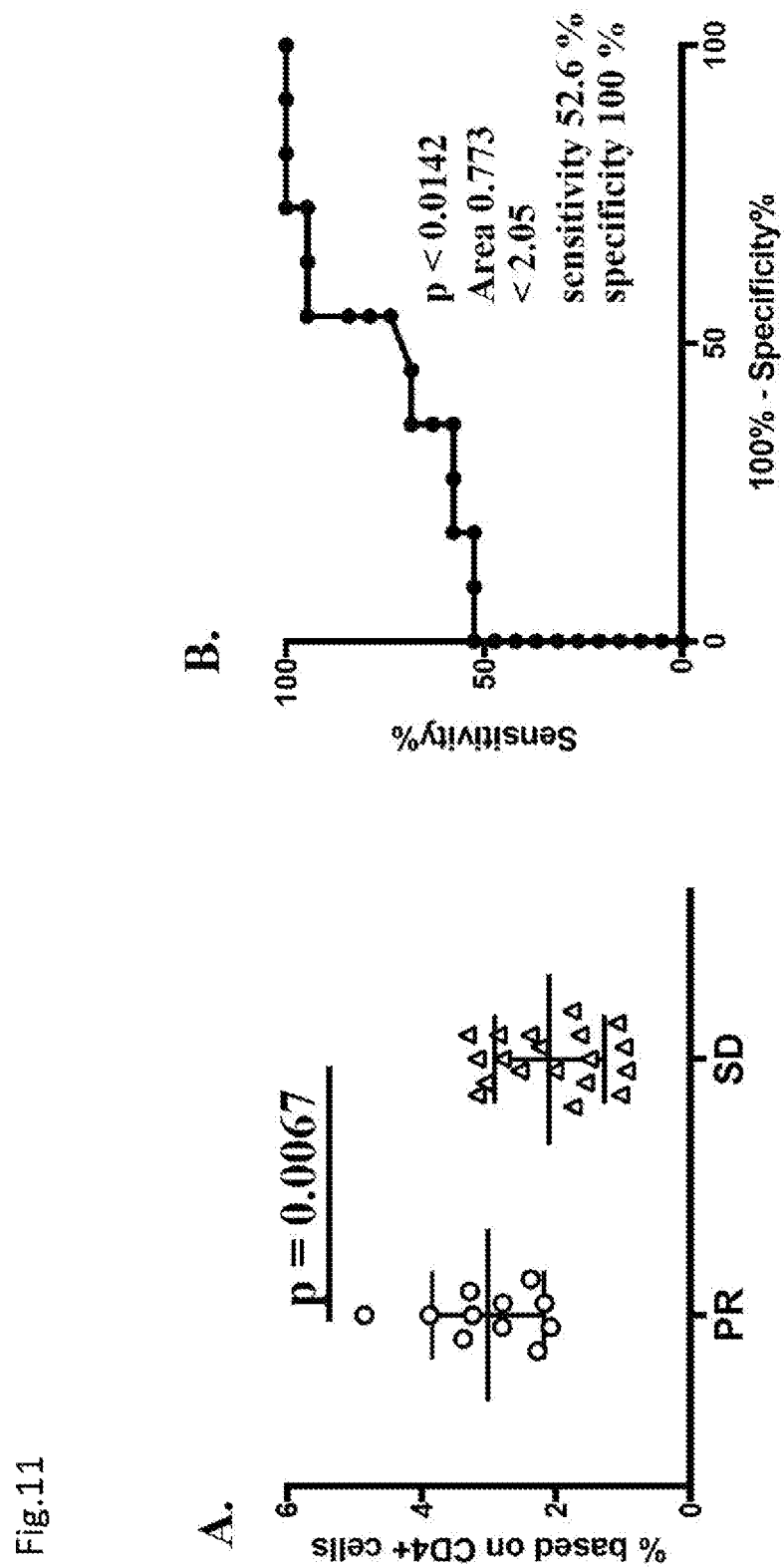
FIG. 11 shows the performance of the percentage of $CD25^+FoxP3^+$ cells in $CD4^+$ T-cells as an indicator for distinguishing a PR group and an SD group. The right panel is a plot of sensitivity and specificity upon changing a threshold value. The area of the region under the plotted points is 0.773.

FIG. 11 shows a result of examining a biomarker that can predict PR and SD after determining a PD group. It was unexpectedly discovered that there is a difference in not the percentage of $CD62L^{low}CD4+$, but in the percentage of $CD25^{+}Foxp3^{+}CD4^{+}$ cells. Since $CD25^{+}Foxp3^{+}CD4^{+}$cells are Tregs having immunosuppressive action, the percentage of $CD25^{+}Foxp3^{+}CD4^{+}$ being higher in a PR group with a greater anti-tumor immune response was an unexpected result.

PR and SD were able to be identified with sensitivity of 52.8% and specificity of 100% with a threshold value of the percentage of CD25$^+$Foxp3$^+$CD4$^+$ cells at 2.05% (FIG. 11). FIG. 12 shows sensitivity and specificity for various threshold values.

Although not wishing to be bound by any theory, the mechanism of predicting a clinical effect of cancer immunotherapy in the present invention can be understood as follows.

It is understood that CD4$^+$ T-cells transmit an instruction to dendritic cells via an MHC class I molecule, and the dendritic cells receiving the instruction stimulate CD8$^+$ T-cells via an MHC class II molecule. These CD4$^+$ T-cells encompass effector T-cells (e.g., CD62L$^{low}$CD4$^+$ T-cells) and regulatory T-cells (e.g., Foxp3$^+$CD25$^+$ T-cells). Meanwhile, the present invention predicts a clinical effect of cancer immunotherapy by evaluating the balance of both CD62L$^{low}$CD4$^+$ T-cells and Foxp3$^+$CD25$^+$ T-cells. CD62L (L-selectin) is a molecule required for recognizing and homing a high endothelial venule (HEV) that is present specifically in lymphoid organs. Since naive T-cells, when stimulated by antigen presenting cells, are primed by effector T-cells so that CD62L expression decreases, homing is no longer performed by effector T-cells. Examples of markers of effector T-cell priming of naive T-cells include CCR7 as in CD62L. As a result of priming, the expression level of CCR7 decreases. Thus, CCR7 can be used instead of CD62L$^{low}$. For example, CCR7$^{low}$CD4$^+$ T-cells and/or CCR7$^-$CD4$^+$ T-cells can be used instead of (or in addition to) CD62L$^{low}$CD4+ T-cells. Examples of cell subpopulations that can be used as an indicator of effector T-cells include, but are not limited to, subpopulations selected from the group consisting of CD62L$^{low}$CD4$^+$ T-cell subpopulation, CCR7$^-$CD4$^+$ T-cell subpopulation, LAG-3$^+$CD62L$^{low}$CD4$^+$ T-cell subpopulation, ICOS$^+$CD62L$^{low}$CD4$^+$ T-cell subpopulation, CD45RA$^-$CD4$^+$ T-cell subpopulation, CD45RO$^+$CD4$^+$ T-cell subpopulation, HLA-DR$^+$ dendritic cell subpopulation, CD80$^+$ dendritic cell subpopulation, CD86$^+$ dendritic cell subpopulation, PD-L1$^+$ dendritic cell subpopulation, CD62L$^{low}$CD8$^+$ T-cell subpopulation, and CD137$^+$CD8$^+$ T-cell subpopulation. The amount (absolute amount) and/or ratio (relative amount) of these cell subpopulations can be utilized as an indicator of effector T-cells. Examples of cell subpopulations that can be used as an indicator of regulatory T-cells include, but are not limited to, cell subpopulations selected from the group consisting of: an amount of a CCR4$^+$CD25$^+$CD4$^+$ T-cell subpopulation; an amount of a CD62L$^{high}$CD25$^+$CD4$^+$ T-cell subpopulation; an amount of a CD127$^+$CD25$^+$CD4$^+$ T-cell subpopulation; an amount of a CD45RA$^-$Foxp3$^+$CD4$^+$ T-cell subpopulation; an amount of a CD4$^+$Foxp3$^+$CD25$^+$ T-cell subpopulation; and an amount of an ICOS$^+$CD62L$^{low}$CD4$^+$ T-cell subpopulation. The amount (absolute amount) and/or ratio (relative amount) of these cell subpopulations can be utilized as an indicator of regulatory T-cells.

Example 2: Cell Therapy for Improving or Maintaining and Sustaining a Therapeutic Effect of Cancer Immunotherapy Before starting therapy with cancer immunotherapy, CD62L$^{low}$CD4$^+$ T-cells are isolated from a peripheral blood sample of a subject and stored. The isolated CD62L$^{low}$CD4$^+$ T-cells are expanded ex vivo ("ex vivo expansion" in FIG. 13). Isolated CD62L$^{low}$CD4$^+$ T-cells can be frozen and stored.

Figure 13:
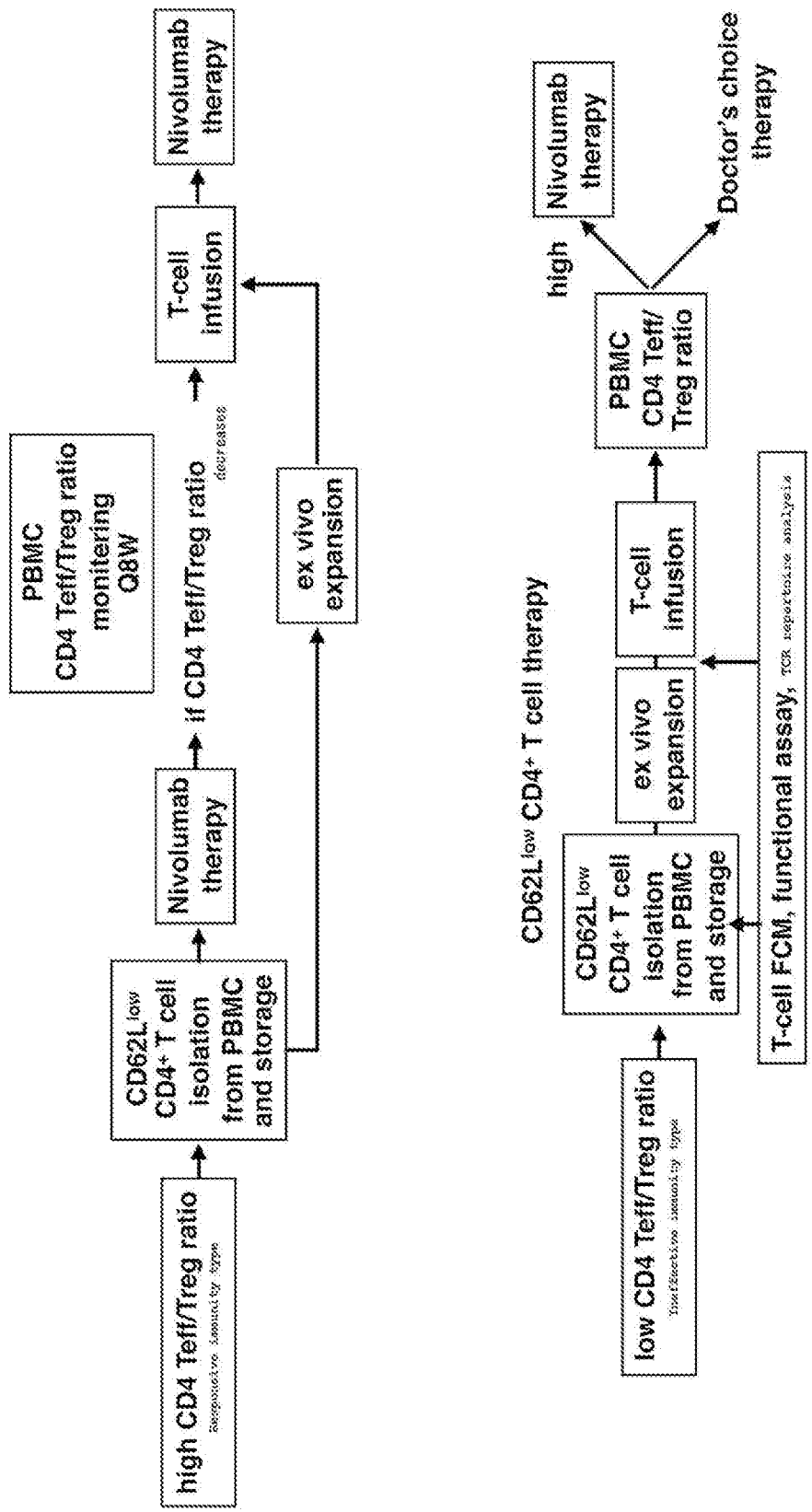
FIG. 13 is a schematic diagram showing an example of an embodiment of a method for improving or maintaining responsiveness to cancer immunotherapy of a subject.

When a subject is determined as not a part of an ineffective group by the procedure shown in Example 1 or the like, cancer immunotherapy such as therapy using an anti-PD-1 antibody such as nivolumab is applied when the ratio of CD62L$^{low}$CD4$^+$ T-cells/CD25+Foxp3$^+$CD4$^+$ T-cells is high, as shown in the top drawing of FIG. 13. During therapy, the CD4$^+$ T-cell composition of a subject is monitored by the approach disclosed in Example 1.

In this regard, upon a decrease in an indicator such as CD62L$^{low}$CD4+ percentage/CD25$^+$Foxp3$^+$CD4$^+$ T-cell composition of a subject to reach an immunological condition of an ineffective group, CD62L$^{low}$CD4$^+$ T-cells expanded ex vivo can be infused to recover the original immunological condition to sustain the effect of cancer immunotherapy.

Storage/culturing cost can be minimized by culturing and infusing only CD62L$^{low}$CD4$^+$ T-cells. This is more economical than continuing only an immune checkpoint inhibitor such as an anti-PD-1 antibody every two weeks.

A subject who has a low indicator such as CD62L$^{low}$CD4$^+$ percentage/CD25$^+$Foxp3$^+$CD4$^+$ cell percentage in the CD4$^+$ T-cell composition of the subject and is determined as a part of an ineffective group (for example, low ratio of CD62L$^{low}$CD4$^+$ T-cells/CD25+Foxp3$^+$CD4$^+$ T-cells as in the bottom drawing of FIG. 13) is infused with CD62L$^{low}$CD4$^+$ T-cells, which have been isolated from the subject and expanded ex vivo, to change the immunological condition to response group, and then cancer immunotherapy with an anti-PD-1 antibody such as nivolumab is administered. An anti-tumor immune response of cancer immunotherapy can be induced thereby even in subjects who have not been able to benefit from cancer immunotherapy with an anti-PD-1 antibody.

Example 3: Follow-Up Observation

Seven patients were subjected to follow-up to observe the percentage of CD62L$^{low}$CD4$^+$ T-cells. Peripheral blood mononuclear cells were analyzed every four weeks.

The results are shown in the following Table 3. Each of 1 to 7 represents a result for different patients.

TABLE 3

|   | % CD4 T cells | CD62Llow CD4 |
|---|---|---|
| 1 | 29.6 | 23.6 |
|   | 32.5 | 14.9 |
| 2 | 60.5 | 25.8 |
|   | 54.4 | 39.9 |
| 3 | 40.4 | 43.7 |
|   | 43.3 | 39.8 |
|   | 44.8 | 39.7 |
|   | 41.2 | 34.4 |
| 4 | 30.3 | 25 |
|   | 33.3 | 28.4 |
|   | 31.9 | 24.3 |
|   | 26.4 | 28.5 |
| 5 | 39 | 30.2 |
|   | 34.5 | 39.3 |
| 6 | 36 | 24.6 |
|   | 33.8 | 32.6 |
| 7 | 34.3 | 24.6 |
|   | 24.7 | 30.2 |

Tumor regression was observed in patient 1 in the early stages of starting nivolumab therapy, but there was swelling in the cervical lymph node for a period of time. While PD was suspected, the swelling was reduced as of the evaluation CT after 8 weeks so that the patient was determined as PR.

When an increase in tumor size was observed, the percentage of CD62L$^{low}$CD4$^+$ T-cells decreased. When the tumor again regressed, the percentage of CD62L$^{low}$CD4$^+$ T-cells was again elevated. All other subjects maintained a high percentage of CD62L$^{low}$CD4$^+$ T-cells from before the therapy, so that they were determined as PR or SD.

Combined with the findings in Example 1, it is understood that a subject would be unresponsive when the percentage of CD62L$^{low}$CD4$^+$ is less than 19.4%, but it is understood that a subject would be responsive when the percentage of CD62L$^{low}$CD4$^+$ T-cells recovers again.

Example 4: Cell Infusion to Mice

Tumor model mice were infused with cells having the composition of 2×10$^6$ CD62L$^{low}$CD4$^+$/5×10$^6$ CD62L$^{low}$CD8$^+$ (FIG. 14A "●"), 5×10$^6$ CD62L$^{low}$CD8$^+$ (FIG. 14A "Δ"), and 1×10$^6$ CD62L$^{low}$CD4$^+$ (FIG. 14B "●"). The development in tumor size over time was then observed.

The ratio of (CD62L$^{low}$ cells in CD4$^+$ T-cells)/(CD62L$^{high}$CD25$^+$ cells in CD4$^+$ T-cells) in the spleen on day 13 after tumor seeding was measured in a group infused with cells, i.e., 2×10$^6$ CD62L$^{low}$CD4$^+$/5×10$^6$CD62L$^{low}$CD8$^+$(FIG. 14A "●") or 5×10$^6$ CD62L$^{low}$CD8$^+$ (FIG. 14A "Δ"), and a group without cell infusion (FIG. 14A "○"). In a group infused with 1×10$^6$CD62L$^{low}$CD4$^+$cells (FIG. 14B "●"), the ratio of (CD62L$^{low}$ cells in CD4$^+$ T-cells)/(CD62L$^{high}$CD25$^+$ cells in CD4$^+$ T-cells) in the spleen was measured over time. T-cell analysis of peripheral blood is challenging in mice. As an alternative, a common spleen cell analysis is used. T-cell analysis in mouse spleen is considered equivalent to PBMC in humans. The T-cell fraction of CD4$^+$CD62L$^{high}$CD25$^+$ is a fraction comprising regulatory T-cells (Treg).

FIG. 14 shows the results. In the analysis of the T-cell composition on day 13, the ratio of (CD62L$^{low}$ cells in CD4$^+$ T-cells)/(CD62L$^{high}$CD25$^+$ cells in CD4$^+$ T-cells) is 10.6 in a group infused with 2×10$^6$CD62L$^{low}$CD4$_+$/5×10$^6$CD62L$^{low}$CD8$_+$cells, 2.94 in a group infused with 5×10$^6$ CD62L$^{low}$CD8$^+$ cells, and 2.70 in a group without infusion of cells. It is understood that infusion of CD62L$^{low}$CD4$_+$ cells increases the percentage of CD62L$^{low}$CD4$^+$ in the T-cell composition. Furthermore, a significant tumor regression is observed in a group infused with 2×10$^6$CD62L$^{low}$CD4$_+$/5×10$^6$CD62L$^{low}$CD8+ cells with a high ratio of (CD62L$^{low}$ cells in CD4$^+$ T-cells)/(CD62L$^{high}$CD25$^+$ cells in CD4$^+$ T-cells) (FIG. 14A "●").

The above results show that an anti-tumor effect is achieved by infusing CD62L$^{low}$CD4$^+$ cells and by infusing a mixture of CD62L$^{low}$CD4$^+$ cells and CD62L$^{low}$CD8$^+$ cells.

It can be understood that in a group infused with 1×10$^6$ CD62L$^{low}$CD4$^+$ cells, the ratio of CD62L$^{low}$ cells in CD4$^+$ T-cells/CD62L$^{high}$CD25$^+$ cells in CD4$^+$ T-cells is high due to cell infusion at a stage where tumor regression has stopped (3.70→9.09), but the ratio of (CD62L$^{low}$ cells in CD4$^+$ T-cells)/(CD62L$^{high}$CD25$^+$ cells in CD4$^+$ T-cells) is reduced (4.55) when tumor again turns to an increase. This result shows that an effect of tumor regression is achieved by CD62L$^{low}$ cells in a CD4$^+$ T-cell population, not CD62L high expression cells such as CD62L$^{high}$CD25$^+$ cells, and it is preferable to remove CD62L high expression cells from a cell containing composition achieving an anti-tumor effect.

Example 5: Isolation/Expansion of CD62L$^{low}$ Cells

Figure 15:
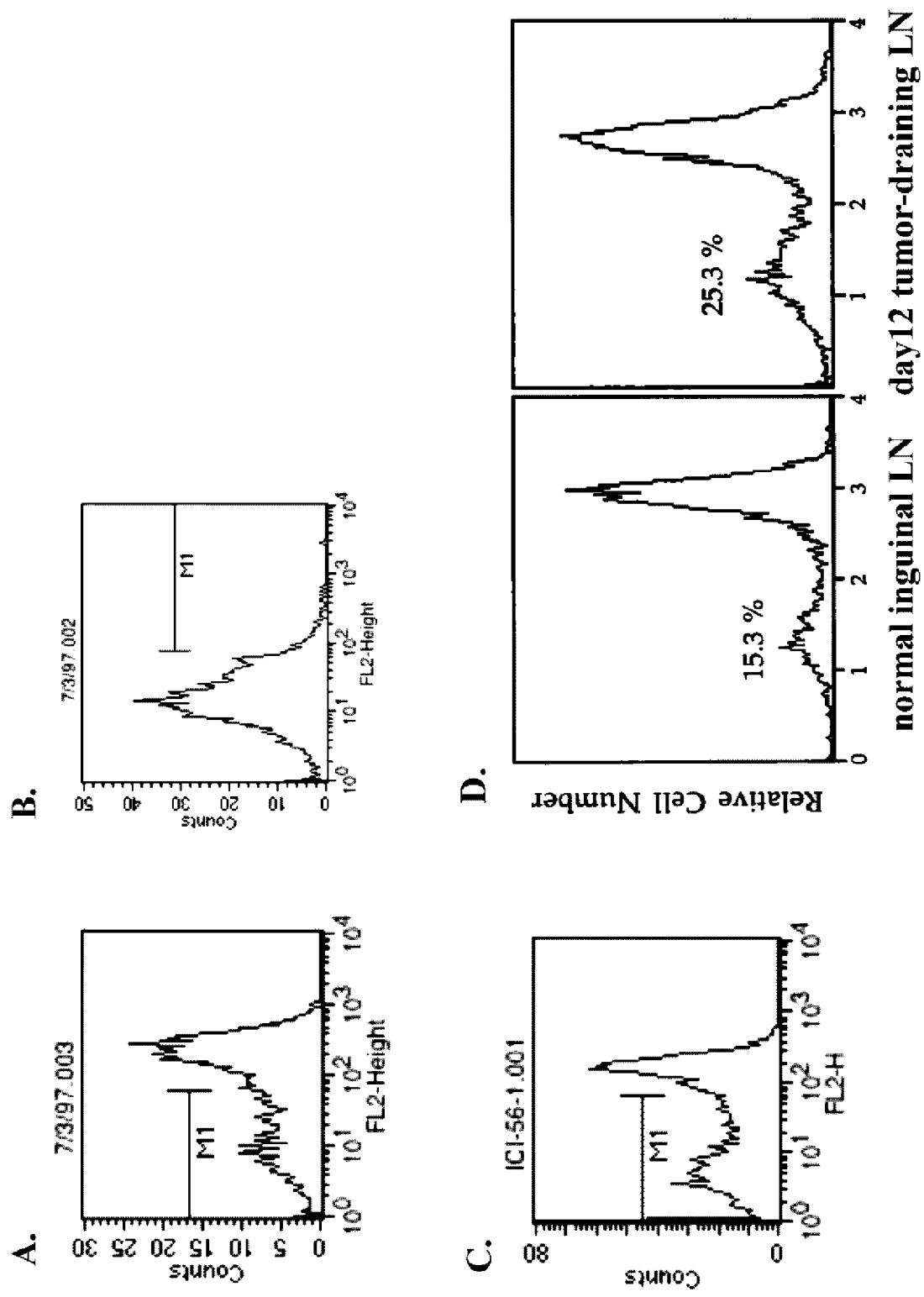
FIG. 15 is a diagram showing CD62L staining patterns of different human races and mice. Panel A shows FACS using lymph nodes draining Caucasian tumor vaccine. The lymphocytes region was gated, and CD62L was observed. C is a similar observation of CD62L from peripheral blood derived mononuclear cells of Japanese subjects. Panel D shows CD62L staining patterns in lymphocytes of mice. It is understood that similar staining patterns are exhibited across human races/organism species. This has a double peak distribution, with fluorescence intensity of $10^2$ as the boundary. Panel B is FACS showing the purity after separating only $CD62L^{low}$ cells from the group of cells of a subject in panel A with magnetic beads.

CD62L staining patterns were observed for different races and mice. FIG. 15 shows the results. Panel A shows FACS using a lymph node draining a tumor vaccine of a Caucasian. CD62L was observed while gating a lymphocyte region. C is a similar observation of CD62L from peripheral blood derived mononuclear cells of Japanese subjects. Panel D shows CD62L staining patterns in lymphocytes of mice. It is understood that similar staining patterns are exhibited across human races/organism species. This has a double peak distribution, with fluorescence intensity of 10$^2$ as the boundary.

Panel B is FACS showing the purity after separating only CD62L$^{low}$ cells from the group of cells of a subject in panel A with magnetic beads. A cell population with fluorescence intensity exceeding 10$^2$ was able to be nearly completely depleted. After separating the cells, pseudo-TCR stimulation was applied, and cells were cultured under a low concentration of IL-2. It was possible to expand the cell count 1000-fold or more.

Example 6: Utilization of Marker Expressed on Dendritic Cells

6-1. Objective

The relationship between a therapeutic effect of an anti-PD-1 antibody and a marker expressed on a dendritic cell was investigated. It was examined whether a marker expressed on dendritic cells can be utilized in predicting a clinical effect of the cancer immunotherapy in the present invention.

6-2. Materials and Methods

Materials and methods are the same as Example 1. The antibodies shown in FIG. 23 were used to detect HLA-DR and CD80/CD86 expressed on dendritic cells. The approach to determination is the same as Example 1.

6-3. Results

FIG. 16 shows the results. The ratio of HLA-DR$^+$ cells and the ratio of CD80 cells in myeloid dendritic cells (mDC, CD141$^+$CD11c$^+$ dendritic cells) and plasmacytoid dendritic cells (pDC, CD123$^+$CD11c$^+$ dendritic cells) were excellent indicators for identifying PD, SD, and PR. The p values when using HLA-DR in pDC, CD80 in pDC, HLA-DR in mDC, and CD80 in mDC for determining PD vs. PR+SD were 0.0008735, 0.002689351, 6.87852×10$^{-6}$, and 0.003033095, respectively, which are excellent values. As shown in FIG. 17, results of these markers in mDC were correlated with the ratio of CD62L$^{low}$CD4$^+$ T-cells.

In view of the above results, the number/ratio of cells expressing HLA-DR and/or CD80 and/or CD86 in a myeloid dendritic cell (mDC) and/or plasmacytoid dendritic cell (pDC) population can be used as an indicator instead of (or in addition to) using CD4$^+$ T-cells (CD62L$^{low}$CD4$^+$ T-cells) as an indicator.

Example 7: Utilization of Marker Expressed on CD8$^+$ T-Cells

7-1. Objective

The relationship between a therapeutic effect of an anti-PD-1 antibody and a marker expressed on a CD8$^+$ T-cell was investigated. It was examined whether a marker expressed on CD8$^+$ T-cells can be utilized in predicting a clinical effect of tcancer immunotherapy in the present invention.

7-2. Materials and Methods

Materials and methods are the same as Example 1. The antibodies shown in FIG. 23 were used to detect 4-1BB (CD137) expressed on CD8$^+$ T-cells. The approach to determination is the same as Example 1.

7-3. Results

FIG. 18 shows the results. The ratio of HLA-DR$^+$ cells and the ratio of CD80 cells in myeloid dendritic cells (mDC, CD141$^+$CD11c$^+$ dendritic cells) was correlated with the marker 4-1BB (CD137) expressed on CD62L$^{low}$CD8$^+$ T-cells. As was in the results of Example 6, the result of Example 7 shows that the number/ratio of 4-1BB cells in CD62L$^{low}$CD8$^+$ T-cells can be utilized to predict the clinical effect of cancer immunotherapy of the present invention in the same manner as the number/ratio of CD62L$^{low}$CD4$^+$ T-cells.

Although not wishing to be bound by any theory, it is understood that (1) CD4$^+$ T-cells transmits an instruction to dendritic cells via an MHC class I molecule, thus increasing dendritic cells expressing HLA-DR and/or CD80 and/or CD86 and (2) the dendritic cells receiving the instruction stimulate CD8$^+$ T-cells via an MHC class II molecule, thus increasing CD62L$^{low}$CD137(4-1BB)+CD8$^+$ T-cells, so that the number/ratio of CD62L$^{low}$CD137(4-1BB)$^+$CD8$^+$ T-cells and dendritic cells expressing HLA-DR and/or CD80 and/or CD86 can be used in predicting a clinical effect of cancer immunotherapy in the present invention in the same manner as the number/ratio of CD62L$^{low}$CD4$^+$ T-cells.

Furthermore, exhaustion in this series of anti-tumor mechanisms recovers due to an anti-PD-1 antibody and an anti-PD-L1 antibody, while PD-1 expression on T-cells is not effective for the prediction of the effect of the present invention (data not shown). In view of this result, it is understood that PD-L1 expression on dendritic cells can also be used in predicting a clinical effect of cancer immunotherapy in the present invention.

Example 8: Utilization of Other Markers Expressed on CD4$^+$ T-Cells 8-1. Objective It was examined whether markers other than CD62L expressed on CD4$^+$ T-cells can be utilized in predicting a therapeutic effect.

8-2. Materials and Methods

Materials and methods are the same as Example 1. The antibodies shown in FIG. 23 were used to detect various markers expressed on CD4$^+$ T-cells. The approach to determination is the same as Example 1.

8-3. Results

FIGS. 19 and 20 show the results. It is understood that each of LAG3, ICOS, and CCR4 expressed on CD4$^+$ T-cells can be used more effectively in predicting a clinical effect of cancer immunotherapy in the present invention compared to CXCR3, CCR6, and CXCR5.

Example 9: Other Markers Separating PR and SD 9-1. Objective

Example 1 demonstrated that the percentage of CD25+Foxp3+CD4+ cells is an excellent marker for separating PR and SD. Other markers for separating PR and SD were examined.

9-2. Materials and Methods

Materials and methods are the same as Example 1. The following markers using an antibody for detecting ICOS expressed on CD4$^+$ T-cells were identical to the antibodies used in Example 8. The approach to determination is the same as Example 1.

9-3. Results

As is apparent from the results shown in FIG. 21, ICOS expressed on CD4$^+$ T-cells was found to be a better marker than Foxp3$^+$CD25$^+$. Furthermore, when the ratio of CD25$^+$Foxp3$^+$CD4$^+$ T-cells in CD4$^+$ T-cells (W) and the ratio of ICOS$^+$CD62L$^{low}$CD4$^+$ T-cells in CD62L$^{low}$CD4$^+$ T-cells (Z) are combined and used as the product Z*W for distinguishing a PR group from an SD group, this was found to be usable as a marker with sensitivity of 80% and specificity of 89.5% when the threshold value of Z*W is 1.816 (FIG. 21). This result also shows that PR and SD can be distinguished using a result of calculating (e.g., multiplying) two or more W of the present invention. One non-limiting Example can distinguish PR from SD by using variables (Z, W) such as Z*W or Zn*Wn wherein n and m are each positive real number, with an amount of an ICOS$^+$CD62L$^{low}$CD4$^+$ T-cell subpopulation as (Z) and a value selected from the group consisting of:
an amount of a CD4$^+$CD25$^+$ T-cell subpopulation;
an amount of a CD4$^+$Foxp3$^+$ T-cell subpopulation;
an amount of a CD4$^+$Foxp3$^+$CD25$^+$ T-cell subpopulation;
an amount of a CD62L$^{high}$CD25$^+$CD4$^+$ T-cell subpopulation;
an amount of a CD45RA$^-$Foxp3$^+$CD4$^+$ T-cell subpopulation;
an amount of a CCR4$^+$CD25$^+$CD4$^+$ T-cell subpopulation; and
an amount of a CD127$^+$CD25$^+$CD4$^+$ T-cell subpopulation;

as (W). It is also possible to use a result of calculating (e.g., adding and/or multiplying) three of more biomarkers for distinguishing PR from SD.

To derive a more detailed formula for an indicator, logistic regression was performed to further examine a formula combining the ratio of CD25+Foxp3$^+$CD4$^+$ T-cells in CD4$^+$ T-cells (W) and the ratio of ICOS$^+$CD62L$^{low}$CD4$^+$ T-cells in CD62L$^{low}$CD4$^+$ T-cells (Z).

As shown in FIGS. 24 and 25, the formula of J=Z*W$^5$ was derived from the result in a sample of N=32. When PR and SD were separated using the formula J=Z*W$^5$ as an indicator, ROC analysis showed that the performance was improved compared to each of Z and W (FIG. 26). In addition, it is understood that PR and SD can be successfully separated using another formula with a similar form, J=Z*W$^{4-6}$.

Because CD4$^+$ T cells are critical to predict PD-1/PD-L1 blockade therapy NR, the inventors next examined whether PD-1 and LAG-3 expression on CD4$^+$ T cells can be a marker distinguishing PR group and SD group, in addition to ICOS expression. The lymphocyte-activation gene 3 (LAG-3) protein, which is expressed on activated T cells, interacts with PD-1 to maintain T cell exhaustion. LAG-3 binds to MHC class II antigens and regulates the expanding effector T cell population size following antigen activation (28-30 Hui, E., et al. T cell costimulatory receptor CD28 is a primary target for PD-1-mediated inhibition. Science 355, 1428-1433 (2017); Baixeras, E., et al. Characterization of the lymphocyte activation gene 3-encoded protein. A new ligand for human leukocyte antigen class II antigens. J Exp Med 176, 327-337 (1992); Workman, C. J., et al. Lymphocyte activation gene-3 (CD223) regulates the size of the expanding T cell population following antigen activation in vivo. J Immunol 172, 5450-5455 (2004)). The inventors thus examined PD-1, LAG-3, and ICOS expression on gated CD62L$^{high}$ and CD62L$^{low}$ CD4$^+$ T cells.

The result is shown in FIG. 32. These molecules were expressed on CD62L$^{low}$CD4$^+$ T cells but minimally detected on CD62L$^{high}$ CD4$^+$ T cells (FIG. 32d-e). Post hoc tests following one-way analysis of variance (ANOVA) showed, notably, that IR (SD) possessed significantly lower PD-1+, LAG-3+, and ICOS+ cell percentages in the total CD62L$^{low}$CD4+ T cell population compared with GR (PR) and NR (FIG. 32a-c). It is likely that IR had a CD4+ T cell immunity state distinct from that of GR. Thus, it is possible to distinguish PR from SD using the amount of these cell subpopulations.

It is understood from the result of this Example, that the amount/ratio of LAG-3+ CD62L$^{low}$CD4+ T-cell and PD-1+ CD62L$^{low}$CD4+ T-cell subpopulation can be used as a marker to distinguish PR and SD, in addition to ICOS+ CD62L$^{low}$CD4+ T-cell.

Example 10: Survival Analysis 10-1. Summary

In order to demonstrate the prediction of therapeutic effect with the prediction formula ($X^2/Y$, wherein X=the ratio of CD62L$^{low}$ T-cells in the CD4+ T-cell population (%) and Y=the ratio of CD25+FOXP3+ T-cells in the CD4+ T-cell population (%)), the survival duration is analyzed in the discovery cohort (a portion of subject patient population of Example 1) whose treatment outcome (PD, SD, CR) have been determined. Further, in an independent validation cohort consisting of 41 patients continuing a treatment, whose prediction formulas were analyzed before assessment of tumor responsiveness, whether the prediction formula could distinguish NR (PD) was examined.

10-2. Materials and Methods

Characteristics of the patient group included in the discovery cohort and the validation cohort were as shown in the following table. The prediction formula values for each patient were calculated in accordance with the procedure described in Example 1.

TABLE 4 a. Patient Characteristics

| Discovery cohort: n = 40 | | Validation cohort: n = 41 | |
|---|---|---|---|
| Age-yr | | Age-yr | |
| Median | 67 | Median | 71 |
| Range | 51-84 | Range | 38-85 |
| Sex-no. (%) | | Sex-no. (%) | |
| Male | 26 (65) | Male | 35 (85.4) |
| Female | 14 (35) | Female | 6 (14.6) |
| Histology-no. (%) | | Histology-no. (%) | |
| Sq | 10 (25) | Sq | 10 (24.4) |
| Non-Sq | 30 (75) | Non-Sq | 31 (75.6) |
| Smoking history-no. (%) | | Smoking history-no. (%) | |
| Current or former smoker | 29 (72.5) | Current or former smoker | 38 (92.7) |
| Never smoked | 11 (27.5) | Never smoked | 3 (7.3) |
| Disease stage-no. (%) | | Disease stage-no. (%) | |
| c-stageIII | 9 (22.5) | c-stageIII | 9 (22.0) |
| c-stageIV | 22 (55) | c-stageIV | 25 (61.0) |
| post-operative recurrence | 9 (22.5) | post-operative recurrence | 7 (17.1) |
| EGFR status-no. (%) | | EGFR status-no. (%) | |
| Wild type | 33 (82.5) | Wild type | 41 (100) |
| Mutated (Exon19 del or L858R) | 7 (17.5) | Mutated (Exon19 del or L858R) | 0 (0) |

10-3. Results

The prediction formula ($X^2/Y$, wherein X=the ratio of CD62L$^{low}$ T-cells in the CD4+ T-cell population (%) and Y=the ratio of CD25+FOXP3+ T-cells in the CD4+ T-cell population (%)) values for each patient in the discovery cohort are shown in FIG. 30a (P<0.0047, t=3.004, df=38). The prediction formula receiver operating characteristic (ROC) analysis to detect NR at 8 weeks within the discovery cohort is shown in FIG. 30b. Sensitivity and specificity were 85.7% and 100%, respectively, at the prediction formula threshold value=192. The progression-free survival (PFS) and OS curves of patients diagnosed as responder type ($X^2/Y>=192$) and NR type ($X^2/Y<192$) according to PBMCs obtained before Nivolumab treatment are shown in FIGS. 30c and d. Responder and NR types in the discovery cohort (threshold=192) differed significantly (P<0.0001) in both PFS and OS.

Next, the Inventors explored whether the prediction formula threshold value ($X^2/Y<192$) could differentiate NRs in the independent validation cohort consisting of 41 consecutive patients whose peripheral blood was collected prior to Nivolumab therapy as the discovery cohort but was analyzed before tumor response evaluation. The prediction formula values were significantly higher (P=0.00068, t=3.693, df=39) in responding validation cohort patients as shown in FIG. 30e. The sensitivity and specificity values of NR validation cohort patient prediction were 90.9% and 89.5% at the <192 threshold, respectively. Responder-type PFS was significantly longer than NR-type in validation cohort patients (FIG. 30f; P<0.0001). Although the median follow-up time was only 195 days, responder-type patients also had significantly longer OS (FIG. 30g; P=0.0022).

The objective responses at 8 week in each cohort were as follows.

TABLE 5 b. Responses to Nivolumab

| Discovery cohort: n = 40 Objective response at 8 weeks- no. (%) | | Validation cohort: n = 41 Objective response at 8 weeks- no. (%) | |
|---|---|---|---|
| Complete or partial response | 11 (27.5) | Complete or partial response | 7 (17.1) |
| Stable disease | 15 (37.5) | Stable disease | 12 (29.3) |
| Progressive disease | 14 (35) | Progressive disease | 22 (53.7) |

Abbreviations: Sq, squamous; c-stage, clinical stage; del, deletion.

The results in this Example showed that the method of predicting responsiveness to cancer immunotherapy described herein predicts accurately responsiveness to cancer immunotherapy, also in prospective study. Further, prediction of responsiveness to cancer immunotherapy also provides direct prediction of overall treatment response (overall survival (OS) or progression-free survival (PFS)) of patients.

Example 11: The Availability of CD28+ Cells Subpopulation as a Marker

Recently, it was demonstrated that CD28, but not the T cell receptor (TCR), is a primary target of PD-1-dependent signal inhibition. Thus, the Inventors examined if the percentage of CD28+ cells in the total population of CD8+ T cells correlated with the prediction formula value.

The Inventors found that the prediction formula ($X^2/Y$, wherein X=the ratio of CD62L$^{low}$ T-cells in the CD4+ T-cell population (%) and Y=the ratio of CD25+FOXP3+ T-cells in the CD4+ T-cell population (%)) values significantly (P=0.0045) correlated with the percentage of CD28+ cells in the total population of CD62L$^{low}$CD8+ T cell (FIG. 31). From the results of this Example, it is understood that an amount of $CD28^+CD62L^{low}CD8^+$ T-cell and/or a ratio of CD28+ cells in a $CD62L^{low}CD8^+$ T-cell population can be used for prediction of responsiveness to cancer immunotherapy of patients, as well as said prediction formula value.

Example 12: CD62Llow CD4+ T Cell Gene Expression in Patients of Each Group 12-1. Summary PBMC flow cytometry (FCM) analyses revealed that $CD62L^{low}CD4^+$ T cell quantity and quality play a critical role in antitumor immunity and determine PD-1 blockade therapy response. The inventors performed microarray analysis to view $CD62L^{low}CD4^+$ T cell differences at the molecular level among GR, IR, and NR patients in this Example. The Inventors first elucidated gene expression differences in $CD62L^{high}CD4^+$ and $CD62L^{low}CD4^+$ T cells. Then the differentiallydifferential expressed gene on $CD62L^{low}CD4^+$ T cells of the patients of each group was explored.

12-2. Materials and Methods

Total RNAs were isolated by TRIzol reagent (Thermo Fisher Science, Waltham, Mass.) from $CD62L^{high}$ CD4+ and $CD62L^{low}$ CD4+ T cells in PBMCs purified from two of each responder type. cDNA and cRNA synthesis and single-stranded cDNA (ssDNA) labeling reactions were performed according to the manufacture's instruction using the WT Plus Reagent Kit (Thermo Fisher Scientific). Total RNA (0.5 µg) was reverse transcribed into cDNA and subsequently synthesized into cRNA. ssDNA was reverse transcribed from 15 µg of cRNA and then labeled; 1.8 µg of labeled ssDNA was hybridized with microarray Clariom S assays for Human (Thermo Fisher Scientific) in a GeneChip Hybridization Oven 645. Hybridized arrays were scanned using the GCS3000 7G System (Thermo Fisher Scientific). The accession number ID of the gene expression data is GSE103157.

To identify the gene expression signature from two sets of gene expression data, the Inventors estimated the difference of gene expression between the two sets as follows. First, the Inventors performed the outlier test for all values of probes, and then calculated a z-score for each probe using the average and the variance of the probe values except for outliers. To compare two gene sets of z-scores, the z-score of each gene was transformed into probability, and then each difference of gene probability between the two sets, $p^d$ was calculated; i.e., $$p_k^d = |p(z_k^a) - p(z_k^b)| = \left| \frac{1}{\sqrt{2\pi}} \int_{-\infty}^{z_k^a} e^{-\frac{z}{2}} dz - \frac{1}{\sqrt{2\pi}} \int_{-\infty}^{z_k^b} e^{-\frac{z}{2}} dz \right|$$ [Math. 1]

where the k-th gene between the two gene sets, a and b, was compared. In this analysis, the Inventors selected the genes with $$P_k^d > 0.2$$ [Math.2]

as the gene signature.

12-3. Results

For this, the Inventors first elucidated gene expression differences in $CD62L^{high}CD4^+$ and $CD62L^{low}CD4^+$ T cells. $CD62L^{high}$ CD4+ T cells and $CD62L^{low}$ CD4+ T cells have distinct gene expression profiles (FIGS. 33a and 34a). Consistent with previous reports, the majority of $CD62L^{high}$ CD4+ T cells are considered as naive T cells because the C—C chemokine receptor type 7 (CCR7), CD28, and transcription factor 7 (TCF7) genes were highly expressed in $CD62L^{high}$ CD4+ T cells in all GR, IR, and NR patients. A few $CD62L^{high}$ CD4+ T cells are considered regulatory T cells because of higher foxp3 expression.

Then, the Inventors merged the genes in the signatures compared between the cells from GR and IR, GR and NR, IR and NR, GR+IR and NR, and GR and IR+NR (1884, 1826, 1410, 1167, and 1513 genes, respectively) (totaling 3484) (FIG. 33b). Among these, the expression of 30 from 53 genes known to be related to T-cell immunity was shown in terms of Nivolumab-treatment response (FIG. 34b). This indicated that C—X—C chemokine receptor type 3 (CXCR3), interleukin-23 receptor (IL23R), interleukin-13 receptor subunit alpha-2 (IL13RA2), PD-1 ligand 2 (PDL2), CD80, C-type lectin domain family 2 member A (CLEC2A), interleukin 7 (IL7), transforming growth factor beta receptor 3 (TGFBR3), and histone deacetylase 9 (HDAC9) were preferentially expressed in $CD62L^{low}$ CD4+ T cells derived from GR and/or IR.

As can be understood from the results of this Example, it is possible to determine a cell subpopulation that an obtained cell belongs to by examining the expression of differentially differential expressed genes between $CD62L^{high}CD4^+$ and $CD62L^{low}CD4^+$ T-cells, and it is thus possible to measure an amount and/or ratio of a cell subpopulation. Further it is understood that distinction of patients group can be achieved by examining the expression of differential expressed genes among respective patients groups on $CD62L^{low}$ CD4+ T-cells.

Example 13: Cell Transfer Experiment

Preparation of $CD62L^{low}CD4^+$ T cells from tumor-draining lymph nodes $1.5\times10^6$ B16BL6 melanoma cells (in HBSS) was inoculated to B6 mice subcutaneously. Inguinal lymph nodes were harvested 9 to 10 days after. From harvested lymph nodes, CD4+ T-cells were isolated with CD4+ T-cell Isolation Kit+LS column. $CD62L^{low}CD4^+$ T-cells were purified by negative selection with CD62L microbeads (LS column). These $CD62L^{low}CD4^+$ T-cells were used for intravenous transfer.

Tumor Model $3\times10^6$ B16BL6 melanoma cells in HBSS were inoculated on midline of abdomen B6 mice subcutaneously. The mice were divide into (1) Control group (N=10), (2) Antibody group (N=17), and (3) Antibody+Cell group (N=4). No treatment was administered to Control group. After inoculating tumor cells to the Antibody+Cell group, the above $CD62L^{low}CD4^+$ T-cells ($1*10^6$) were transferred on Day 4 or Day 5 after tumor inoculation, and anti-PD-1 antibody (RMP1-14 BioXcell 250 µg) was administered intraperitoneally (on the day of cell administration, 3 days after and 6 days after cell administration). For the Antibody group, anti-PD-1 antibody (RMP1-14 BioXcell 250 µg) was administered intraperitoneally (on the day of cell administration, 3 days after and 6 days after cell administration). The survival ratio of mice in each group was monitored.

Results

On day 16 after the administration of the antibody and/or T-cells, all individuals in Control group died, while the survival ratio of the Antibody+Cell group was 50%, which was higher than that of the Antibody group (FIG. 35). These results showed that the transfer of $CD62L^{low}CD4^+$ T-cells can enhance the efficacy of anti PD-1 antibodies.

INDUSTRIAL APPLICABILITY

Anti-PD-1/PD-L1 antibodies are considered as primary therapy for almost all progressive cancer therapy. Meanwhile, the Ministry of Health, Labour and Welfare has warned that expensive drug costs can potentially increase the social security cost, so that the incremental cost-effectiveness ratio (ratio of increase in therapeutic effect to increase in drug cost) must be increased. The biomarkers provided in the present invention are medically and socially essential because they can predict an effect of an anti-PD-1/PD-L1 antibody in a simple, low cost, and accurate manner. The present invention is understood as a technique that is demanded worldwide for all cancers and tumors, thus having a very high market value.

The invention claimed is:

1. A method of predicting a response to cancer immunotherapy of a subject, the method comprising:

measuring an amount of $CD4^+CD62L^{low}$ T-cells—of the subject (X);

measuring an amount of $CD4^+Foxp3^+CD25^+$ T-cells—of the subject (Y);

comparing a ratio of X to Y with an ineffective group threshold value, wherein a ratio of X to Y that is higher than the ineffective group threshold value indicates that the subject is not a part of an ineffective group to the cancer immunotherapy; and applying a cancer immunotherapy to the subject predicted to be not a part of an ineffective group;

wherein the cancer immunotherapy comprises administration of an immune checkpoint inhibitor.

2. The method of claim 1, wherein the ratio is X/Y.

3. The method of claim 1, wherein the ratio is $X^2/Y$.

4. The method of claim 1, further comprising using a ratio of a $Foxp3^+CD25^+$ T-cell subpopulation in $CD4^+$ T-cells, a ratio of an $ICOS^+CD62L^{low}CD4^+$ T cell subpopulation in $CD62L^{low}CD4^+$ T-cells, a ratio of $LAG-3^+CD62L^{low}CD4^+$ T cell subpopulation in $CD62L^{low}CD4^+$ T-cells, or a ratio of $PD-1^+CD62L^{low}CD4^+$ T cell subpopulation in $CD62L^{low}CD4^+$ T-cells, in the subject who is shown to be not a part of the ineffective group as an indicator of a response to the cancer immunotherapy of the subject, wherein the ratio of the $Foxp3^+CD25^+$ T-cell subpopulation in the $CD4^+$ T-cells, the ratio of the $ICOS^+CD62L^{low}CD4^+$ T cell subpopulation in the $CD62L^{low}CD4^+$ T-cells, the ratio of $LAG-3^+CD62L^{low}CD4^+$ T cell subpopulation in $CD62L^{low}CD4^+$ T-cells, or the ratio of $PD-1^+CD62L^{low}CD4^+$ T cell subpopulation in $CD62L^{low}CD4^+$ T-cells, higher than a response group threshold value indicates that the subject is a part of a response group.

5. The method of claim 1, wherein the ineffective group threshold value is determined so that sensitivity for the detection of an ineffective group exceeds about 90%, or wherein the ineffective group threshold value is determined so that specificity for the detection of an ineffective group exceeds about 90%.

6. The method of claim 1, wherein the amount of the cell population is measured using a peripheral blood sample.

7. The method of claim 1, wherein the immune checkpoint inhibitor is selected from the group consisting of a PD-1 inhibitor and a PD-L1 inhibitor.

8. The method of claim 7, wherein the PD-1 inhibitor or PD-L1 inhibitor comprises nivolumab, pembrolizumab, durvalumab, atezolizumab, or avelumab.

9. The method of claim 1, wherein the X is a ratio of a $CD62L^{low}CD4^+$ T-cell subpopulation in $CD4^+$ T-cells, and the Y is a ratio of a $Foxp3^+CD25^+CD4^+$ T-cell subpopulation in $CD4^+$ T-cells.

* * * * *